US008758409B2

(12) United States Patent
Hochschuler et al.

(10) Patent No.: US 8,758,409 B2
(45) Date of Patent: Jun. 24, 2014

(54) INTERLAMINAR STABILIZING SYSTEM

(75) Inventors: Stephen H. Hochschuler, Paradise Valley, AZ (US); Brian P. Janowski, Marquette, MI (US); Thomas S. Kilpela, Marquette, MI (US); Matthew N. Songer, Marquette, MI (US); Qi-bin Bao, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 1042 days.

(21) Appl. No.: 12/161,676

(22) PCT Filed: Jan. 23, 2007

(86) PCT No.: PCT/US2007/060923
§ 371 (c)(1),
(2), (4) Date: Jan. 5, 2011

(87) PCT Pub. No.: WO2007/087535
PCT Pub. Date: Aug. 2, 2007

(65) Prior Publication Data
US 2011/0106163 A1    May 5, 2011

Related U.S. Application Data

(60) Provisional application No. 60/761,677, filed on Jan. 23, 2006.

(51) Int. Cl.
A61B 17/70    (2006.01)
(52) U.S. Cl.
CPC .................................. A61B 17/7065 (2013.01)
USPC ........................................................ 606/249
(58) Field of Classification Search
USPC .................................................. 606/246–279
See application file for complete search history.

(56) References Cited

U.S. PATENT DOCUMENTS

| 2,677,369 | A | * | 5/1954 | Knowles | 606/249 |
| 5,007,909 | A | * | 4/1991 | Rogozinski | 606/277 |
| 5,011,484 | A | * | 4/1991 | Breard | 606/249 |
| 5,496,318 | A | * | 3/1996 | Howland et al. | 606/249 |
| 5,836,948 | A | * | 11/1998 | Zucherman et al. | 606/249 |
| 5,860,977 | A | * | 1/1999 | Zucherman et al. | 606/249 |
| 5,876,404 | A | * | 3/1999 | Zucherman et al. | 606/249 |
| 6,048,342 | A | * | 4/2000 | Zucherman et al. | 606/249 |
| 6,068,630 | A | * | 5/2000 | Zucherman et al. | 606/249 |
| 6,152,926 | A | * | 11/2000 | Zucherman et al. | 606/279 |
| 6,156,038 | A | * | 12/2000 | Zucherman et al. | 606/249 |
| 6,190,387 | B1 | * | 2/2001 | Zucherman et al. | 606/249 |
| 6,238,397 | B1 | * | 5/2001 | Zucherman et al. | 606/279 |
| 6,332,883 | B1 | * | 12/2001 | Zucherman et al. | 606/249 |
| 6,358,254 | B1 | * | 3/2002 | Anderson | 606/103 |
| 6,379,355 | B1 | * | 4/2002 | Zucherman et al. | 606/249 |
| 6,419,676 | B1 | * | 7/2002 | Zucherman et al. | 606/249 |

(Continued)

Primary Examiner — Ellen C Hammond
Assistant Examiner — Stuart S Bray
(74) Attorney, Agent, or Firm — Fitch, Even, Tabin & Flannery LLP

(57) ABSTRACT

A spinal stabilization system includes a first engagement member and a support structure. The first engagement member is adapted to be disposed between a first vertebra and a second vertebra. The engagement member generally includes a seating surface for accommodating at least a portion of a laminar region of the first vertebra. The support structure engages a portion of the second vertebra. The structural cooperation of the first engagement member and the support structure is such that the engagement member restricts reduction of the intervertebral spacing between the first and second vertebrae.

5 Claims, 54 Drawing Sheets

(56) References Cited

U.S. PATENT DOCUMENTS

| | | |
|---|---|---|
| 6,451,019 B1 * | 9/2002 | Zucherman et al. .......... 606/249 |
| 6,451,020 B1 * | 9/2002 | Zucherman et al. .......... 606/249 |
| 6,500,178 B2 * | 12/2002 | Zucherman et al. .......... 606/249 |
| 6,514,256 B2 * | 2/2003 | Zucherman et al. .......... 606/249 |
| 6,582,433 B2 * | 6/2003 | Yun .............................. 606/249 |
| 6,626,944 B1 * | 9/2003 | Taylor ........................ 623/17.16 |
| 6,641,585 B2 * | 11/2003 | Sato et al. ..................... 606/261 |
| 6,695,842 B2 * | 2/2004 | Zucherman et al. .......... 606/249 |
| 6,699,246 B2 * | 3/2004 | Zucherman et al. .......... 606/249 |
| 6,699,247 B2 * | 3/2004 | Zucherman et al. ......... 606/86 A |
| 6,761,720 B1 * | 7/2004 | Senegas ......................... 606/249 |
| 6,946,000 B2 * | 9/2005 | Senegas et al. ............ 623/17.11 |
| 7,029,473 B2 * | 4/2006 | Zucherman et al. .......... 606/249 |
| 7,510,567 B2 * | 3/2009 | Zucherman et al. .......... 606/249 |
| 7,585,316 B2 * | 9/2009 | Trieu ............................ 606/279 |
| 7,635,377 B2 * | 12/2009 | Zucherman et al. .......... 606/249 |
| 7,666,208 B1 * | 2/2010 | Asfora .......................... 606/249 |
| 7,666,209 B2 * | 2/2010 | Zucherman et al. .......... 606/249 |
| 7,670,380 B2 * | 3/2010 | Cauthen, III .............. 623/17.16 |
| 7,776,069 B2 * | 8/2010 | Taylor ........................... 606/249 |
| 7,811,307 B2 * | 10/2010 | Deneuvillers et al. ........ 606/249 |
| 7,828,822 B2 * | 11/2010 | Zucherman et al. .......... 606/249 |
| 7,828,845 B2 * | 11/2010 | Estes et al. ................. 623/17.11 |
| 7,862,615 B2 * | 1/2011 | Carli et al. ................. 623/17.11 |
| 7,901,432 B2 * | 3/2011 | Zucherman et al. .......... 606/249 |
| 7,988,709 B2 * | 8/2011 | Clark et al. ................... 606/249 |
| 8,007,521 B2 * | 8/2011 | Malandain et al. ........... 606/279 |
| 8,034,080 B2 * | 10/2011 | Malandain et al. ........... 606/249 |
| 8,043,335 B2 * | 10/2011 | Malandain et al. ........... 606/249 |
| 8,066,742 B2 | 11/2011 | Anderson et al. |
| 8,083,795 B2 * | 12/2011 | Lange et al. ............... 623/17.11 |
| 8,105,363 B2 * | 1/2012 | Fielding et al. .............. 606/279 |
| 8,123,782 B2 * | 2/2012 | Altarac et al. ................ 606/249 |
| 8,128,663 B2 * | 3/2012 | Zucherman et al. .......... 606/249 |
| 8,147,526 B2 * | 4/2012 | Auyoung ..................... 606/279 |
| 8,147,548 B2 * | 4/2012 | Zucherman et al. ....... 623/17.11 |
| 8,157,841 B2 * | 4/2012 | Malandain et al. ........... 606/249 |
| 8,216,277 B2 * | 7/2012 | Zucherman et al. .......... 606/249 |
| 8,221,463 B2 * | 7/2012 | Zucherman et al. .......... 606/249 |
| 8,221,465 B2 * | 7/2012 | Trieu et al. .................... 606/249 |
| 8,236,056 B2 * | 8/2012 | Pasquet et al. ............. 623/17.11 |
| 2002/0147449 A1 * | 10/2002 | Yun ................................ 606/61 |
| 2004/0049188 A1 * | 3/2004 | Slivka et al. ................... 606/61 |
| 2005/0143818 A1 * | 6/2005 | Yuan et al. ................. 623/17.11 |
| 2005/0165485 A1 * | 7/2005 | Trieu ........................ 623/17.13 |
| 2005/0261768 A1 * | 11/2005 | Trieu ........................ 623/17.11 |
| 2006/0235387 A1 * | 10/2006 | Peterman ........................ 606/61 |
| 2006/0235532 A1 * | 10/2006 | Meunier et al. ............ 623/17.16 |

* cited by examiner

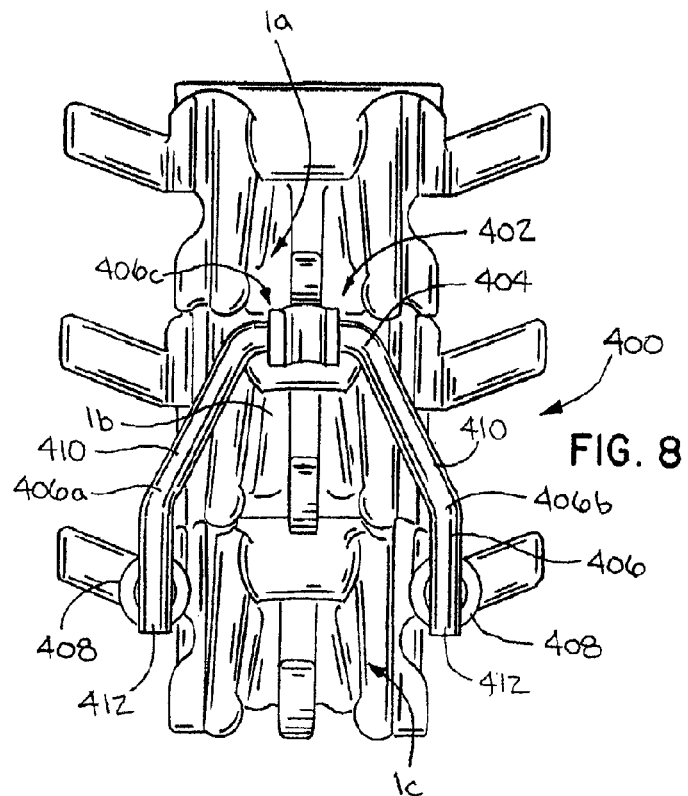
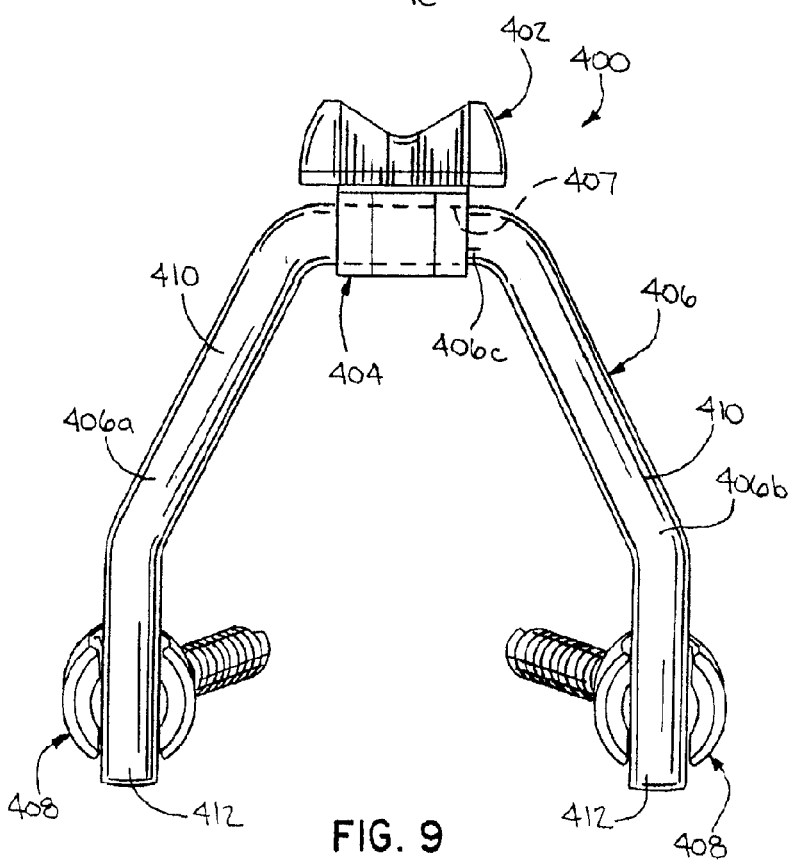

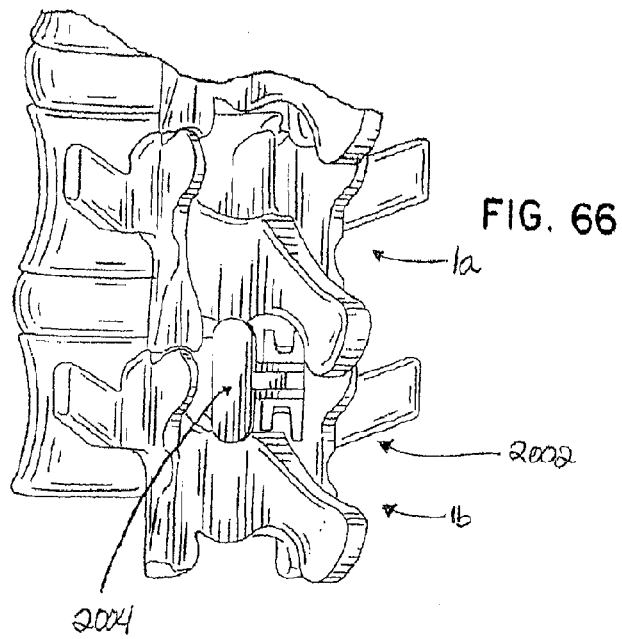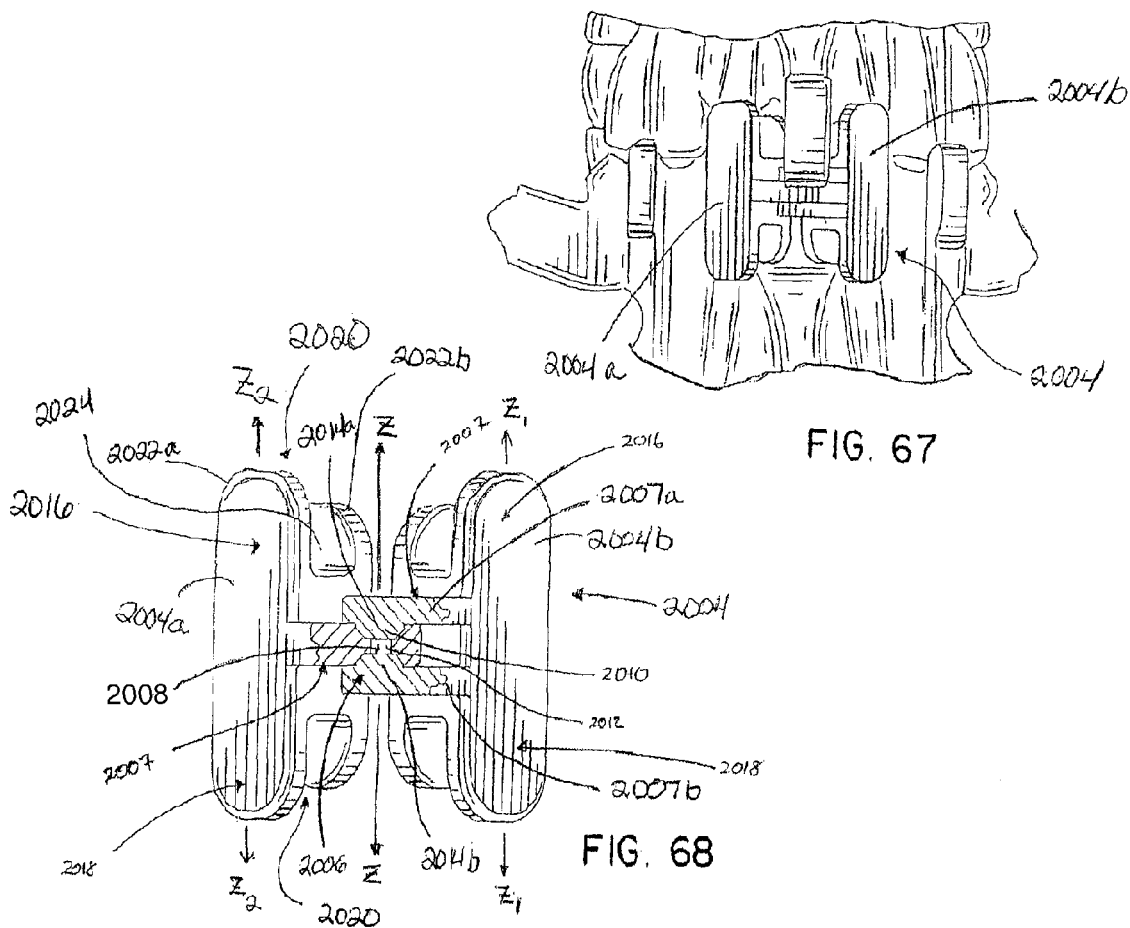

INTERLAMINAR STABILIZING SYSTEM

FIELD OF THE INVENTION

The present invention relates generally to a spinal stabilization system and, more particularly, a spinal stabilization system for limiting either distraction or reduction of the intervertebral spacing between adjacent vertebrae.

BACKGROUND OF THE INVENTION

Many conventional spinal stabilization systems may be categorized as including interspinous support systems, laminar hook systems, longitudinal rod systems or some combination thereof. Interspinous support systems generally include a spacer disposed between and directly engaging adjacent spinous processes. The spacer may include seating surfaces that are contoured or configured to fittingly engage or receive the opposing spinous processes, thereby maintaining the axial and/or lateral disposition of the spacer relative thereto. Such interspinous spacers provide a support structure adapted to reduce or limit any reduction in the intervertebral spacing between the adjacent vertebrae. Typical laminar hook systems include one or more pair of hooks interconnected by a flexible cable or cord. The hooks, which are connected to opposing ends of the cable or cord, attach to the superior and inferior laminar edge regions of adjacent vertebrae. The flexible cords are then adjusted to the appropriate length such that the laminar hooks remain engaged with and limit the distraction of the adjacent vertebra. Typical longitudinal rod systems include one or more rods disposed along one or both sides of the interspinous processes of multiple vertebra of the spine. The longitudinal rods are fixed to the one or more of the vertebrae via fixation devices such as bone screws. Additionally, some longitudinal rod systems often include fasteners and/or plates fixing the longitudinal rods directly to the interspinous processes.

While multiple variations of the aforementioned spinal stabilization systems have been successfully implemented for correcting spinal alignment, relative shortcomings do exist. For example, interspinous spacer systems rely on direct engagement between adjacent interspinous processes. This system relies on a reactive moment applied directly to one or both of the spinous processes. Because of the configuration and location of the spinous processes relative to the remainder of the vertebra, the moment generated by these systems can potentially cause misalignment of the corresponding vertebrae relative to the rest of the spine. Thus, the systems often implement an additional component such as a flexible band and/or cord wrapped around the adjacent spinous processes to limit misalignment thereof. Additionally, such interspinous spacer systems, as stated above, directly abuttingly engage the spinous processes. Accordingly, the interspinous spacer systems rely on the integrity of the spinous processes, which can become brittle or unreliable due to aging or other factors.

One shortcoming of existing laminar hook systems is that such systems only serve to minimize distraction. Such systems, alone, are incapable of minimizing reduction of the intervertebral spacing. Additionally, laminar hook systems often include a flexible cord or cable. Such flexible cords, in certain situations, may actually serve to increase the reduction in the intervertebral spacing unless finely adjusted and/or loaded during implantation. Such fine adjustments can be deemed cumbersome and tedious by a surgeon. For example, in the system described above, the surgeon must first attach one hook upon an edge of a laminar region of a first vertebra, subsequently attach the second hook along an edge of a laminar region of a second vertebra, and finally adjust the tension in the interconnecting cord to insure the laminar hooks maintain engagement with the vertebra without, applying too great a compressive force that reduces the intervertebral spacing beyond a desired amount. Such steps in the surgery process require precision and accuracy and increase the time and cost of ultimately performing the operation.

Lastly, longitudinal rod systems, as mentioned above, require many components such as rods requiring alignment and screws that need to be threaded into vertebra during surgery. These systems are very cumbersome and expensive. Additionally, similar to the systems described above, such systems require ample precision and accuracy on the part of the surgeon, which ultimately increases operation time and cost.

SUMMARY OF THE INVENTION

In accordance with one form, a spinal stabilization system includes a first engagement member and support structure therefor. The first engagement member is adapted to be disposed between a first vertebra and a second vertebra. The engagement member generally includes a recess or saddle such as in the form of a generally concave seating surface configured for receiving at least a portion of a laminar region of the first vertebra. The support structure engages a portion of the second vertebra and assists in maintaining the engagement member in engagement with the first vertebra. The structural cooperation of the first engagement member and the support structure is such that the engagement member inhibits reduction of the intervertebral spacing between the first and second vertebrae.

One advantage of this form system is that it relies on and provides structural reinforcement at the laminar region of the vertebra. This is beneficial because the laminar region of the vertebra is disposed closer to the central axis of the spine than the narrow, projecting processes and other regions of the vertebra. This system avoids engaging and loading the spinous processes and, therefore, provides a sturdier system. Additionally, the stabilization system provides a reactive supporting force that is located closer to the central axis of the spine than prior interspinous support systems. This minimizes the chance of causing spinal misalignment due to the spinal stabilization system described herein. Additionally, the simple structure and arrangement of the spinal stabilization system reduces the amount of time required for surgery.

According to another form, the support structure of the spinal stabilization system includes a second engagement member having a seating surface configured to receive and supporting at least a portion of a laminar region of the second vertebra.

According to another form, the support structure of the spinal stabilization system includes a rod extending from the first engagement member and adapted to be fixed to a pedicle region of the second vertebra.

According to yet another form, the support structure of the spinal stabilization system includes a rod extending from the first engagement member and adapted to be fixed to a pedicle region of a third vertebra opposite the second vertebra from the first vertebra.

According to still another form, the support structure of the spinal stabilization system includes a biasing member disposed between first and second engagement members to provide a force distracting the first and second engagement members.

According to still another form, the support structure of the spinal stabilization system includes a biasing member that is an arch-shaped plate.

According to still yet another form, the biasing member includes a body formed of elastic material.

According to still yet another form, the support structure of the spinal stabilization system includes a tensioning member. The tensioning member is connected between the first and second engagement members and is adapted to provide a force distracting the first and second engagement members. Such distraction causes the seating surfaces to maintain engagement with the laminar regions of the first and second vertebra, respectively.

According to still yet another form, the spinal stabilization system further includes a tensioning member engaging at least one of a spinous process of the first vertebra and a spinous process of the second vertebra. Such a tensioning member provides a compressive force to the first and second spinous processes.

BRIEF DESCRIPTION OF THE DRAWINGS

FIG. 8 is a perspective view of a spinal stabilization system according to a fourth form of the present invention including a engagement member in abutting engagement with a laminar region of a first vertebra and a rod having opposing leg portions extending from the engagement member and fixedly attached to opposing pedicle regions of a third vertebra;

FIG. 9 is an enlarged perspective view of the spinal stabilization system of FIG. 8 showing a transverse bore extending through the engagement member and receiving the rod;

FIG. 66 is a perspective view of a spinal stabilization system according to a twentieth form of the present invention including a butterfly laminar spacer;

FIG. 67 is an elevational view of the butterfly laminar spacer of FIG. 66;

FIG. 68 is a perspective view of the butterfly laminar spacer of FIG. 66 shown in a partial cutaway view to illustrated a pivot joint including a ball and socket configuration;

DETAILED DESCRIPTION OF THE PREFERRED EMBODIMENTS

Figure 40:
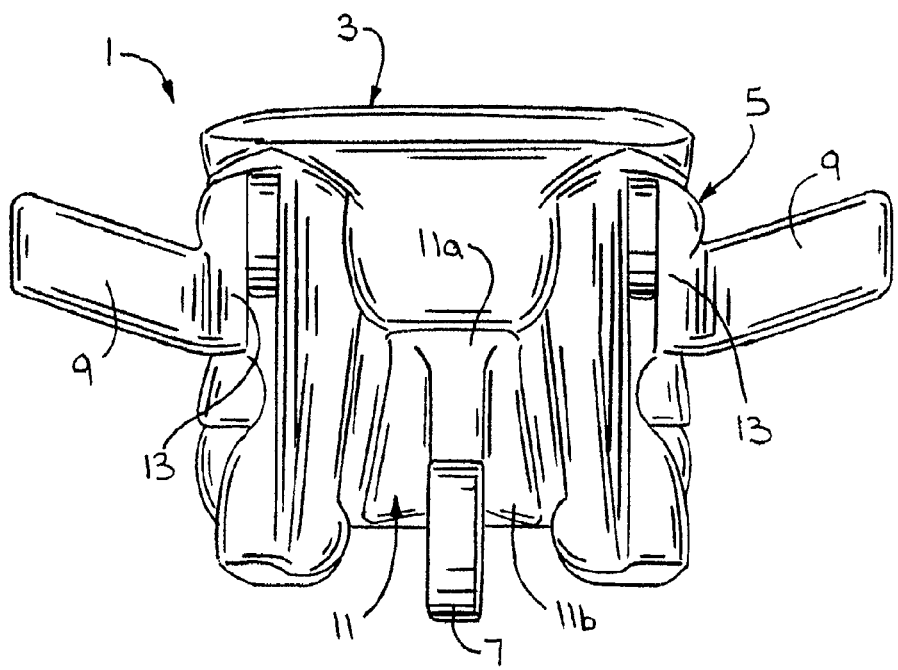
FIG. 40 is a posterior perspective view of a vertebra of a spine showing the spinous process, the transverse processes, the laminar region, and the pedicle regions.
Figure 41:
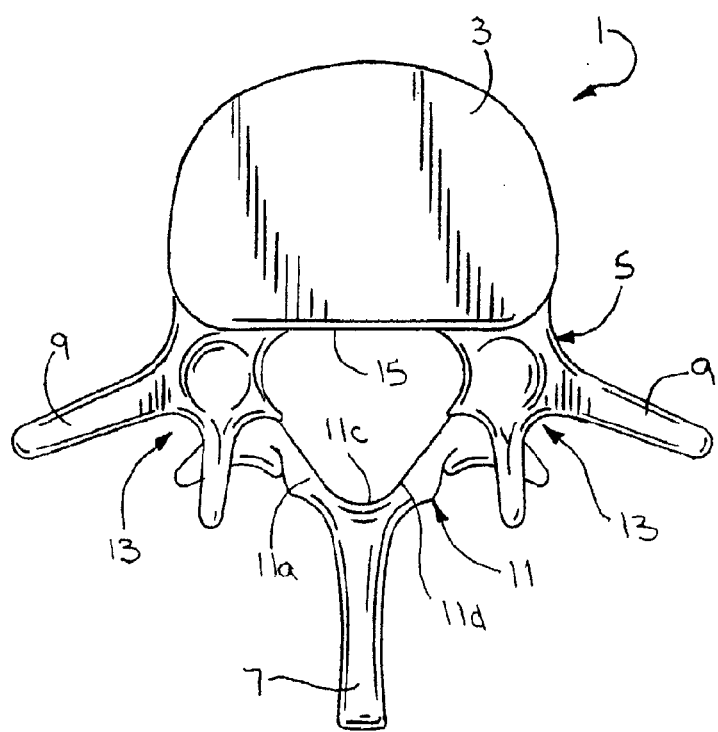
FIG. 41 is a superior view of a vertebra of a spine showing the body, the spinous process, the transverse processes, and the vertebral foramen.
Figure 42:
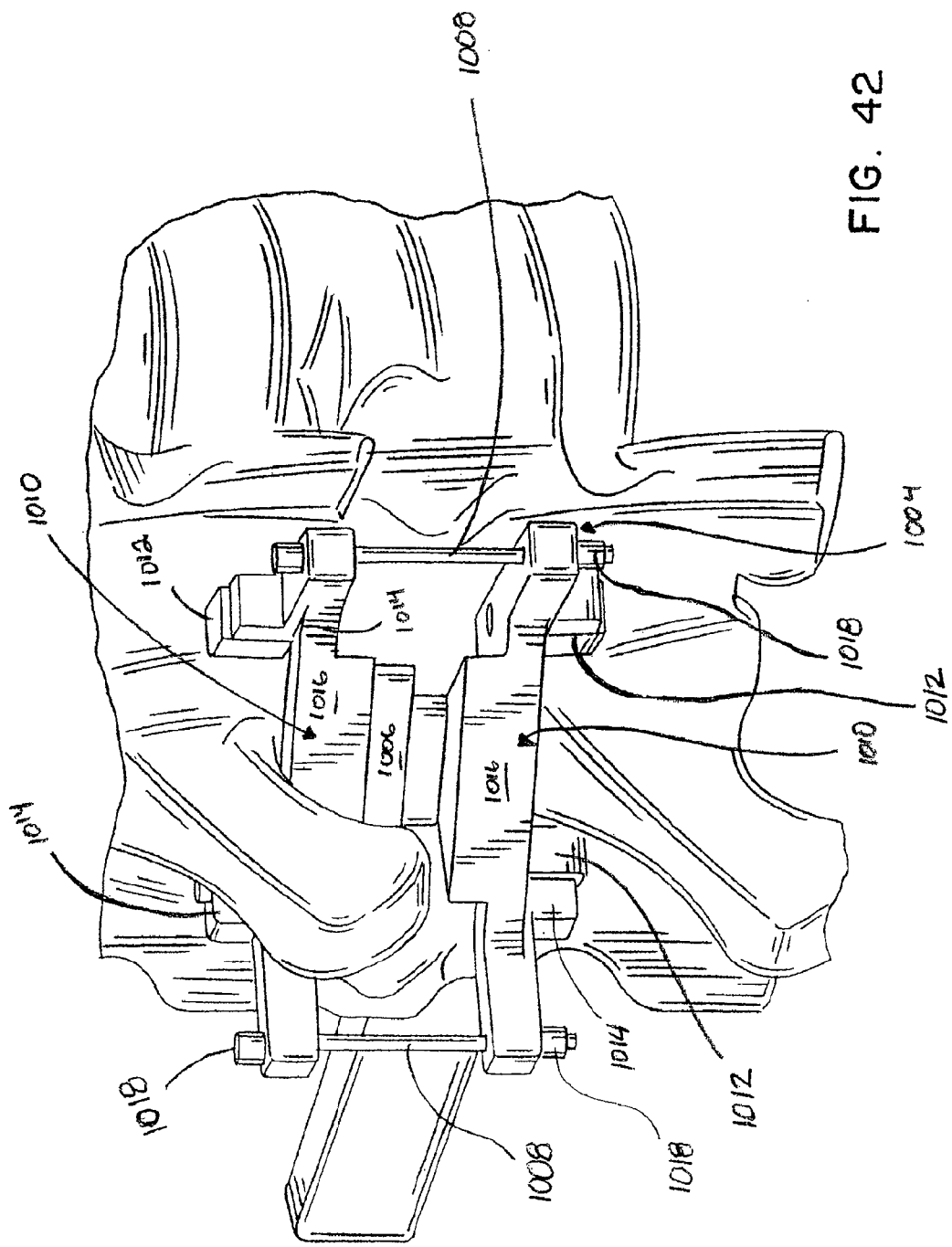
FIG. 42 is another perspective view of the spinal stabilization system of FIGS. 26 through 28.
Figure 43:
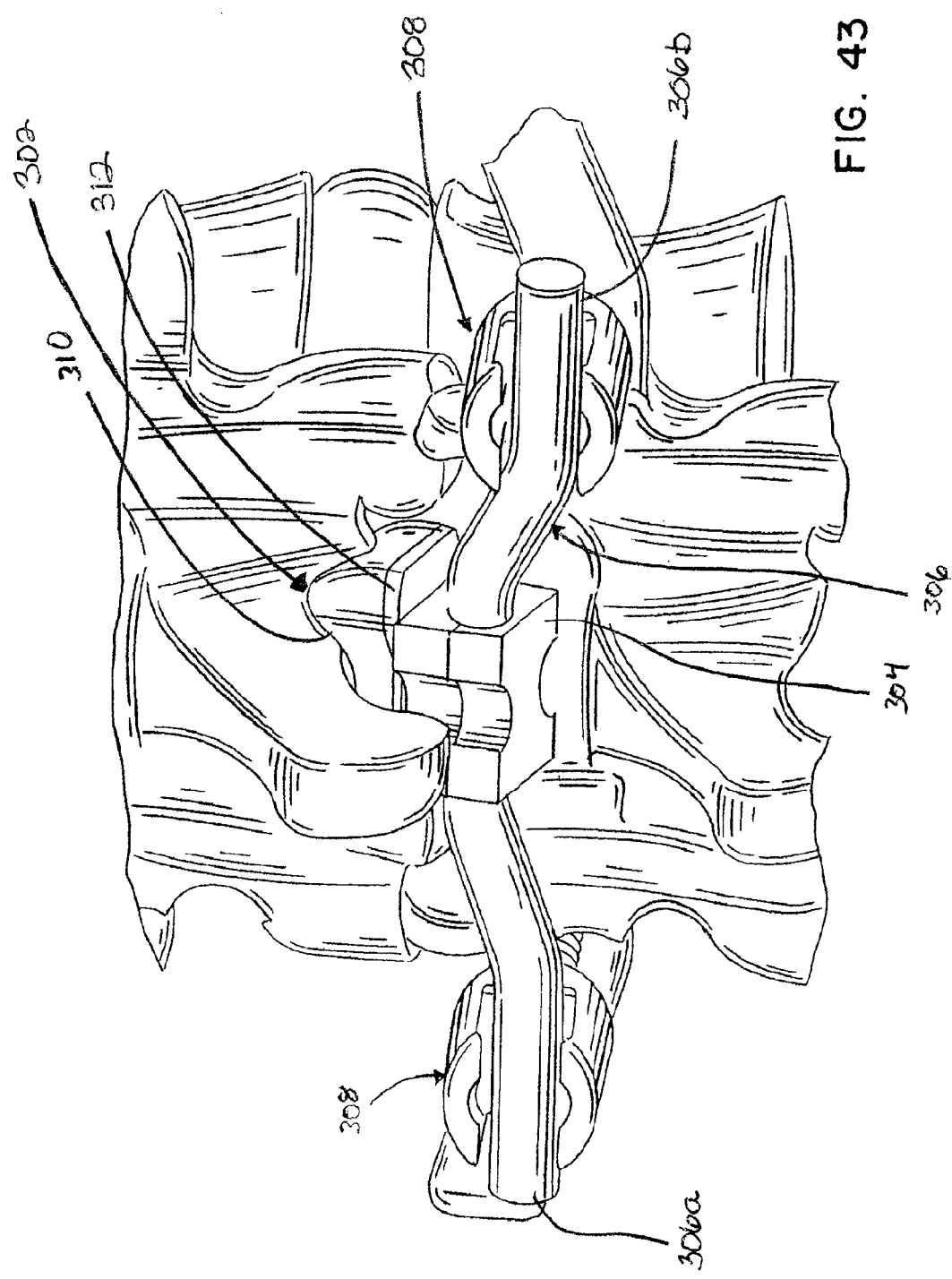
FIG. 43 is another perspective view of the spinal stabilization system of FIGS. 4 through 7.
Figure 44:
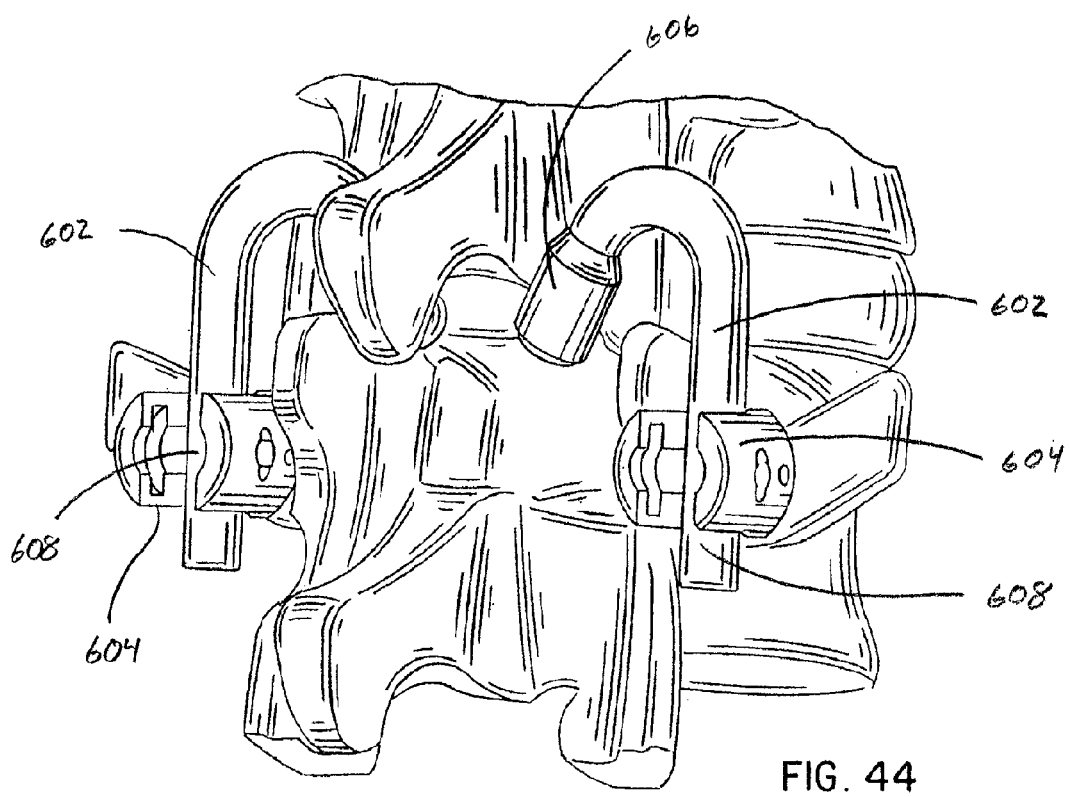
FIG. 44 is another perspective view of the spinal stabilization system of FIGS. 14 through 16.
Figure 45:
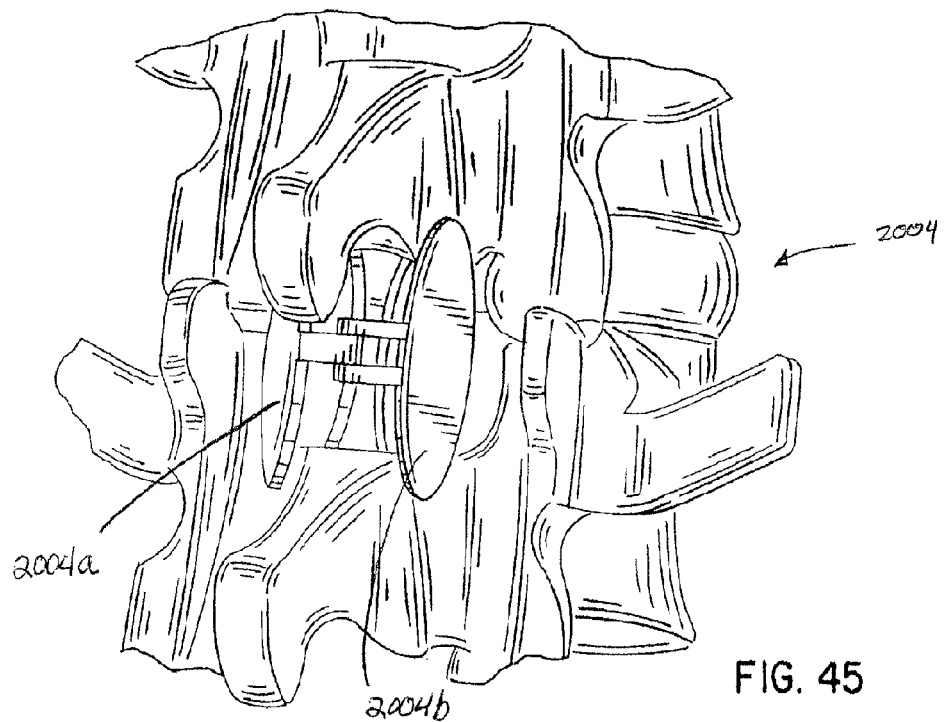
FIG. 45 is another perspective view of spinal stabilization system of FIGS. 66-69.
Figure 46:
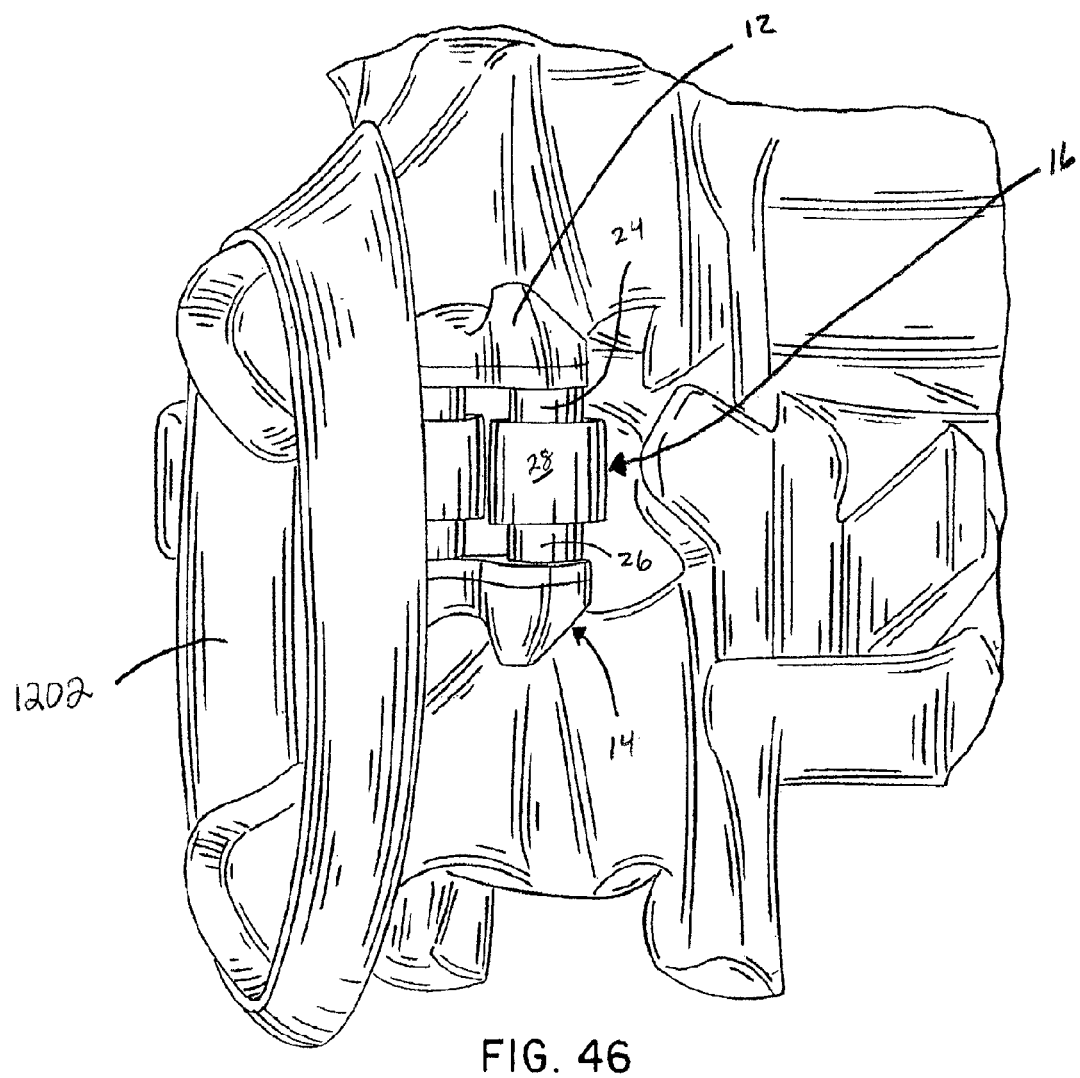
FIG. 46 is another perspective view of the spinal stabilization system of FIGS. 1 and 2 supplemented with an optional axial retention member.

Generally, the present invention provides a spinal stabilization system for supporting at least one vertebra of a spine and, more particularly, a laminar region of at least one vertebra. Referring briefly to FIGS. 40 and 41, a vertebra 1 of a spine generally includes a body 3 and a vertebral arch 5 defining a vertebral foramen 15. The vertebral arch 5 includes a spinous process 7, a pair of transverse processes 9, a laminar region 11, and pedicle regions 13. The spinous process 7 extends generally directly posterior to the body 3 opposite the vertebral foramen 15. The laminar region 11 is disposed directly behind the spinous process 7 and extends between and interconnects the spinous process 7 to the transverse processes 9. The transverse processes 9, therefore, extend generally laterally from the laminar region 11 on each side of the spinous process 7. The pedicle regions 13 are disposed between and interconnect the transverse processes 9 and, therefore, the entire vertebral arch 5 to the body 3. As depicted, the laminar region 11 is a generally arch-shaped wall including a superior edge 11a, an inferior edge 11b, an anterior surface 11c and a posterior surface 11d. A system in accordance with the principles of the present invention provides support substantially near the central longitudinal axis L of the spine by engaging the superior and inferior edges 11a, 11b of the laminar regions 11 of adjacent vertebrae 1, thereby minimizing the possibility of spinal misalignment caused by the system. Multiple variations and examples of the present invention will now be described herein with direct reference to the drawings.

Figure 1:
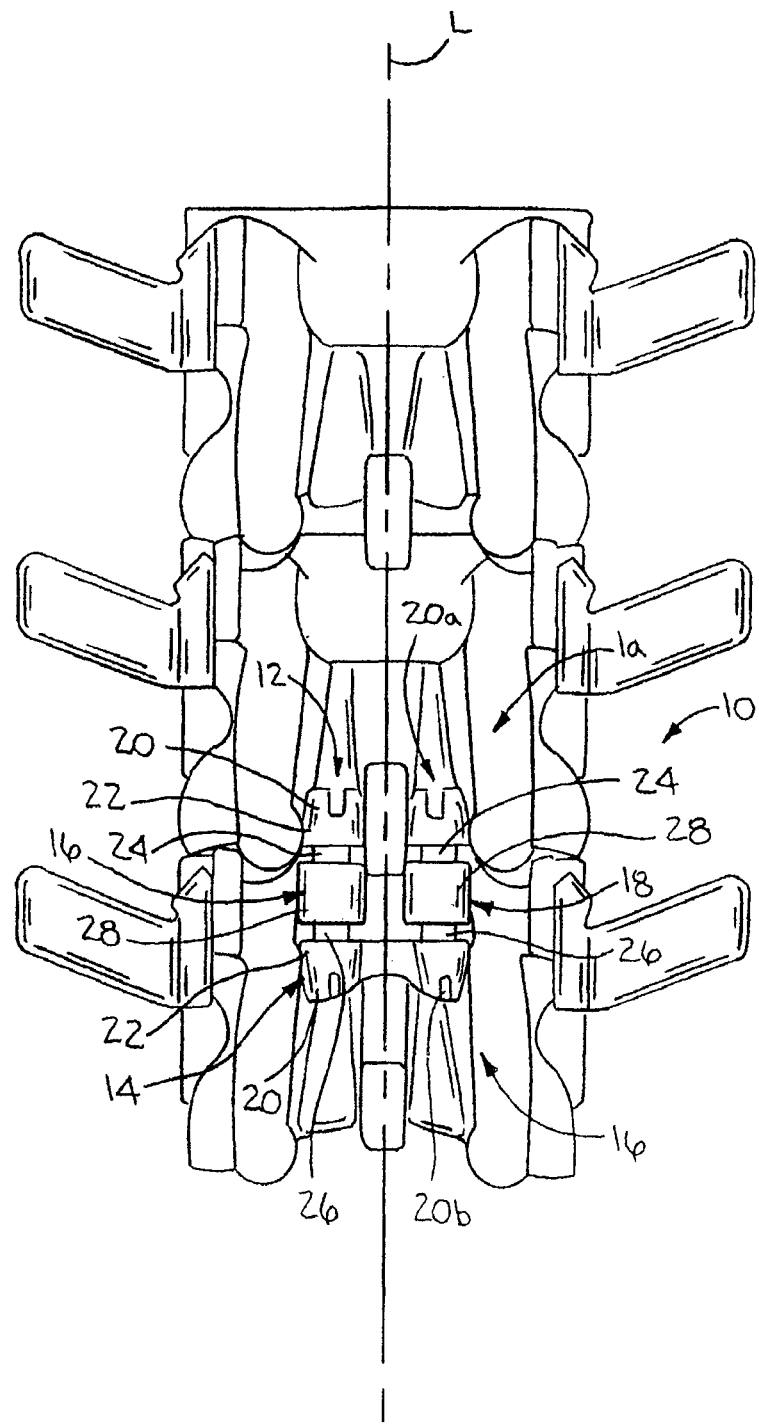
FIG. 1 is a perspective view of a spinal stabilization system according to a first form of the present invention implanted between adjacent vertebrae including a first engagement member and a second engagement member in abutting engagement with respective laminar regions of the adjacent vertebrae.
Figure 2:
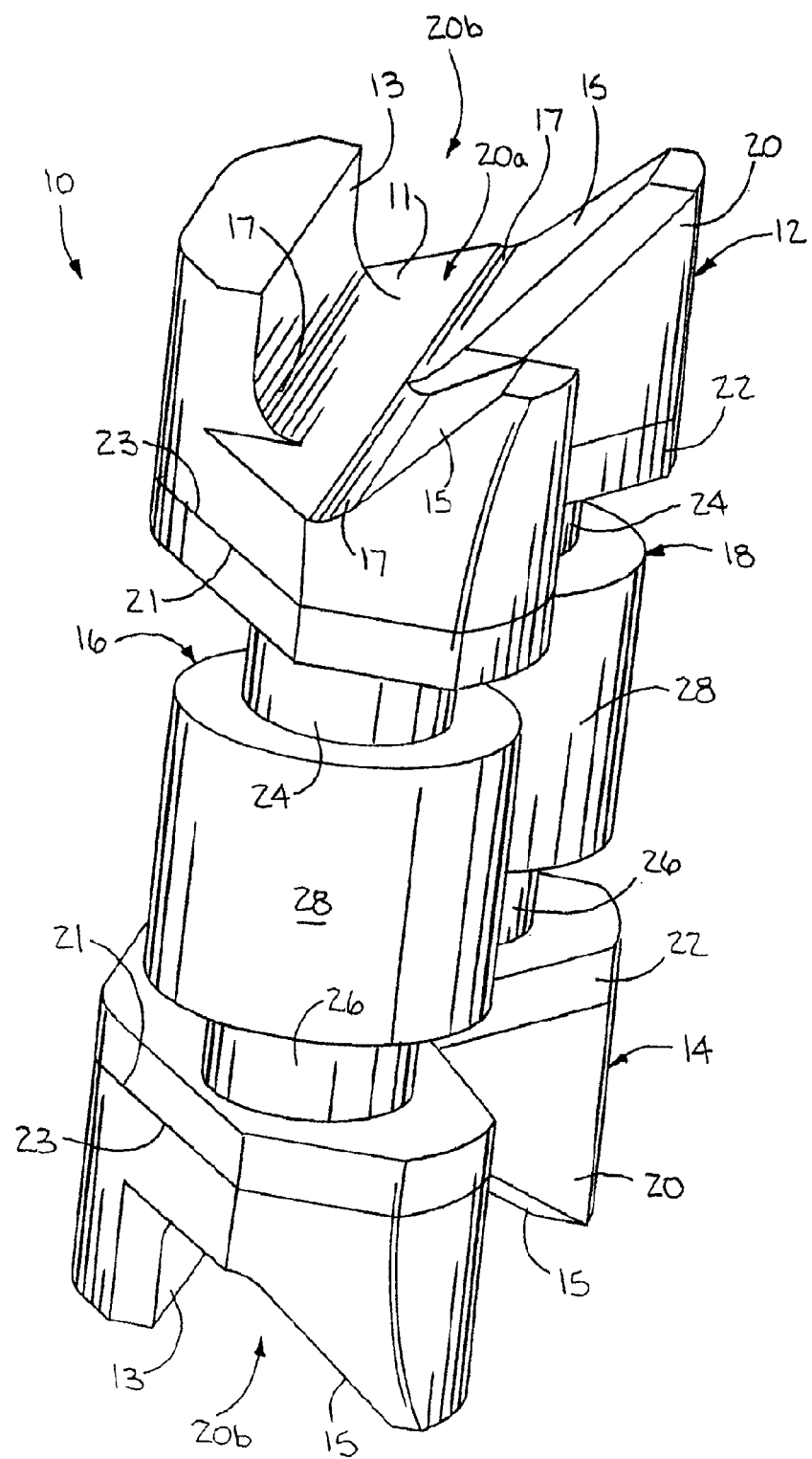
FIG. 2 is an enlarged perspective view of the spinal stabilization system of FIG. 1 showing a complex concave seating surface of the first engagement member including a substantially vertical anterior surface and a pair of angled posterior surfaces adapted to receive a laminar region of a vertebra.

FIGS. 1 and 2 depict a spinal stabilization device 10 according to a first form of the present invention. The spinal stabilization device 10 includes a first engagement member 12, a second engagement member 14, and a support structure including a first support structure 16, and a second support structure 18. As is illustrated in FIG. 1, the spinal stabilization device 10 is interposed between the laminar regions 11 of adjacent vertebrae 1a, 1b. Specifically, the first engagement member 12 engages the inferior edge 11b of the laminar region 11 of the superior vertebra 1a and the second engagement member engages a superior edge 11a of a laminar region 11 of the inferior vertebra 1b, while the support structures 16 and 18 provide axial support therebetween. Thus, the spinal stabilization device 10 counteracts any compressive loads applied to the adjacent vertebrae to maintain an appropriate intervertebral spacing therebetween. Specifically, the compressive loads are transferred from one of the superior and inferior vertebra 1a, 1b through the spinal stabilization system 10 to the other of the superior and inferior vertebra 1a, 1b. The semi-rigid construction of the spinal stabilization system 10, which will be described below, therefore acts as a crutch, stilt or resilient spacer between the vertebrae 1a, 1b. Further structural details of the spinal stabilization device 10 will now be described.

The first and second engagement members 12, 14 each include a saddle member 20 and a base plate 22. Each of the first and second support structures, 16, 18 include an upper support post 24 and a lower support post 26 interposed by a damper 28. In one form, the upper and lower support posts 24 of the respective first and second support structures 16, 18 are integrally formed stainless steel members projecting axially from the corresponding base plates 22 of the first and second engagement members 12, 14. In another form, the upper and lower support posts 24, 26, are formed independent of the base plates 22 and subsequently attached thereto via a fastener such as a threaded bolt, a rivet, or some other means such as welding or soldering. In another form, the upper and lower support posts 24, 26 are integrally combined as a single post.

The saddle members 20 of the first and second engagement members 12, 14 each include a seating surface 20a. The seating surfaces 20a are complex concave surfaces configured to receive the edges 11a, 11b of the laminar regions 11 of the vertebrae 1a, 1b and maintain the relative disposition of the vertebrae 1a, 1b and the spinal stabilization device 10, as illustrated in FIG. 1. Referring specifically to FIG. 2, each of the seating surfaces 20a includes a bottom surface 11, an anterior surface 13 that extends substantially perpendicularly from the bottom surface 11, and a pair of posterior surfaces 15 that extend at an angle or an incline from the bottom surface 11. Each of the anterior and posterior surfaces 13, 15 transitions into the bottom surface 11 via a rounded corner surface 17, which lends to the natural curvature of the laminar regions 11 of the vertebrae. The bottom surface 11 engages an edge 11a, 11b of the laminar region 11 of the corresponding inferior or superior vertebra 1a, 1b to minimize axial shifting of the spinal stabilization device 10 as well as provide axial support between the vertebrae. The substantially vertical anterior surfaces 13 engage the anterior surface 11c of the laminar regions 11 of the corresponding vertebrae to minimize shifting of the spinal stabilization device 10 in the anterior direction. The angled posterior surfaces 15 engage the posterior surface 11d of the laminar regions 11 of the corresponding vertebrae to minimize shifting of the spinal stabilization device 10 in the posterior direction.

While the seating surfaces 20a have been immediately disclosed and described as including a substantially vertical anterior surface and a plurality of angled posterior surfaces spaced by a central gap 20b, an alternate form may include a plurality of anterior surfaces and a single posterior surface or pluralities of both the anterior and posterior surfaces. Furthermore, in another alternate form, the seating surface 20a may contain a single smooth surface similar to that of a true saddle or any other geometrical shape configured to serve the principles of the invention.

Additionally, each of the saddle members 20 includes a generally flat surface 21 located opposite the seating surfaces 20a. The generally flat surfaces are adjoined with generally flat surfaces 23 of the base plates 22 of the corresponding engagement members 12, 14. In one form, the flat surfaces of the saddle members 20 may be secured to the base plates 22 via an adhesive, with fasteners, or some other means. In another form, the saddle members 20 and the base plates 22 may be integrally formed as a single member. Additionally, it should be appreciated that while the seating surfaces 20a of the saddle members 20 have been described herein as being concave, an alternate form may not be concave, but rather flat or bulbous and formed of a relatively deformable material easily compressed to deform about the laminar regions 11 of the vertebrae 1 engaged therewith.

The dampers 28 of the first and second support structures 16, 18 are substantially cylindrical deformable members disposed axially between the upper support posts 24 and the lower support posts 26. In one form, the dampers 28 are constructed of a substantially resilient elastic material, such as rubber, foam, a polymer, a co-polymer or any other material suitable for the purposes described herein. So constructed, the dampers 28 serve to bias the first and second engagement members 12, 14 away from each other, as well as absorb compressive loads applied to the first and second engagement members 12, 14 by the opposing vertebrae. Furthermore, in a preferred form, the dampers 28 include internal cavities or pockets (not shown) for receiving portions of the upper and lower support posts 24, 26 therein. In another form, the dampers 28 do not include pockets, but rather include flat engagement surfaces adhered to the corresponding ends of the support posts 24, 26. In still another form, the support posts 24, 26 and the dampers 28 may be envisioned to be constructed as a single unitary member of deformable or non-deformable material.

Accordingly, it should be appreciated that during operation, the spinal stabilization device 10 is preferably provided to a surgeon preassembled. In other words, all of the above-described components are operably connected to form a single unit for ease of use and application purposes. When the surgeon is prepared to implant the spinal stabilization system 10 into the intervertebral space, they need only to push the first and second engagement members 12, 14 toward each other to reduce the overall axial height of the device 10. Upon inserting the system 10 between adjacent vertebrae, the surgeon may release the compressive force allowing the dampers 28 to decompress and cause the seating surfaces 20a of the saddle members 20 to closely fit against the surfaces of the laminar regions 11 of the opposing vertebrae 1a, 1b. It should be appreciated that the surgeon may compress the spinal stabilization system 10 with their hands, a tool such as pliers or a clamp, or by any other means suitable for the situation. Additionally, it should be appreciated that instead of having to compress the entire spinal stabilization system 10, in another form, the surgeon may receive the components of the system 10 disassembled and may assemble them in the intervertebral space during the operation. In yet another form, instead of compressing or assembling the device, the surgeon may spread the vertebrae prior to implantation.

Figure 3:
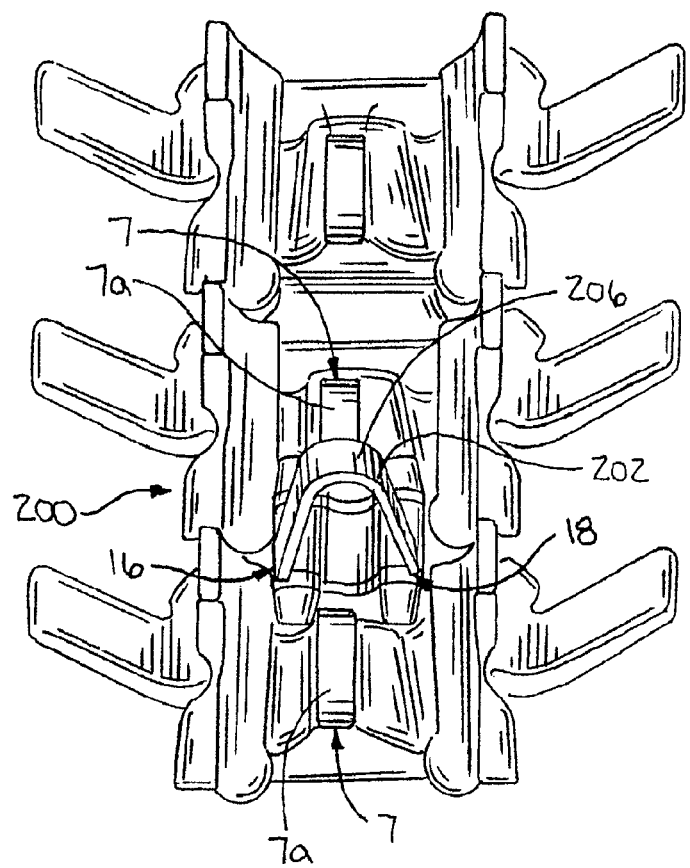
FIG. 3 is perspective view of a spinal stabilization system according to a second form of the present invention implanted between adjacent vertebrae and including a first engagement member in abutting engagement with a laminar region of a first vertebra, a second engagement member in abutting engagement with a laminar region of a second vertebra, and a retention member extending substantially transverse thereto.
Figure 3A:
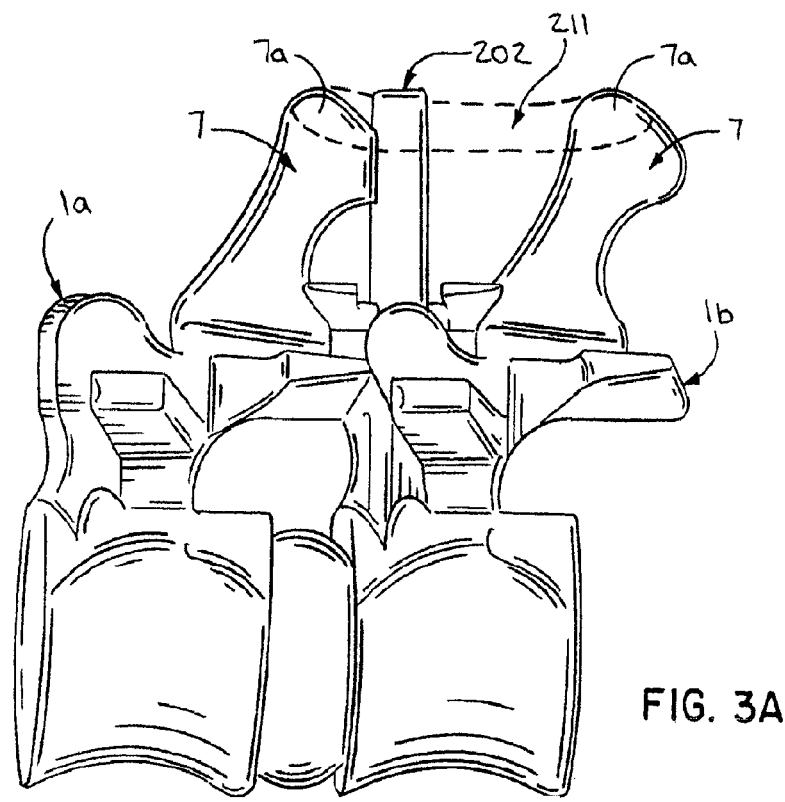
FIG. 3A is a side view of the spinal stabilization system of FIG. 3 implanted between adjacent vertebrae and showing a retention member extending around an interspinous ligament.

FIG. 3 depicts a spinal stabilization device 200 according to a second form of the present invention. Specifically, the spinal stabilization device 200 is very similar to the spinal stabilization device 10 depicted in FIGS. 1 and 2, but for a distinct construction regarding the first and second support structures 16, 18. The spinal stabilization device 200 includes a retention member 202 including collar portions 204 similar to dampers 28. Therefore, the spinal stabilization device 200 functions to minimize reduction in the intervertebral spacing in a way identical to spinal stabilization device 10. Additionally, however, the retention member 202 of the spinal stabilization device 200 extends around an interspinous ligament 211 shown in FIG. 3A. The retention member 202 therefore serves to restrict anterior displacement of the spinal stabilization device 200 by anchoring it on the interspinous ligament 211.

The retention member 202 of the spinal stabilization device 200 includes opposing collar portions 204 and a laterally extending portion 206. The collar portions 204 are cylindrical members similar in structure to the dampers 28 depicted in FIGS. 1 and 2 and, as stated above, serve a generally similar purpose; therefore, they will not be described in detail herein again. The laterally extending portion 206, however, includes a generally V-shaped member extending posterior or rearward of the first and second support structures 16, 18.

FIGS. 4-7 depict a spinal stabilization system 300 according to a third form of the present invention. The spinal stabilization system 300 includes an engagement member 302, and support structure including a bracket 304, a rod 306, and a pair of fixation devices 308. The engagement member 302 engages the inferior edge 11b of the laminar region 11 of the superior vertebra 1a, while the fixation devices 308 secure the system 300 to the pedicle regions 13 of the inferior vertebra 1b. The rod 306 therefore interconnects the various components of the system 300 and enables it to minimize reduction of the intervertebral spacing between the inferior and superior vertebrae 1a, 1b by counteracting compressive loads applied to the spine. Specifically, a compressive load applied to either or both of the superior and inferior vertebrae 1a, 1b is transferred directly to the engagement member 302 and the fixation devices 308. Such a compressive load operated to load the rod 306 in bending. The rod 306 is substantially rigid so as to counteract this bending load to maintain the intervertebral spacing.

Figure 7:
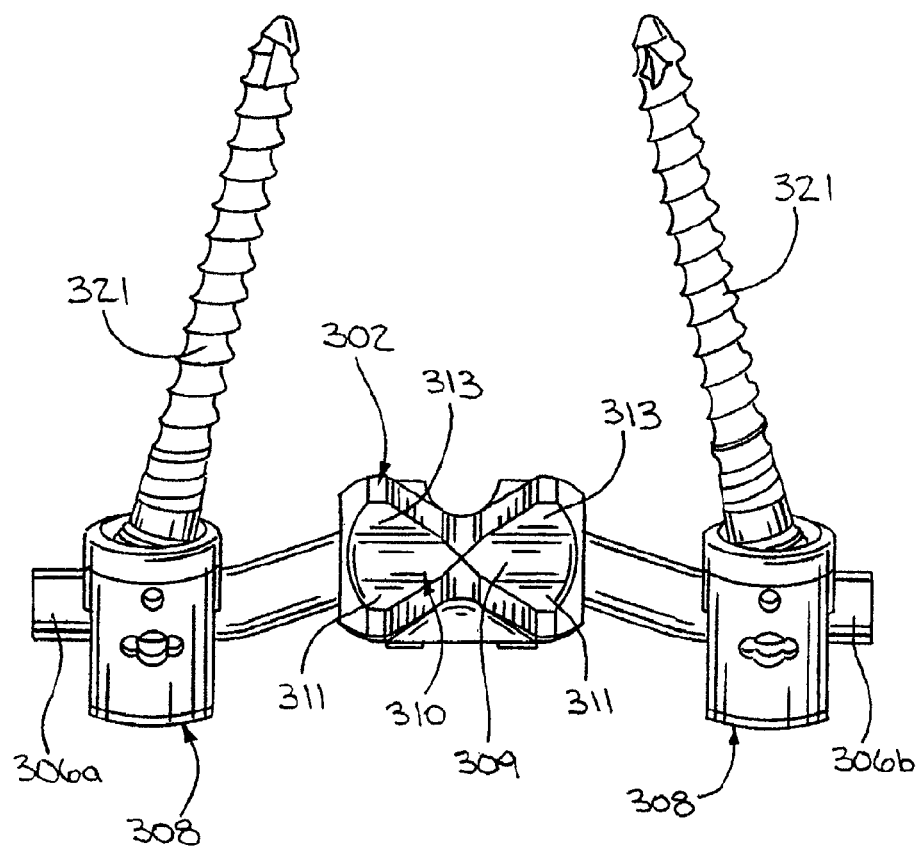
FIG. 7 is another perspective view of the spinal stabilization system of FIGS. 4 and 5 showing a complex concave seating surface of the engagement member including a pair of angled anterior surfaces and pair of angled posterior surfaces adapted to receive a laminar region of a vertebra.

The engagement member 302 is similar to the engagement members 12, 14 depicted and described above with reference to FIGS. 1 and 2 and includes a saddle member 310 and a base plate 312. The saddle member 310, however, includes a slightly different concave seating surface 310a, as depicted in FIG. 7. Specifically, the seating surface 310a includes a substantially flat bottom surface 309, a pair of angled or inclined posterior surfaces 311, and a pair of angled or inclined anterior surfaces 313 across from corresponding surfaces 311. Similar to the seating surface described above with reference to FIGS. 1 and 2, the bottom surface 309 engages an inferior edge 11b of a laminar region 11 of the superior vertebra 1a to provide axial support to the superior vertebra 1a. Additionally, the anterior surfaces 313 at least partially engage the anterior surface 11c of the laminar region 11 of the superior vertebra 1a to generally minimize shifting of the device 300 the posterior direction. The posterior surfaces 311 at least partially engage the posterior surface 11d of the laminar region 11 of the superior vertebra 1a to minimize shifting of the spinal stabilization device 300 in the anterior direction.

Figure 4:
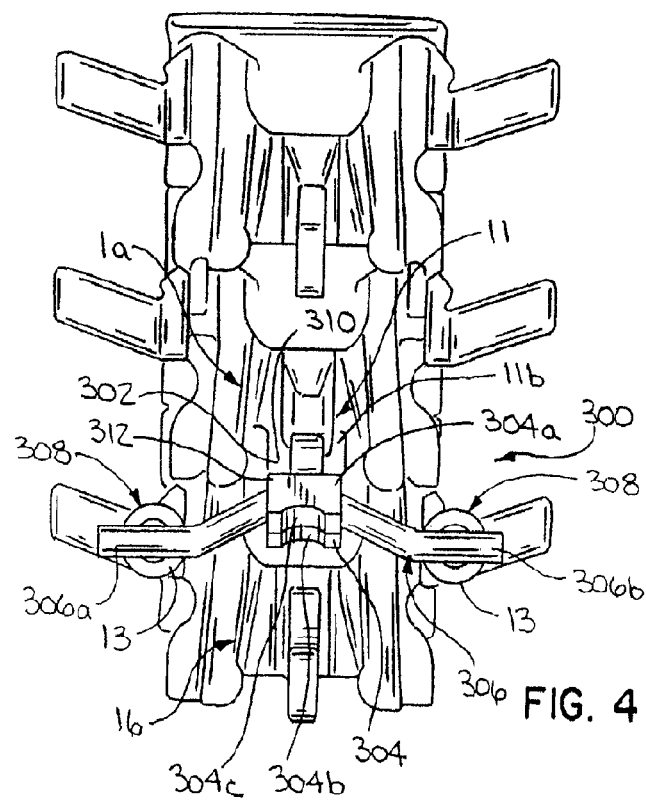
FIG. 4 is a perspective view of a spinal stabilization system according to a third form of the present invention implanted between adjacent vertebrae including an engagement member in abutting engagement with a laminar region of a first vertebra and a rod extending between and affixed to pedicle regions of a second vertebra.
Figure 5:
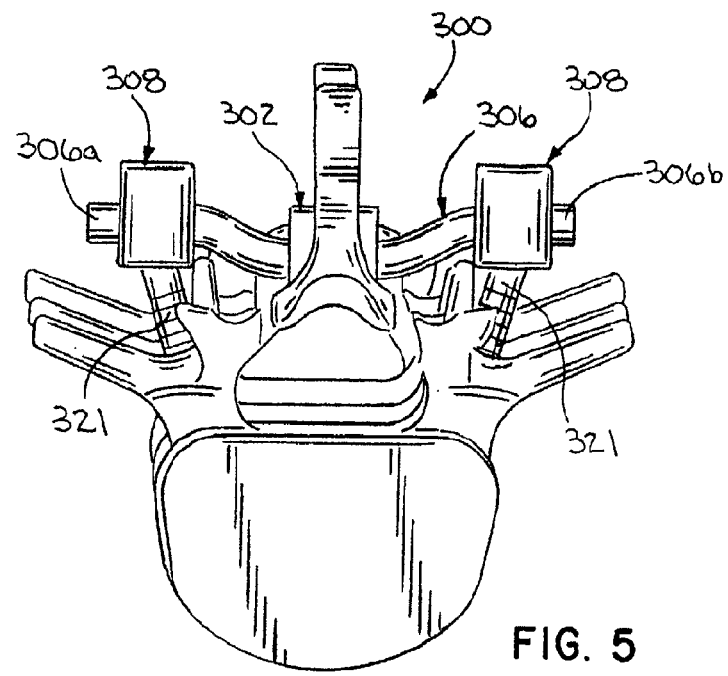
FIG. 5 is another perspective view of the spinal stabilization system according to the third form of the present invention depicted in FIG. 4.
Figure 6:
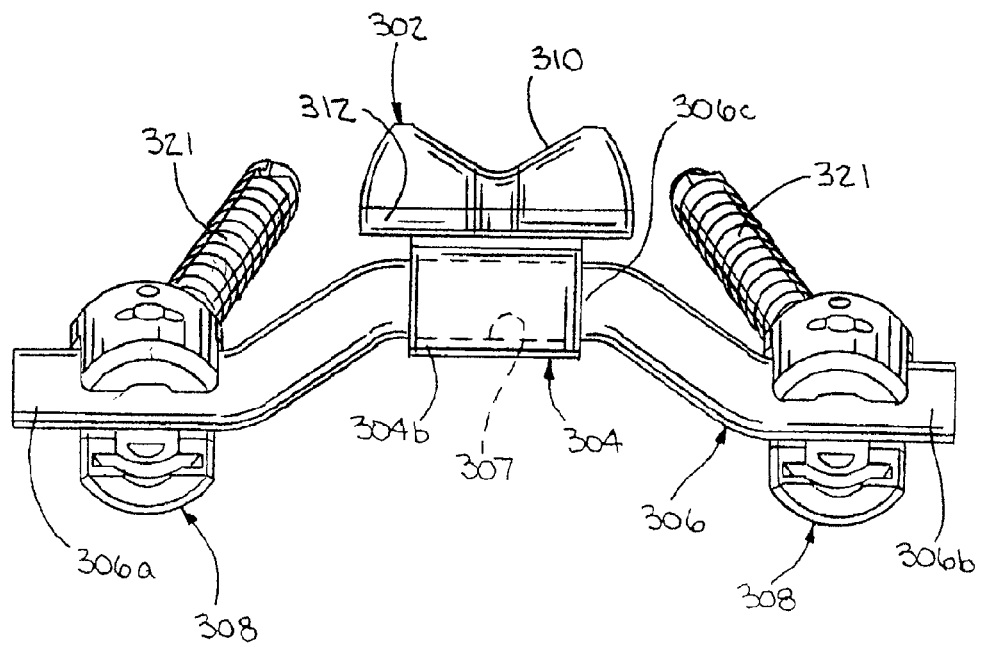
FIG. 6 is an enlarged perspective view of the spinal stabilization system of FIGS. 4 and 5 showing a transverse bore extending through the engagement member and receiving the rod.

The bracket 304 is a generally rigid structure including a pair of cooperating upper and lower members 304a, 304b connected to define a lateral bore 307 therethrough. The rod 306 includes first and second opposite ends 306a, 306b fixedly attached to the pair of fixation devices 308. The fixation devices 308, in one form, include pedicle screw assemblies such as described in applicant's assignee's copending U.S. patent application Ser. Nos. 10/358,530 and 10/549,873, which are incorporated as if reproduced in their entirety herein. Similar to the engagement members 12, 14 depicted and described with reference to FIGS. 1 and 2, the engagement member 302 abuttingly engages the inferior or lower edge 11b of the laminar region 11 of the superior or upper vertebrae 1a, as illustrated in FIG. 4. Specifically, the seating surface 310a of the saddle member 310 is contoured and configured to receive the inferior edge 11b of the laminar region 11 of the superior vertebra 1a. The base plate 312 of the engagement member 302 fixedly attaches to an upper surface of the bracket 304. In one form, this attachment is provided via an adhesive, a weld, or some other suitable means. In alternative embodiments, it is envisioned that this attachment may be accomplished via a fastener such as a threaded fastener, a rivet, or some other device capable of serving the principles of the present invention.

As stated above, the rod 306 has ends 306a, 306b, as well as a mid-region 306c. The opposite ends 306a, 306b are substantially aligned. The mid-region 306c is laterally offset from and generally parallel to the first and second ends 306a, 306b. The mid-region 306c of the rod 306 is disposed in and extends through the lateral bore 307 of the bracket 304. In one form, as stated above, the bracket 304 includes a pair of connected members 304a, 304b each having complementary arcuate recesses that cooperate to form the through bore 307 for receiving the mid-region 306c of the rod 306 and, additionally, threaded fasteners such as screws for fixing the bracket members together and tightly clamping the rod 306 in the bore 307. In another form, a set-screw may be provided with the bracket 304 to securable fix the location of the rod 306 relative thereto. In yet another form, it is envisioned that the rod 306 is not fixedly attached to the bracket 304, and therefore, may move laterally and/or rotatably relative thereto. The pair of fixation devices 308 includes yoke structures enabling the securing of the first and second ends of the rod 306a, 306b to the pedicle regions of the lower vertebra of FIG. 4. In one form, as stated above, the fixation devices 308 include pedicle screws or bone screws 321 that threadingly engage directly with the pedicle regions 13 of the inferior vertebra 1b of FIGS. 4 and 5.

So configured, the spinal stabilization system 300 of FIGS. 4-7 limits reduction of the intervertebral spacing. During surgery, first, a surgeon may locate and attach the fixation devices 308 to the pedicle regions of the inferior vertebra 1b. Then, the surgeon may position the engagement member 302 including the bracket 304 adjacent the inferior edge 11b of the laminar region 11 of the superior vertebra 1a such that it is seated against the seating surface 310a of the saddle member 310. The surgeon then may align the first and second ends 306a, 306b of the rod 306 with the fixation devices 308 and fixedly attach them thereto.

Figure 10:
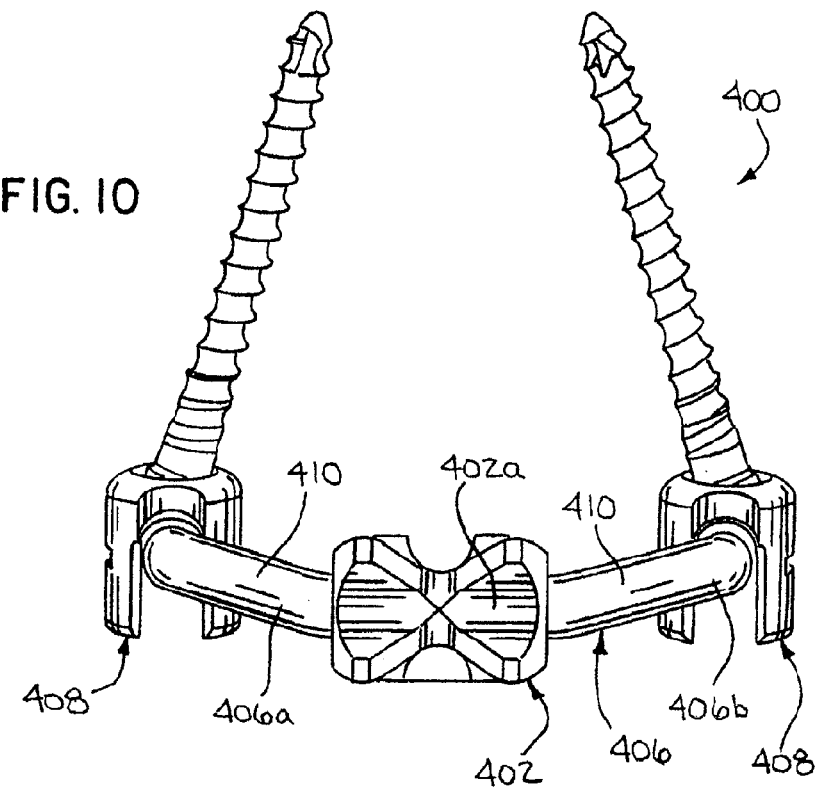
FIG. 10 is another perspective view of the spinal stabilization system of FIG. 8 showing a complex concave seating surface of the engagement member including a pair of angled anterior surfaces and pair of angled posterior surfaces adapted to receive a laminar region of a vertebra.

FIGS. 8-10 depict a stabilization system 400 according to a fourth form of the present invention. Similar to the spinal stabilization device 300 depicted in FIGS. 4-7, the spinal stabilization system 400 depicted includes an engagement member 402, and a support structure having a bracket 404, a rod 406, and a pair of fixation devices 308. Unlike the spinal stabilization system discussed above, spinal stabilization system 400 operates to minimize reduction of intervertebral spacing between three vertebrae 1a, 1b, 1c. Specifically, the engagement member 402 engages the most superior or first vertebra 1a and the fixation devices 308 secure the system 400 to a most inferior or third vertebra 1c, thereby spanning a middle or second vertebra 1b. Thus, the spinal stabilization system 400 effectively operates similar to the forms described above in that it counteracts compressive loads applied to the spine, but it does so along a greater portion of the spine. Specifically, a compressive load applied to one or more of the vertebrae 1a, 1b, 1c is directly transferred to the engagement member 402 as well as the fixation devices 408. Such a compressive load operates to load the rod 406 partially in bending and partially in compression. The substantially rigid rod 406, therefore, counteracts the bending and compressive loads to maintain the intervertebral spacing.

The rod 406 of the spinal stabilization system 400 of FIGS. 8-10 includes a first leg portion 406a and a second leg portion 406b interposed by a mid-region 406c. The mid-region 406c is disposed within a transverse bore 407 defined through the bracket 404. Additionally, as depicted in FIG. 10, the engagement member 402 includes a seating surface 402a that is structurally and functionally identical to that described above with reference to the seating surface 310a depicted in FIG. 7.

The first and second leg portions 406a, 406b each include an angularly or obliquely extending region 410 and a longitudinally extending region 412 relative to the spinal axis. FIG. 8 shows the rod 406 shaped to have a downwardly opening modified V or U configuration including bent leg portions 406a, 406b of the rod 406 that provide a longitudinal dimension to the spinal stabilization system 400 that is much greater than that of the spinal stabilization system 300 depicted in FIGS. 4-7. More specifically, as depicted, the leg portions 406a, 406b span an entire vertebra. Hence, the engagement member 402 of the spinal stabilization system 400 engages the inferior edge 11b of a laminar region 11 of the first vertebra 1a. Additionally, the fixation devices 408 of the spinal stabilization system 400 are fixably attached to pedicle regions 13 of the third vertebra 1c. Accordingly, the second vertebra 1b, which is located between the first and third vertebrae 1a, 1c is spanned by the spinal stabilization system 400.

While the illustrated form of the system spans a single vertebra, it may alternatively be designed or implemented to span more than one vertebra. Additionally, this form of the invention may further alternatively be implemented to not span an entire vertebra, but rather assume a similar configuration to that depicted in FIGS. 4-7 with a slightly different configuration of the rod 406. To achieve such a configuration, a slightly different thickness or diameter rod 406 may be required. The spinal stabilization system 400 would be assembled and implanted during a surgical operation in a manner very similar to the spinal stabilization system 300 described above.

Figure 11:
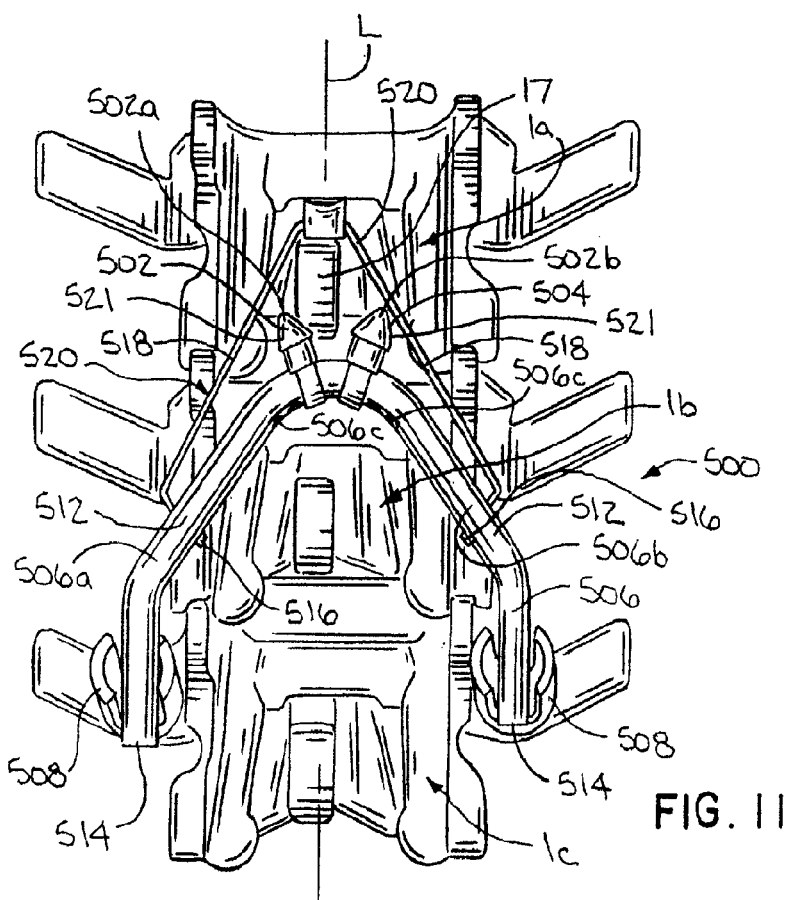
FIG. 11 is a perspective view of a spinal stabilization system according to a fifth form of the present invention including a pair of engagement members in abutting engagement with a laminar region of a first vertebra, a rod a having opposing leg portions extending from the engagement members and fixedly attached to opposing pedicle regions of a third vertebra, and an axial retention member extending from the rod around a spinous process of the first vertebra.
Figure 12:
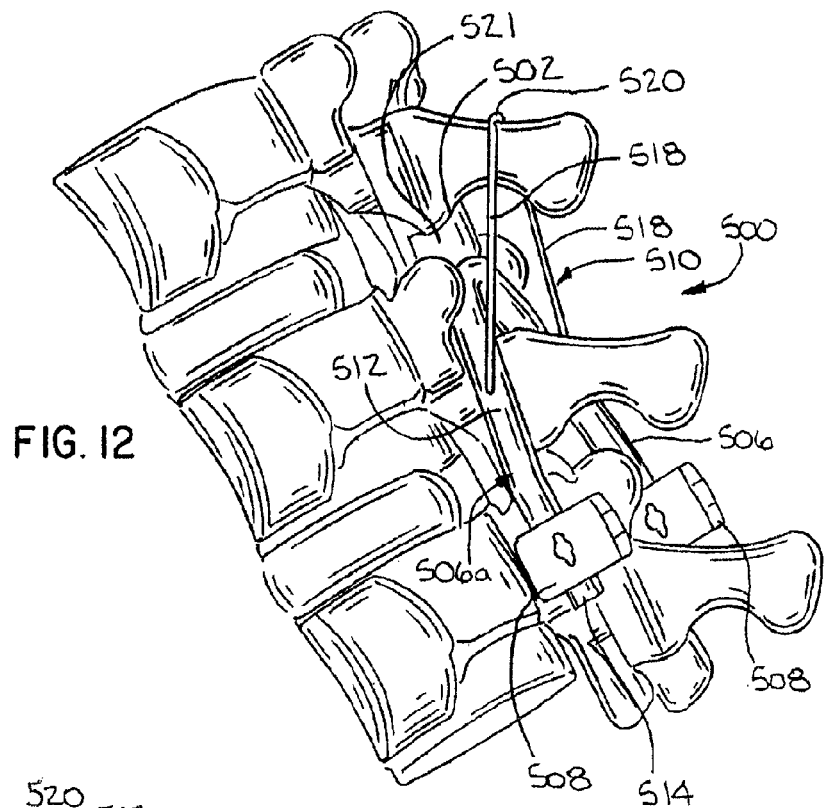
FIG. 12 is another perspective view of the spinal stabilization system according to the fifth form of the present invention depicted in FIG. 11.
Figure 13:
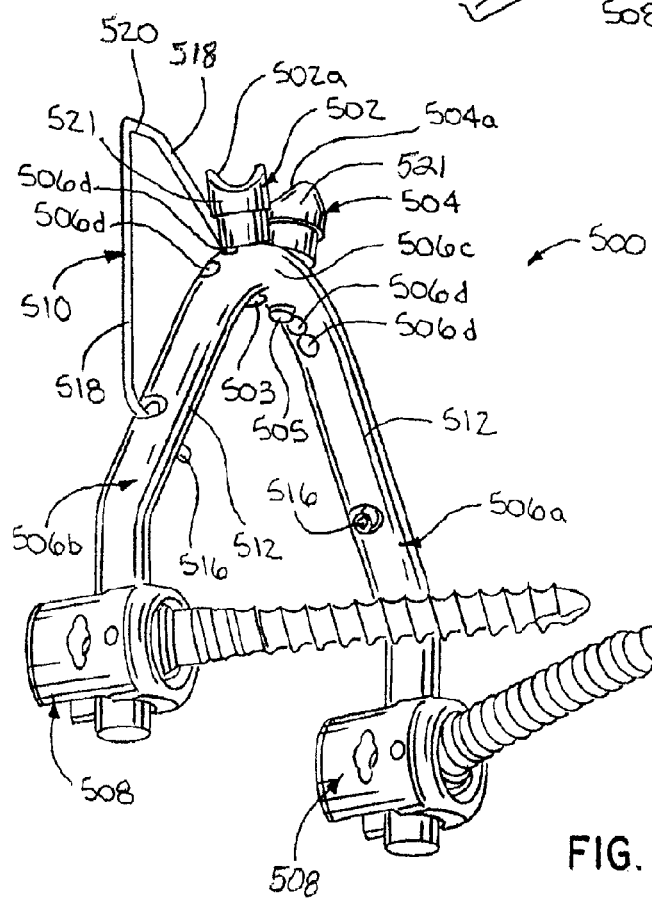
FIG. 13 is another perspective view of the spinal stabilization system depicted in FIG. 11 showing a concave seating surface of the engagement member for receiving a laminar region of a vertebra and a plurality of through-bores in the rod for adjustably locating the engagement members.

FIGS. 11-13 depict a spinal stabilization system 500 according to a fifth form of the present invention. The spinal stabilization system 500 includes a first engagement member 502, a second engagement member 504, and support structure including a rod 506, a pair of fixation devices 508, and an axial retention member 510. The engagement members 502, 504 abuttingly engage an inferior edge 11b of a laminar region 11 of a most superior or first vertebra 1a while the fixation devices secure the system 500 to the pedicle regions 13 of the most inferior or third vertebra 1c. Thus, similar to that described immediately above with reference to FIGS. 8-10, the spinal stabilization system 500 counteracts compressive loads applied to the spine to maintain an appropriate intervertebral spacing between the first, second and third vertebrae 1a, 1b, 1c. Specifically, a compressive load applied to any one or combination of the vertebrae 1a, 1b, 1c is directly transferred to the engagement members 502, 504 as well as the fixation devices 508. Such a compressive load operates to load the rod 506 partially in bending and partially in compression. The substantially rigid rod 506, therefore, counteracts the bending and compressive loads to maintain the intervertebral spacing. Additionally, however, the axial retention member 510 serves to counteract tensile loads applied to the spine by minimizing axial distraction of the spinous process 7 of the first vertebra 1a relative to the system 500 and the second and third vertebrae 1b, 1c. Specifically, a tensile load applied to one or more of the vertebrae 1a, 1b, 1c may be transferred directly to the axial retention member 510, which is also anchored to the rod 506, and wrapped about the spinous process 7 of the most superior vertebra 1a. This loads the axial retention member 510 partially in bending and partially in tension with the retention member resisting these forces. Therefore, the axial retention member 510 in combination with the rod 506 and fixation devices 508 counteract the tensile load to minimize distraction of the vertebrae 1a, 1b, 1c.

Each of the first and second engagement members 502, 504 include generally cylindrical members 521 extending upwardly to be directly attached to a portion of the rod 506. The first and second members 502, 504 include upper seating surfaces 502a, 504a, respectively, for receivingly engaging an inferior edge 11b of a laminar region 11 of the vertebra 1a. Similar to the rod 406 depicted and described with reference to FIGS. 8-10, the rod 506 of the spinal stabilization system 500 includes depending leg portions 506a and 506b. Each of the leg portions 506a, 506b include angularly extending portions 512 extending obliquely to longitudinally extending portions 514 that are to be generally aligned with the spinal axis L to generally extend in parallel thereto. As depicted in FIG. 13, the rod 506 includes an apex portion 506c having a plurality of transverse through-bores 506d within which stem portions 503, 505 of the engagement members 502, 504 are inserted to be fixedly disposed therein. In the form illustrated, the apex portion 506c includes six through-bores 506d allowing for the placement of the engagement members 501, 504 in a variety of different locations to suit different patients' vertebral construction. In an alternate form, the apex portion 506c may include any number of through-bores 506d.

The axial retention member 510 of the spinal stabilization system 500 generally includes a semi-rigid member such as a wire capable of withstanding tensile loads having attachment portions 516, angular portions 518, and an apex portion 520. The attachment portions 516 are disposed in transverse bores in the angular extending portions 512 of the rod 506 and attached thereto. The angularly extending portions 518 extend in the same direction or generally parallel to the adjacent angularly extending portions 512 of the rod 506. The apex portion 520 is disposed around or near the spinous process 7 adjacent the laminar region 11 of the vertebra against which the first and second engagement members 502, 504 abuttingly engage.

The axial retention member 510 in combination with the first and second engagement members 502, 504, as well as the fixation devices 508 serve to substantially fix the relative position of the vertebrae to which they are attached. It should be appreciated that the first and second engagement members 502, the rod 506 and the fixation devices 508 of the spinal stabilization system 500 may be implanted similar to that described above with reference to FIGS. 8-10. One procedure involving the implantation of the spinal stabilization system 500 would require the surgeon to pivot the apex portion 520 of the axial retention member 510 about the attachment portions 516 and around the superior spinous process for tightly, frictionally engaging thereon. Another procedure, however, would require the surgeon to, first, place the apex portion 520 on the superior spinous process 7 and then fix the opposite ends to the rod 506 at the attachment portions 516.

Figure 14:
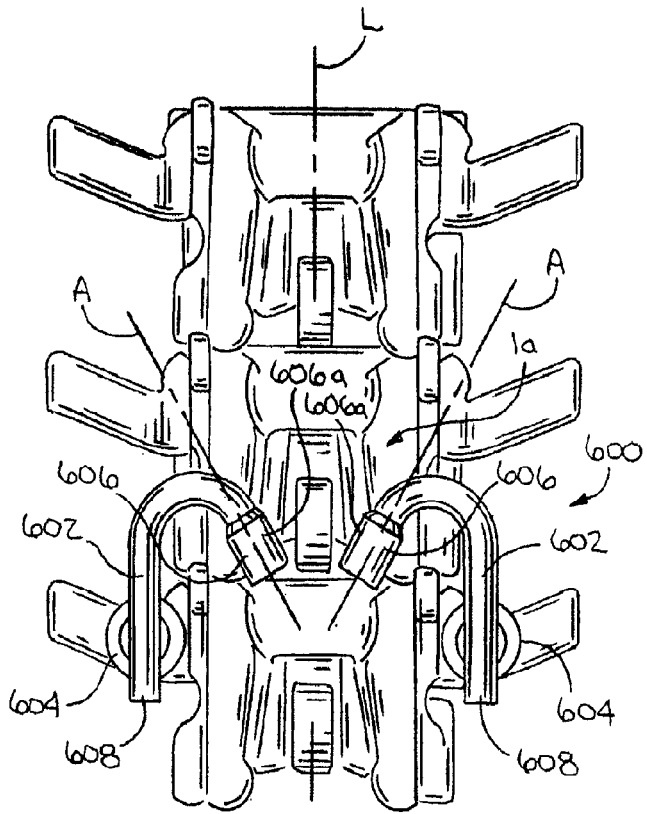
FIG. 14 is a perspective view of a spinal stabilization system according to a sixth form of the present invention including a pair of generally J-shaped rods having engagement member portions engaging a laminar portion of a first vertebra and opposing leg portions fixedly attached to pedicle regions of a second vertebra.
Figure 15:
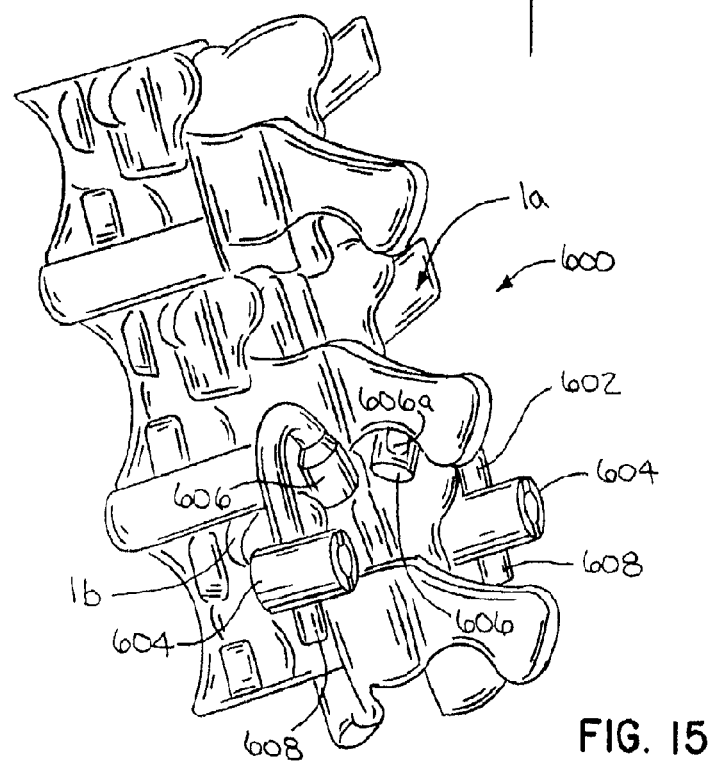
FIG. 15 is another perspective view of the spinal stabilization system according to the sixth form of the present invention depicted in FIG. 14.
Figure 16:
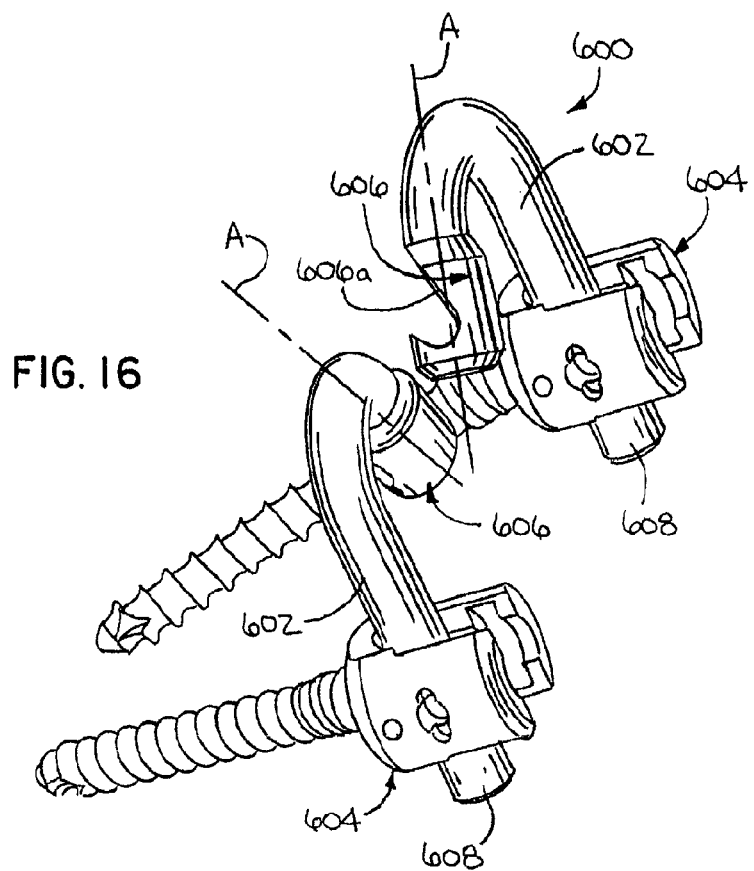
FIG. 16 is another perspective view of the spinal stabilization system according to the sixth form of the present invention depicted in FIG. 14 showing a hook-shaped seating surface of the engagement member adapted to receive a laminar region of a vertebra.

FIGS. 14-16 depict a spinal stabilization system 600 according to a sixth form of the present invention. The spinal stabilization system 600 generally includes a pair of rods 602 and support structure including a pair of fixation devices 604. The fixation devices 604 fix each of the rods 602 to pedicle regions 13 of an inferior vertebra 1b. Each of the rods 602, however, is generally J-shaped and has portions 606a that are configured to closely engage the inferior edges 11b of the laminar region 11 of the superior vertebra 1a. Therefore, the rods 602 effectively minimize any reduction in the intervertebral spacing between the superior and inferior vertebrae 1a, 1b by counteracting compressive loads applied to the spine. Specifically, a compressive load applied to either the superior or inferior vertebra 1a, 1b is transferred directly to at least one of the rods 602 and one of the fixation devices 604. This loads the rod 602 primarily in bending, but also partially in tension. Therefore, the rod 620 at least semi-rigidly counteracts the compressive load to maintain the intervertebral spacing.

As mentioned, the rods 602 are generally J-shaped. More specifically, each of the rods 602 includes an enlarged engagement portion 606 and a longitudinal portion 608. The engagement portions 606 include concave cut-out recesses having seating surfaces 606a. The enlarged portions 606 generally has a cylindrical configuration with the cut-out surfaces 606a extending from the side of the portion 606 inwardly at an oblique angle the axis A of the cylindrical portion 606a. The longitudinal portions 608 generally extend longitudinally along the axis L of the spine and are locked with the fixation devices 604, which are similar to that described above and incorporated herein. In the form illustrated, the engagement portions 606 of the rods 602 abuttingly engage and support an inferior edge 11b of a laminar region 11 of the superior vertebrae 1a. Additionally, the fixation devices 604 are attached to corresponding pedicle regions 13 of the inferior vertebra 1b. In one form of the spinal stabilization system 600, the engagement portions 606 may further include dampers including a resilient material directly engaged with the vertebra 1a to minimize potential damage caused thereto. Additionally, while the rods 602 have been disclosed and described herein as being generally J-shaped, an alternate form of the spinal stabilization system 600 may include C-shaped, V-shaped, or some other shaped rods 602.

Figure 17:
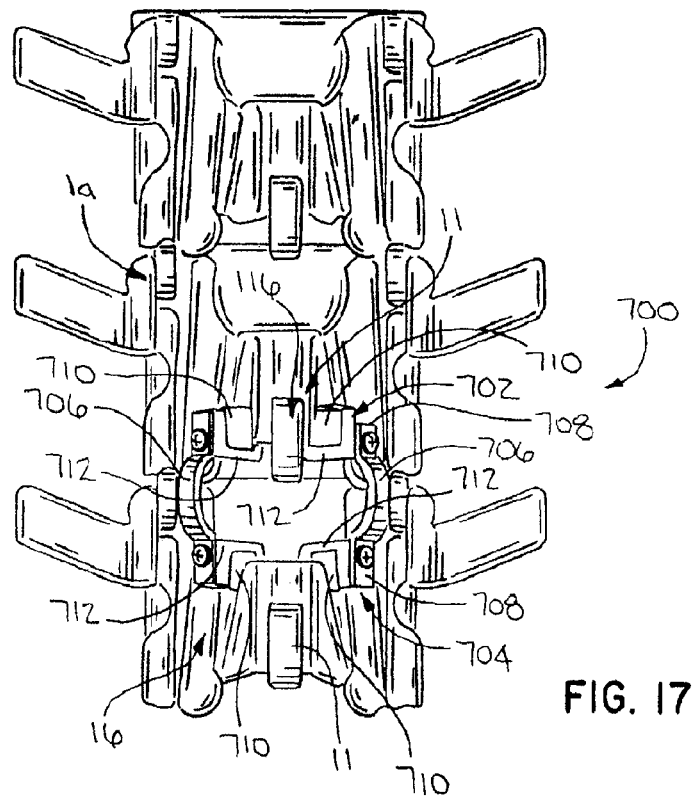
FIG. 17 is a perspective view of a spinal stabilization system according to a seventh form of the present invention including a first engagement member abuttingly engaging a laminar region of a first vertebra, a second engagement member abuttingly engaging a laminar region of a second vertebra, and a pair of arch-shaped biasing members disposed therebetween.
Figure 18:
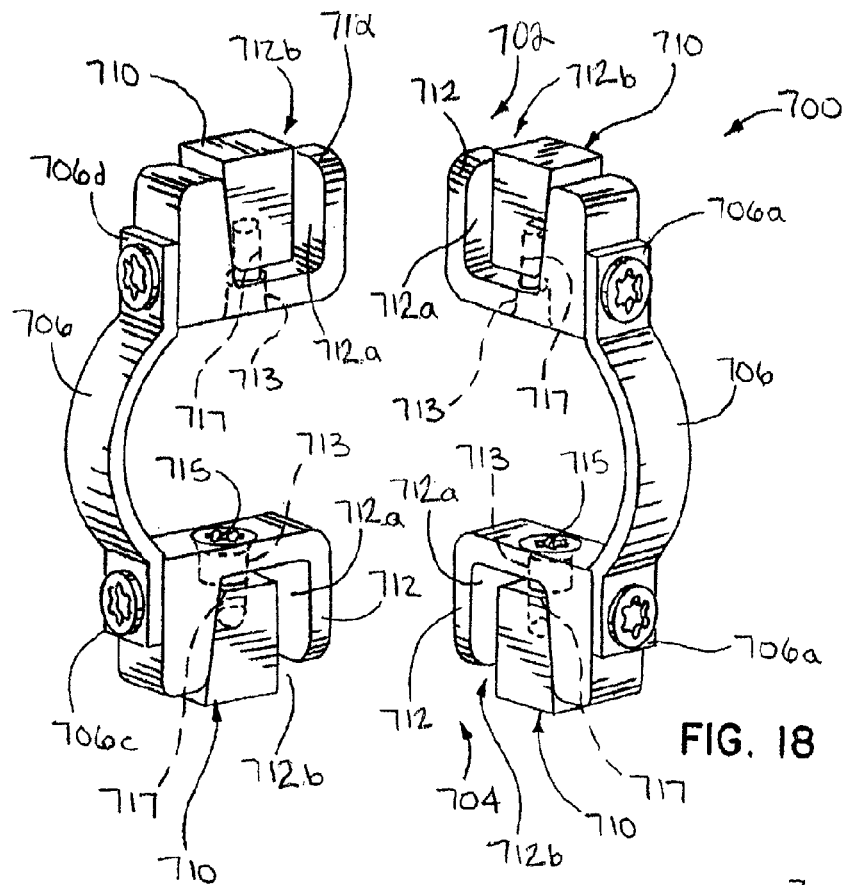
FIG. 18 is an enlarged posterior perspective view of the spinal stabilization system of FIG. 17 showing C-shaped portions of the engagement members including threaded fasteners securing block-shaped dampers therein and gripping regions adapted to engage laminar regions of the vertebrae to minimize relative movement therebetween.
Figure 19:
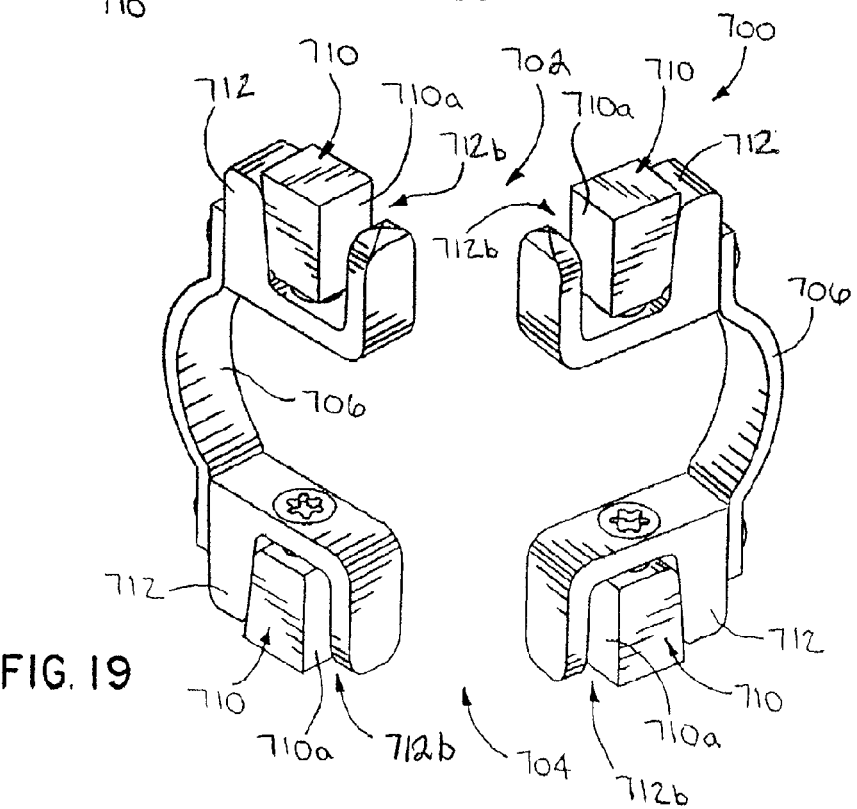
FIG. 19 is an enlarged anterior perspective view of the spinal stabilization system of FIGS. 17 and 18 showing C-shaped portions of the engagement members including threaded fasteners securing block-shaped dampers therein and gripping regions adapted to engage laminar regions of the vertebrae to minimize relative movement therebetween.

FIGS. 17-19 depict a spinal stabilization system 700 according to a seventh form of the present invention. The spinal stabilization system 700 includes a first engagement member 702, a second engagement member 704, and a support structure including a pair of biasing members 706. The first engagement member 702 engages the inferior edge 11b of a laminar region 11 of the superior vertebra 1a. The second engagement member 704 engages the superior edge 11a of the laminar region 11 of the inferior vertebra 1b. The biasing members 706 operate to bias the first and second engagement members 702, 704 apart and into secure engagement with the corresponding vertebrae 1a, 1b, as well as counteract any compressive forces applied to the spine to appropriately maintain the intervertebral spacing between the superior and inferior vertebrae 1a, 1b. Specifically, a compressive load applied to either or both of the superior and inferior vertebrae 1a, 1b is directly transferred to the engagement members 702, 704. This places the biasing members 706 in compression. Therefore, the biasing members 706 resiliently counteract the compressive load to maintain the intervertebral spacing.

The first engagement member 702 and the second engagement member 704 each include a base clamp 708 and a damper 710. Each of the base clamps 708 includes opposing C-shaped portions 712. The C-shaped portions 712 include through bores 713 receiving threaded fasteners 715, as is depicted in FIGS. 18 and 19. The dampers 710 include generally block-shaped members disposed within openings 712b of the C-shaped portions 712. The threaded fasteners 715 threadingly engage blind threaded bores 717 formed in the dampers 710 to secure the dampers in place. Additionally, as can be seen in FIGS. 18 and 19, an anterior surface 712a of the C-shaped members 712, as well as a posterior surface 710a of the dampers 710, include a gripping region that is scored with a plurality of horizontal linear scores. The horizontal scores serve to grip the anterior and posterior surfaces 11c, 11b of the laminar regions 11 of the respective vertebrae 1a, 1b to minimize displacement of the spinal stabilization device 700 relative thereto. While the scoring has been immediately disclosed and described herein as including a plurality of horizontal markings, an alternate form of the scoring may include vertical markings, angled markings, cross-hatched markings or any other form of marking or formation on the respective surfaces to achieve the desired restriction in relative movement.

The biasing members 706 include generally arch-shaped spring steel plates. Opposing ends of the arch-shaped steel plates 706 include flange portions 706a that are fixedly attached to the corresponding base clamps 708. In one embodiment, the arch-shaped steel plates 706 are attached to the base clamps 708 by threaded fasteners. However, in an alternative embodiment, it should be appreciated that the biasing member 706 may be attached to the base clamps 708 by any suitable means such as welding, soldering, and/or any other fastener capable of serving the principles of the present invention.

So configured, the spinal stabilization system 700 limits reduction of the intervertebral spacing between the adjacent vertebrae 1a, 1b. Specifically, the opposing C-shaped portions 712 of the base clamps 708 receive edges 11a, 11b of the laminar regions 11 of the adjacent vertebrae 1a, 1b. The dampers 710 disposed within the C-shaped portions 712 of the base clamps 708 provide a cushion by deforming under loads or forces such that forces applied by the base clamps 708 on the vertebrae 1a, 1b do not damage the laminar regions 11 of the vertebrae 1a, 1b. This is accomplished by the C-shaped portions 712 and dampers 710 defining the space 712b including gripping surfaces 710a, 712a within which the laminar regions 11 of the vertebrae 1a, 1b are disposed. Furthermore, the dampers 710 additionally or alternatively provide a means for shimming the spacing between the laminar regions 11 and the C-shaped portions 712 of the engagement members 702, 704. Additionally, the biasing members 708 provide a distraction bias to the opposing base clamps 708, thereby maintaining the engagement between the engagement members 702, 704 and the laminar regions 11 of the vertebrae 1a, 1b.

Similar to the spinal stabilization systems 10 and 200 discussed above, during surgery, a surgeon need only push the base clamps 708 of the spinal stabilization system 700 together or alternatively spread the vertebrae 1a, 1b apart. Subsequently, the surgeon may insert the spinal stabilization system 700 into the intervertebral space and release the compressive force. With the openings in the opposing C-shaped portions 712 of the base clamps 708 properly aligned with the corresponding edges 11a, 11b of the laminar regions 11 of the adjacent vertebrae 1a, 1b, the biasing members 706 will sufficiently distract the base clamps 708 into abutting engagement therewith.

Figure 20:
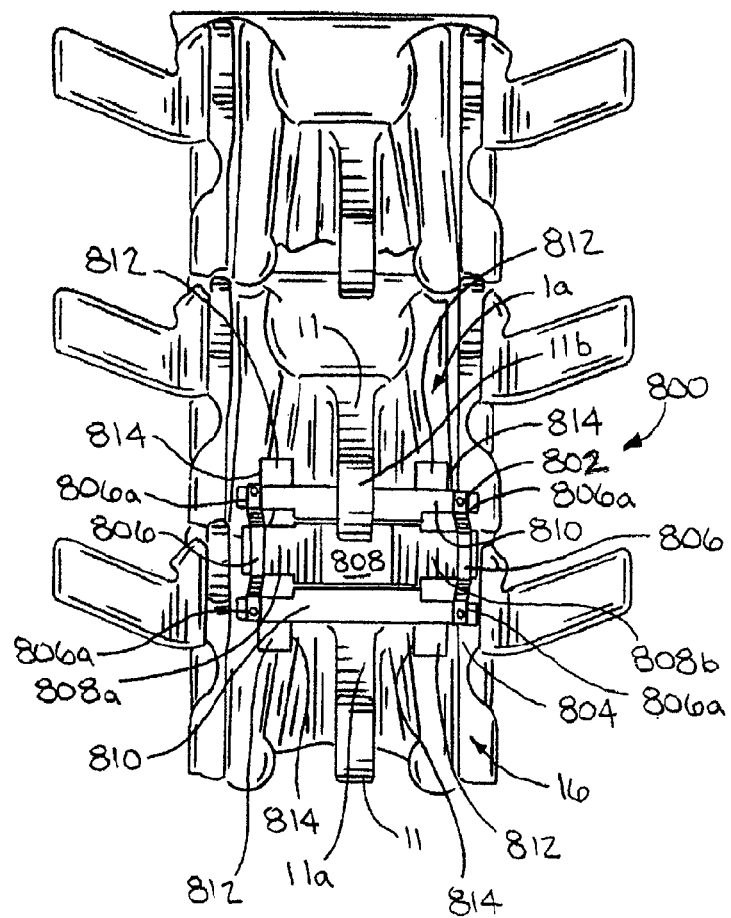
FIG. 20 is a perspective view of a spinal stabilization system according to an eighth form of the present invention including a first engagement member abuttingly engaging a laminar region of a first vertebra, a second engagement member abuttingly engaging a laminar region of a second vertebra, a resilient body disposed between the first engagement member and the second engagement member, and a pair of arch-shaped biasing members attached between the first and second engagement members.
Figure 21:
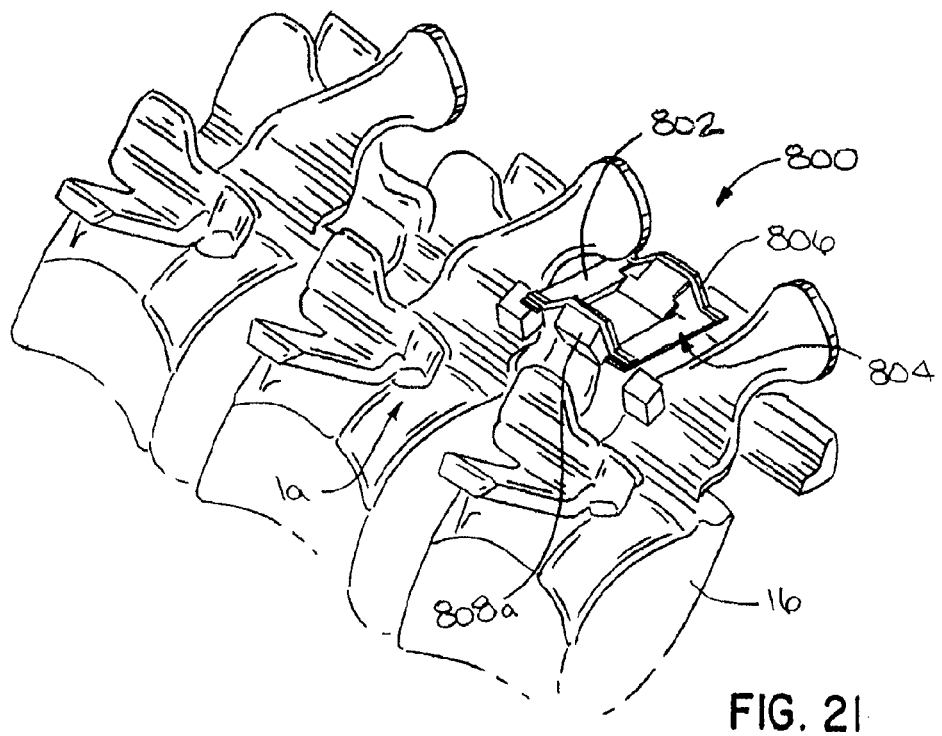
FIG. 21 is another perspective view of the spinal stabilization system according to the eighth form of the present invention depicted in FIG. 11.
Figure 22:
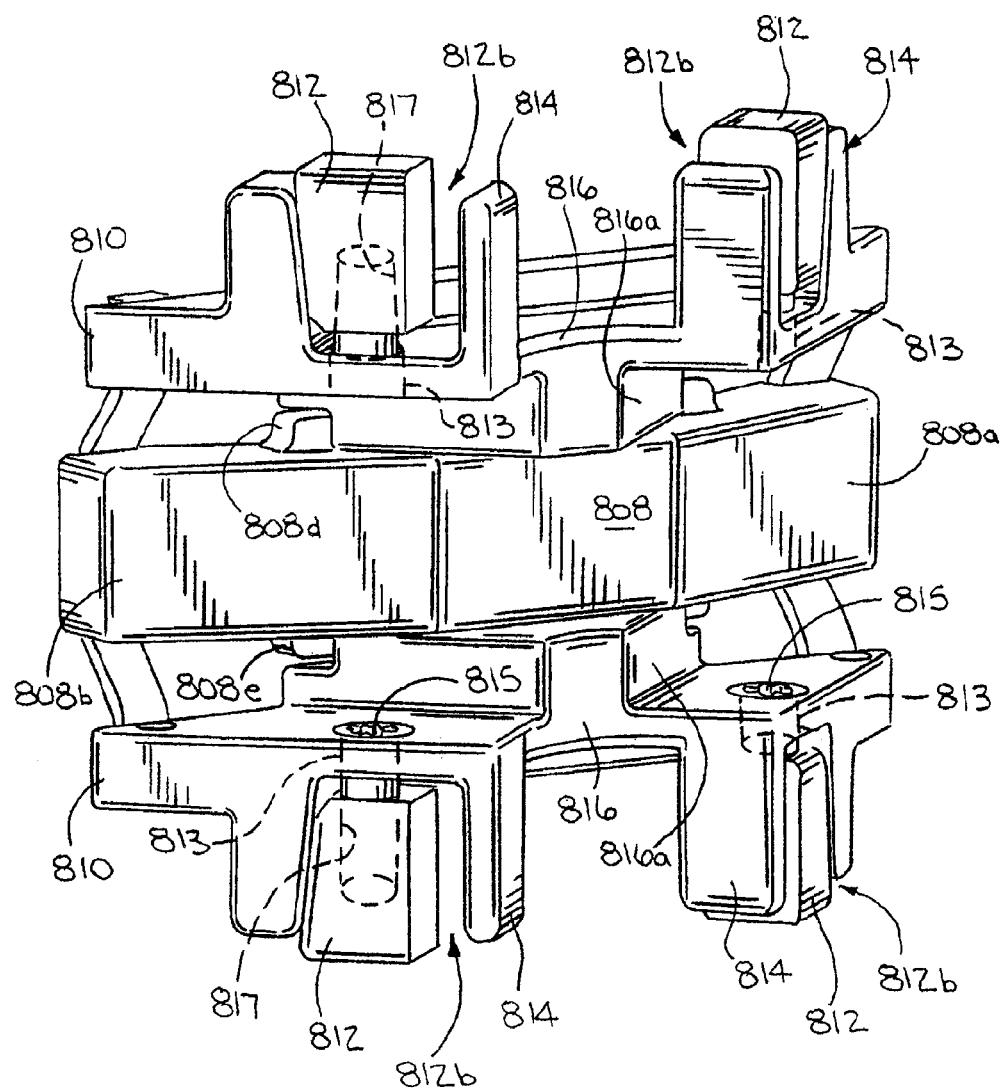
FIG. 22 is an enlarged anterior perspective view of the spinal stabilization system of FIGS. 20 and 21 showing C-shaped portions of the engagement members including threaded fasteners securing block-shaped dampers therein and gripping regions adapted to engage laminar regions of the vertebrae to minimize relative movement therebetween.

FIGS. 20-22 depict a spinal stabilization system 800 according to the eighth form of the present invention. The spinal stabilization system 800 includes a first engagement member 802, a second engagement member 804, and support structure having a pair of biasing members 806, and a resilient body 808. The first and second engagement members 802, 804 respectively engage the inferior and superior edges 11b, 11a of the laminar regions 11 of the corresponding vertebrae 1a, 1b. The biasing members 806 bias the engagement members 802, 804 into this engagement. Additionally, the resilient body 808 is generally disposed between the first and second engagement members 802, 804 and serves to absorb at least a portion of a compressive load applied to the spine and assist the biasing members 806 in maintaining the intervertebral spacing between the vertebrae 1a, 1b. Specifically, a compressive load applied to either or both of the superior and inferior vertebrae 1a, 1b is transferred directly to engagement members 802, 804. This places the biasing members 806, as well as the resilient body 808, in compression. Therefore, the biasing members 806 and resilient body 808 counteract the compressive load and maintain the intervertebral spacing.

Similar to that described immediately above, the first and second engagement members 802, 804 each include a base plate 810 and dampers 812. The base plate 810 includes C-shaped portions 814 interconnected by laterally extending truss portions 816. Similar to that described immediately above, the C-shaped portions 814 include through-bores 813 receiving threaded fasteners 815 that threadingly engage blind bores 817 in the dampers 812 to secure the dampers to the base plate 810. Additionally, the dampers 812 and C-shaped portions 814 include a gripping region having scored surfaces identical to that described above with respect to FIGS. 17-19. The truss portions 816 additionally include stop bodies 816a extending axially therefrom, as is depicted in FIG. 22 and will be described in more detail below.

The biasing members 806 include arch-shaped plates. In one form, the resilient body 808 includes a complex three-dimensional shape formed of a resilient elastic material such as rubber. However, the resilient body 808 may be made of any suitable material such as foam, polymer, copolymer, or any other suitable material.

The dampers 812 of the first and second engagement members 802, 804 are generally block-shaped members disposed within openings 812b of the C-shaped portions 814 of the base plates 810. The biasing members 806 have opposite upper and lower flange portions 806a fixedly attached to the first and second engagement members 802, 804, respectively. The biasing members 806 are fixedly attached to the engagement members 802, 804 such as illustrated by threaded fasteners or screws.

The resilient body 808 is disposed axially between the first and second engagement members 802, 804. As can be seen in FIG. 22, the resilient body 808 has lateral end portions 808a, 808b interconnected by a central body portion 808c, as well as a superior tab portion 808d and an inferior tab portion 808e. Anterior surfaces of the superior and inferior tab portions 808d, 808e abuttingly engage posterior surfaces of the axially extending stop bodies 816a of the truss portions 816 of the base plates 810. This anterior/posterior abutment serves to minimize shifting of the resilient body 808 in the anterior direction relative to the base plates 810, while engagement between the biasing members 806 and the lateral end portions 808a, 808b of the resilient body 808 minimize shifting of the resilient body 808 in the posterior direction relative to the base plates 810. Additionally, the first and second engagement members 802, 804 sandwich the resilient body 808 to minimize shifting of the resilient body in the superior/inferior directions. In alternative embodiments the resilient body 808 may actually be attached to the first and second engagement members 802, 804. In yet a still further form, the resilient body 808 may be maintained between the engagement members 802, 804 by a compressive load created by the biasing members 806. Nevertheless, in any of the envisioned configurations, it should be appreciated that the resilient body 808 can be attached to either the engagement members 802, 804 or the biasing members 806 via an adhesive, a threaded fastener, a rivet, a screw or any other similar means.

So configured, the opposing C-shaped portions 814 of the base plates 810 receive the edges 11a, 11b of the laminar regions 11 of the adjacent vertebrae 1a, 1b, as depicted in FIGS. 20 and 21. In one form, the dampers 812 serve as cushions between the base plates 810 and the laminar regions 11 of the vertebrae 1a, 1b to minimize deterioration thereof. Furthermore, the dampers 812 may additionally serve as shims to ensure secure engagement between the vertebrae 1a, 1b and the engagement members 802, 804. Finally, during surgery, a surgeon need only compress the first and second engagement members 802, 804 together or spread the vertebrae 1a, 1b apart prior to inserting the spinal stabilization system 800 into the intervertebral space. Once inserted, the surgeon may release the compressive force applied to the engagement members or the spreading force applied to the vertebrae, thereby enabling the base plates 810 of the engagement members 802, 804 to receivingly engage the laminar regions 11 of the adjacent vertebrae 1a, 1b. Therefore, the spinal stabilization system 800 limits a reduction in the intervertebral space.

Figure 23:
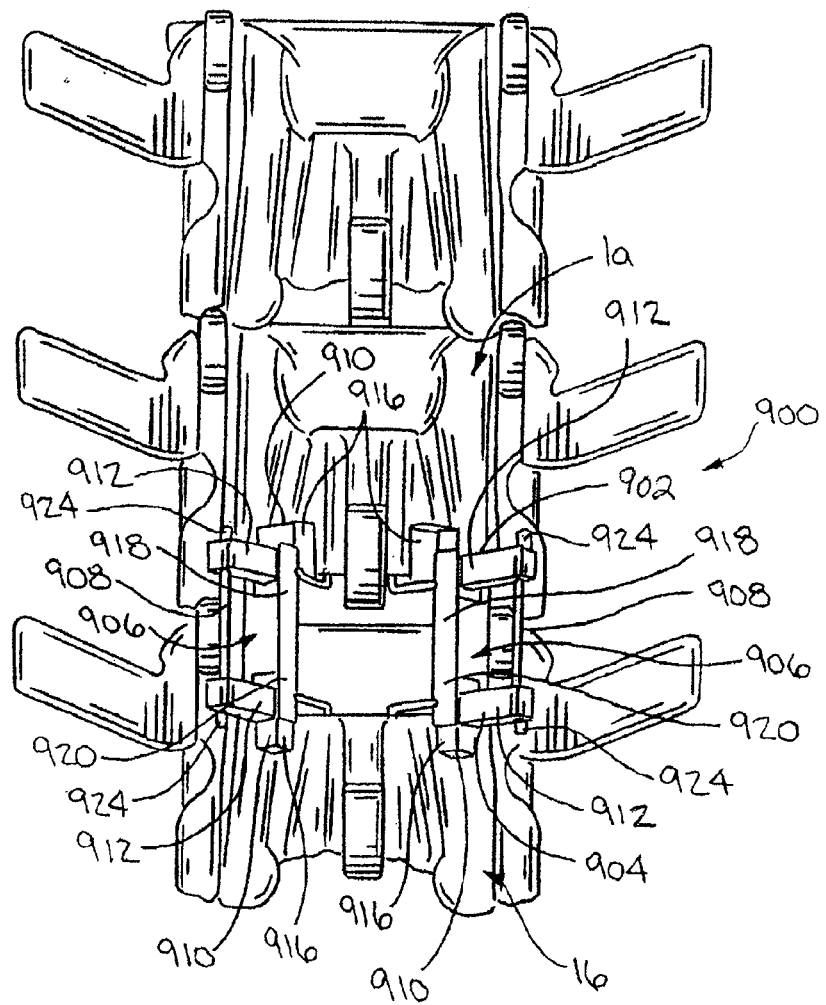
FIG. 23 is a perspective view of a spinal stabilization system according to a ninth form of the present invention including a first engagement member abuttingly engaging a laminar region of a first vertebra, a second engagement member abuttingly engaging a laminar region of a second vertebra, a pair of pivotal support structures disposed between the first and second engagement members, and a pair of tensioning members disposed between the first and second engagement members opposite the pivoting members from the laminar regions of the vertebrae.
Figure 24:
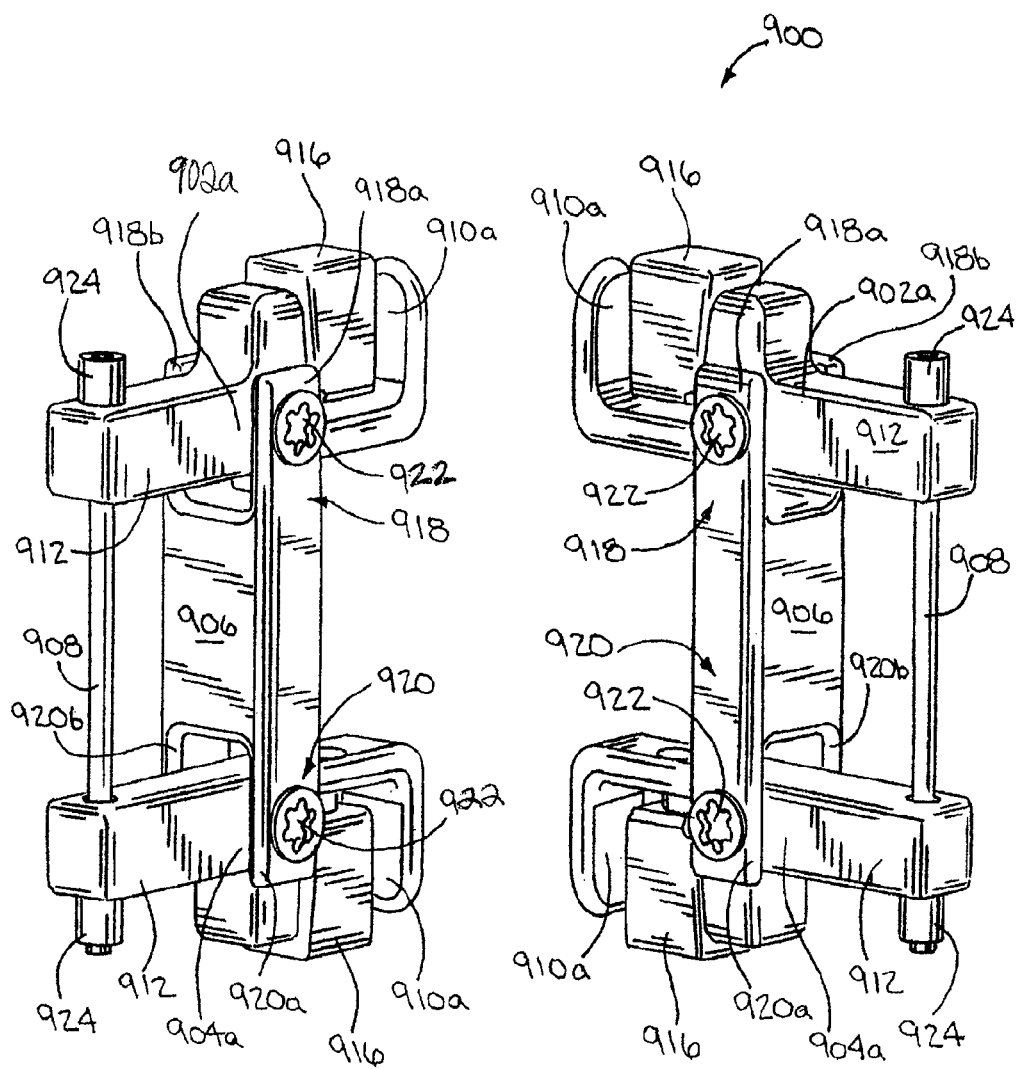
FIG. 24 is an enlarged posterior perspective view of the spinal stabilization system of FIG. 23 showing C-shaped portions of the engagement members including threaded fasteners securing block-shaped dampers therein and scored regions adapted to engage laminar regions of the vertebrae to minimize relative movement therebetween.
Figure 25:
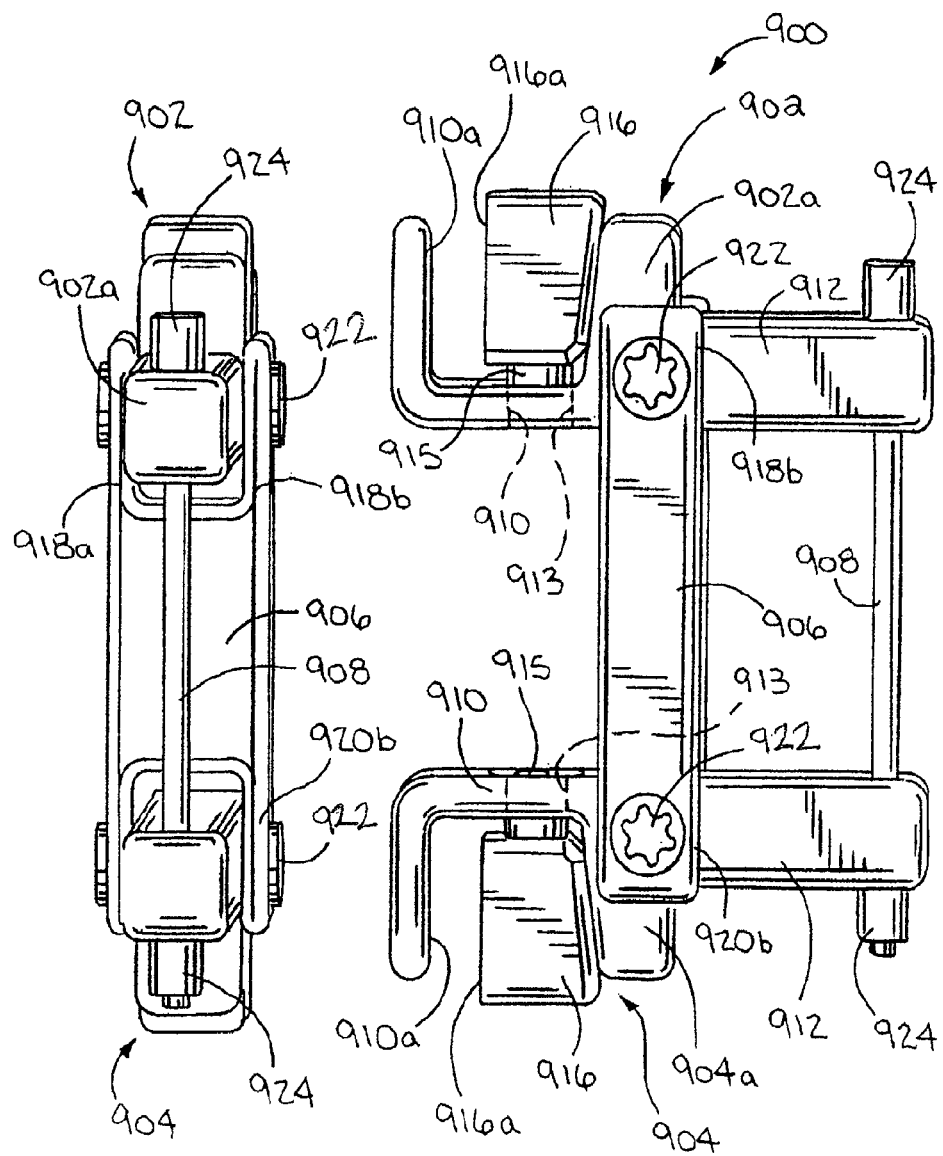
FIG. 25 is an enlarged side perspective view of the spinal stabilization system of FIG. 23 showing C-shaped portions of the engagement members including threaded fasteners securing block-shaped dampers therein and gripping regions adapted to engage laminar regions of the vertebrae to minimize relative movement therebetween.

FIGS. 23-25 depict a spinal stabilization system 900 according to the ninth form of the present invention. The spinal stabilization system 900 includes a pair of first engagement members 902, a pair of second engagement members 904, and a support structure having a pair of pivotal supports 906, and a pair of tensioning members 908. The first and second pairs of engagement members 902, 904 abuttingly engage the inferior and superior edges 1b, 1a of the laminar regions 11 of the superior and inferior vertebrae 1a, 1b, respectively, under the load of the tensioning members 908. The pivotal supports 906 each provide the necessary support to counteract compressive loads applied to the spine and ensure proper maintenance of the intervertebral spacing between the superior and inferior vertebrae 1a, 1b. Specifically, a compressive load applied to either or both of the superior and inferior vertebrae 1a, 1b is transferred directly to engagement members 902, 904. This places the pivotal supports 906 in slight compression and the tensioning members 908 in tension. Therefore, the pivotal supports 906 and the tensioning members 908 counteract the compressive load on the vertebrae 1a, 1b to maintain the intervertebral spacing.

Each of the first and second engagement members 902, 904 include C-shaped portions 910, arm portions 912, and dampers 916. Identical to those described above, the C-shaped portions 910 include through bores 913 receiving threaded fasteners 915 threadingly engaging blind bores in the dampers 916 to secure the dampers 916 thereto. Additionally, identical to that described above, the C-shaped portions 910 and the dampers 916 include scored surfaces 910a, 916a for limiting relative movement between the engagement members 902, 904 and the corresponding vertebrae 1a, 1b. The dampers 916 include generally block-shaped members disposed within the C-shaped portions 910 and secured thereto, as stated above. Each of the pivotal supports 906 includes a generally elongated member having an upper yoke 918, a lower yoke 920, and a pair of pivot pins 922. Each of the tensioning members 908 include generally elongated thin rods and a pair of locking fasteners 924.

The upper yoke 918 of each of the pivotal supports 906 pivotally receive a portion 902a of the first engagement members 902. The lower yokes 920 of the pivotal supports 906 pivotally receive portions 904a of the second engagement members 904. The pivot pins 922 are disposed through apertures in opposed projecting arms 918a, 918b and 920a, 920b, of the upper and lower yokes 918, 920, respectively, as well as through bores (not shown) in the portions 902a, 904a of the first and second engagement members 902, 904. Additionally, the arm portions 912 of the first and second engagement members 902, 904 include axially extending bores (not shown) receiving opposing ends of the tensioning members 908. The tensioning members 908 extend axially slightly beyond the arm portions 912 of the first and second engagement members 902, 904 and receive the locking fasteners 922. The locking fasteners 922 set the tension that the tensioning members 908 apply to the first and second engagement members 902, 904. In one form, the locking fasteners 922 include cylindrical sleeve-type locking fasteners press-fit over the ends of the tensioning members 908 such as cable crimps. In an alternative form, the locking fasteners 922 may include threaded nuts or any other means for fixing the tension applied by the tensioning members 908.

As stated above, the dampers 916 are disposed within the C-shaped portions 910 of the first and second engagement members 902, 904. In one form, the dampers 916 include deformable material serving to reduce deterioration of the laminar regions 11 of the corresponding vertebrae 1a, 1b engaged by the engagement members 902, 904. In another form, the dampers 916 further serve as shims ensuring a close fit between the C-shaped portions 910 and the vertebrae 1a, 1b.

During surgery, the entire spinal stabilization system 900 is preassembled, but for the tensioning members 908. Therefore, the surgeon appropriately distracts the arm portions 912 of the first and second engagement members 902, 904 relative to the pivotal support 906. This reduces the space between the C-shaped portions 910 thereof and enables the surgeon to insert the spinal stabilization system 900 into the intervertebral space. Once inserted, the surgeon reduces the distance between the arm portions 912 of the first and second engagement members 902, 904, which correspondingly distract the C-shaped portions 910. Continued distraction of the C-shaped portions 910 causes them to receivingly engage the edges 11a, 11b of the laminar regions 11 of the adjacent vertebrae 1a, 1b. At this point, the tensioning members 908 may be inserted through the axial bores in the arm portions 912 of the first and second engagement members 902, 904. Then, the locking fasteners 922 are applied thereto to fix the distance between the arm portions 912 securing the spinal stabilization system 900 within the intervertebral space.

Figure 26:
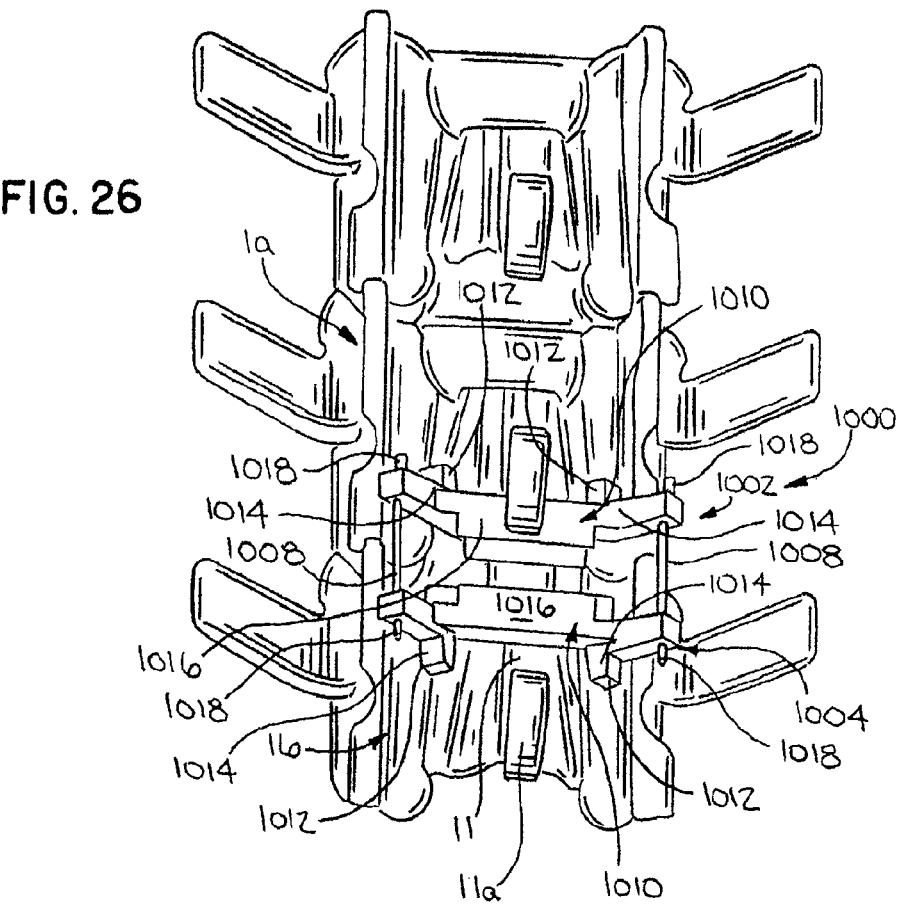
FIG. 26 is a perspective view of a spinal stabilization system according to a tenth form of the present invention including a first engagement member abuttingly engaging a laminar region of a first vertebra, a second engagement member abuttingly engaging a laminar region of a second vertebra, a resilient body disposed between the first engagement member and the second engagement member, and a pair of tensioning members extending between the first engagement member and the second engagement member.
Figure 27:
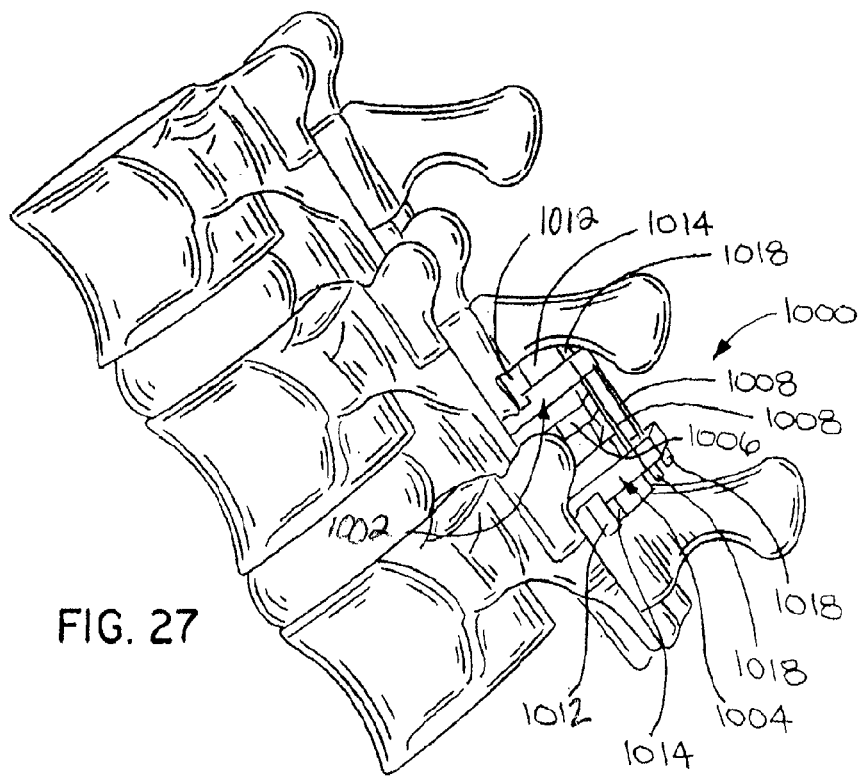
FIG. 27 is another perspective view of the spinal stabilization system according to a tenth form of the present invention depicted in FIG. 26.
Figure 28:
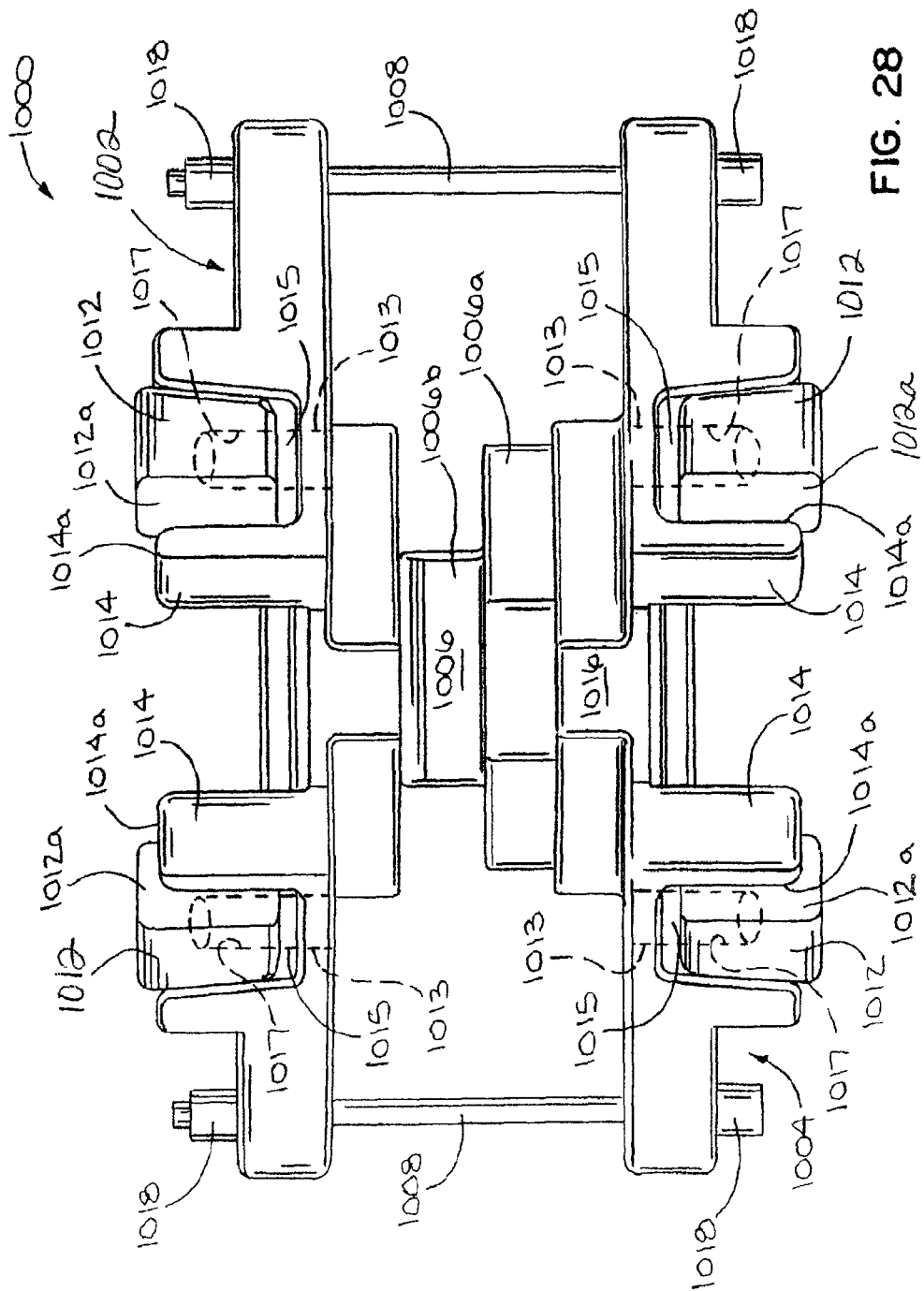
FIG. 28 is an enlarged anterior perspective view of the spinal stabilization system of FIGS. 26 and 27 showing C-shaped portions of the engagement members including threaded fasteners securing block-shaped dampers therein and gripping regions adapted to engage laminar regions of the vertebrae to minimize relative movement therebetween.

FIGS. 26-28 depict a spinal stabilization system 1000 in accordance with a tenth form of the present invention. The spinal stabilization system 1000 includes a first engagement member 1002, a second engagement member 1004, and a support structure having a resilient body 1006, and a pair of tensioning members 1008. The first and second pairs of engagement members 1002, 1004 abuttingly engage the inferior and superior edges 1b, 1a of the laminar regions 11 of the superior and inferior vertebrae 1a, 1b, respectively, under the load of the tensioning members 1008. The resilient body 1006, which is disposed axially between the engagement members 1002, 1004 serves to absorb at least a portion of a compressive load applied to the spine to ensure proper maintenance of the intervertebral spacing between the superior and inferior vertebrae 1a, 1b. Specifically, a compressive load applied to either or both of the superior and inferior vertebrae 1a, 1b is transferred directly to engagement members 1002, 1004. This places the resilient body 1006 in compression and the tensioning members 1008 in slight tension. Therefore, the resilient body 1006 and the tensioning members 1008 counteract the compressive load on the vertebrae 1a, 1b to maintain the intervertebral spacing.

Similar to that described above in accordance with the eighth form, each of the first and second engagement members 1002, 1004 include a base plate 1010 and a damper 1012. Each base plate 1010 includes a pair of opposing C-shaped portions 1014 and a truss portion 1016 that extends laterally to interconnect the C-shaped portions 1014.

Additionally, identical to that described above, the C-shaped portions 1014 and dampers 1012 include anterior and posterior gripping regions having scored surfaces 1014a, 1012a, respectively, for gripping the laminar regions of the adjacent vertebrae and limiting relative displacement between the spinal stabilization device 1000 and the vertebrae. Furthermore, the C-shaped portions 1014 include bores 1013 receiving threaded fasteners 1015 that threadingly engage blind bores 1017 in the dampers 1012.

The resilient body 1006 includes a pair of three-dimensional generally block-shaped bodies formed of a material such as rubber and stacked axially relative to each other. As depicted in FIG. 28, the resilient body 1006 includes an enlarged base portion 1006a supporting a smaller upper portion 1006b. The smaller upper portion 1006b engages an axially extending stop body 1016a extending from the first engagement member 1002. The enlarged base portion 1006a engages an axially extending stop body 1016a extending from the second engagement member 1004. Therefore, the axially extending stop bodies 1016a extending from the first and second engagement members 1002, 1004 sandwich the resilient body 1006 such that the resilient body continuously applies a tensile load distracting the first and second engagement members 1002, 1004 into engagement with the corresponding vertebrae.

The resilient body 1006 may include any deformable resilient material such as foam, a copolymer, a polymer, or any other such material capable of serving the principles of the present invention. Additionally, it should be appreciated that in an alternate form, the resilient body 1006 may be fixedly attached to the first and second engagement members 1002, 1004 with an adhesive. Alternatively, however, the resilient body 1006 may be attached to the engagement members 1002, 1004 by fasteners such as threaded fasteners or rivets. In yet another form, the resilient body 1006 may not be fixed to the engagement members 1002, 1004 at all, but rather, simply maintained therebetween by a compressive force generated by the tensioning members 1008. Similar to those discussed above in accordance with the ninth form of the invention, the tensioning members 1008 include generally elongated thin rods secured by a pair of locking fasteners 1018. So configured, the spinal stabilization system 1000 limits reduction of the intervertebral space.

During surgery, similar to embodiments described hereinabove, the entire spinal stabilization system 1000 is preassembled, but for the tensioning members 1008. Further yet, to achieve implantation, the surgeon need only compress the first and second engagement members 1002, 1004 or spread the vertebrae 1a, 1b and insert the spinal stabilization system 1000 into the intervertebral space. Upon insertion, the surgeon may release the compressive load or spreading force and enable the engagement members 1002, 1004 to engage tightly against the edges 11a, 11b of the laminar regions 11 of the adjacent vertebra. Subsequently, the surgeon inserts the tensioning members 1008 through axially aligned bores within the engagement members 1002, 1004. Finally, the surgeon need only attach the locking fasteners 1018 to the projecting ends of the tensioning members 1008. It should be appreciated that the locking fasteners 1018 of the spinal stabilization system 1000 may include any of the forms discussed above in accordance with the ninth form or any other forms.

Figure 29:
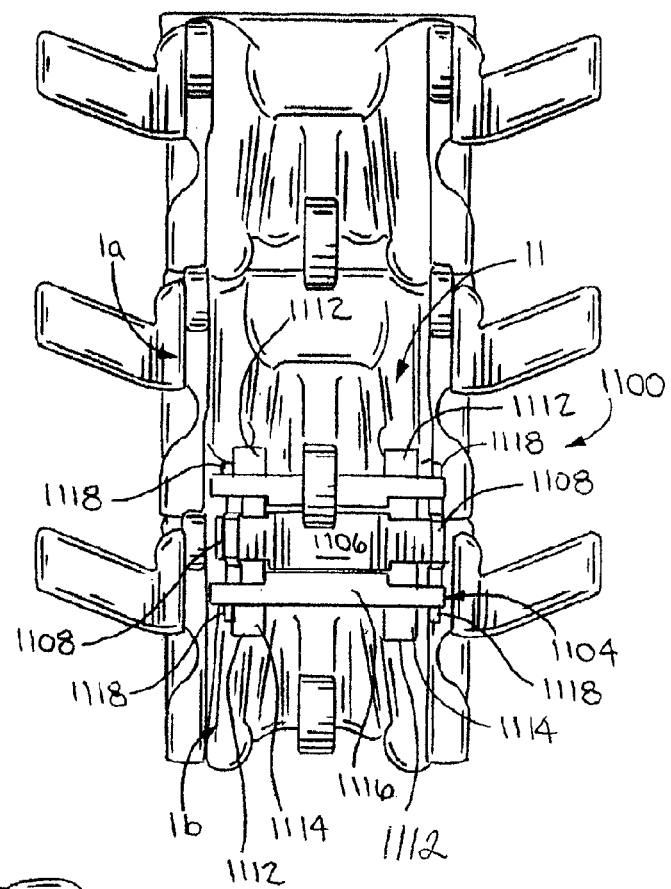
FIG. 29 is a perspective view of a spinal stabilization system according to an eleventh form of the present invention including a first engagement member abuttingly engaging a laminar region of a first vertebra, a second engagement member abuttingly engaging a laminar region of a second vertebra, a resilient body disposed between the first engagement member and the second engagement member, and a pair of tensioning members connected between the first engagement member and the second engagement member.
Figure 30:
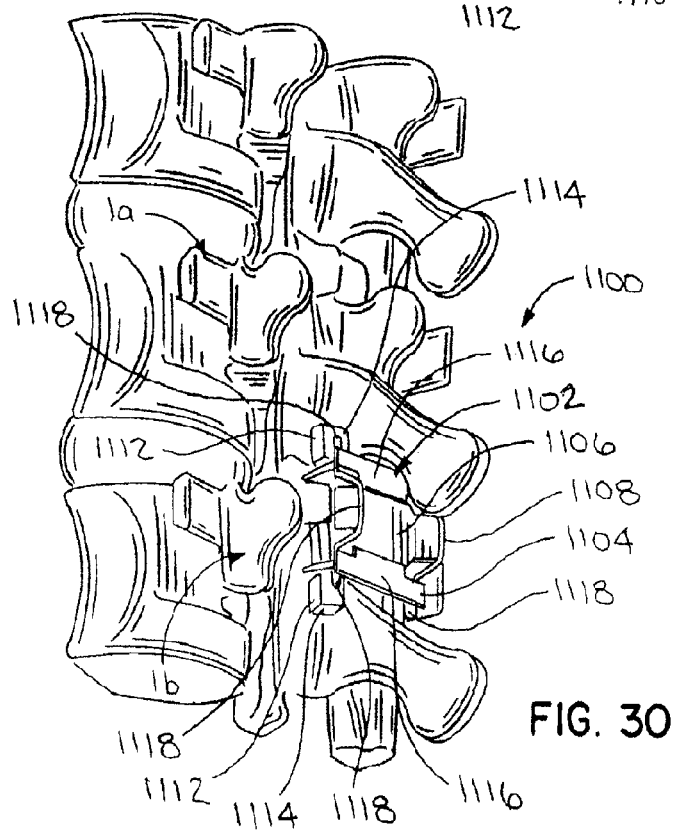
FIG. 30 is another perspective view of the spinal stabilization system according to the eleventh form of the present invention depicted in FIG. 29.
Figure 31:
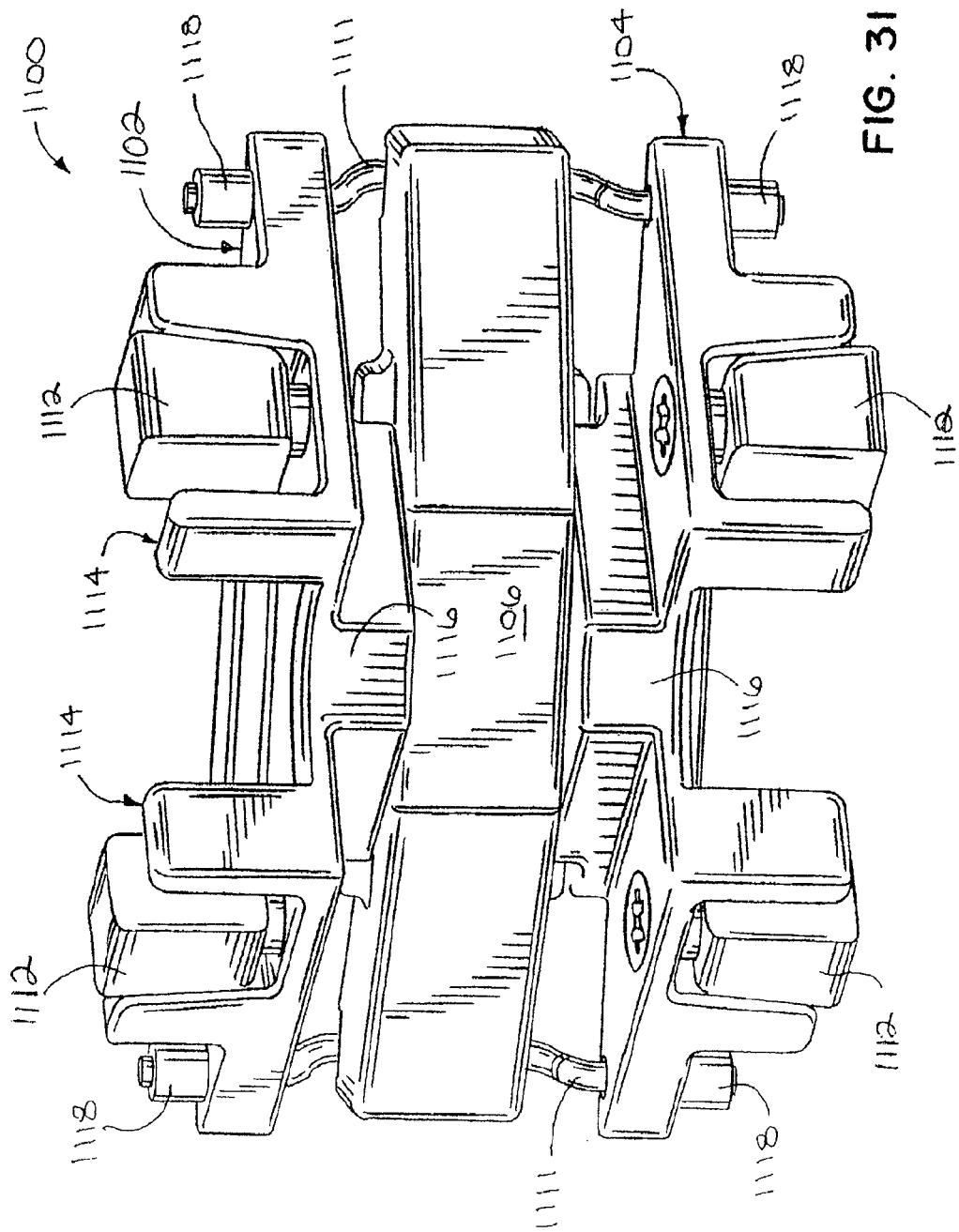
FIG. 31 is an enlarged anterior perspective view of the spinal stabilization system of FIGS. 29 and 30 showing C-shaped portions of the engagement members including threaded fasteners securing block-shaped dampers therein and gripping regions adapted to engage laminar regions of the vertebrae to minimize relative movement therebetween.

FIGS. 29-31 depict a spinal stabilization system 1100 according to an eleventh form of the present invention. Spinal stabilization system 1100 is very similar to spinal stabilization system 800 depicted in and described with reference to FIGS. 20-22 in that it includes a first engagement member 1102, a second engagement member 1104, and a support structure having a resilient body 1106, and a pair tensioning members 1108; therefore, only the differences will be described herein in detail. The difference between spinal stabilization system 1100 and spinal stabilization system 800 is that the tensioning members 1108 of spinal stabilization system 1100 include substantially cylindrical arch-shaped members 1111 rather than plate shaped members 806. Specifically, each of the cylindrical members 1111 may include a length of cord such as cable affixed to the first and second engagement members with fastening members 1118 identical to any of the fastening members described hereinabove. Alternatively, the cylindrical members 1111 may include metallic wire. Otherwise, the spinal stabilization system 1100 is structurally and functionally identical to spinal stabilization system 800. Specifically, a compressive load applied to either or both of the superior and inferior vertebrae 1a, 1b is transferred directly to engagement members 1102, 1104. This places the resilient body 1106 in compression and the tensioning members 1108 in slight tension. Therefore, the resilient body 1106 and the tensioning members 1108 counteract the compressive load on the vertebrae 1a, 1b to maintain the intervertebral spacing.

For example, the first and second engagement members 1102, 1104 include base plates 1110 and dampers 1112. Each of the base plates 1110 of the engagement members 1102, 1104 include opposing C-shaped portions 1114 interconnected by truss portions 1116. The dampers 1112 are generally cubicle members disposed within the opposing C-shaped portions 1114 of the base plates 1110. The resilient body 1106 is disposed axially between the first and second engagement members 1102, 1104 and is constructed of a generally elastic deformable material such as rubber. However, it should be understood that the resilient body 1106 may be formed of any resilient material such as foam, a polymer, copolymer, or any other suitable material capable of serving the principles of the present invention. In one form, the resilient body 1106 is attached to the first and second engagement members 1102, 1104 with an adhesive. In alternate form, the resilient body 1106 may be attached to the first and second engagement members 1102, 1104 with fasteners such as screws, rivets or the like. In yet another alternative form, the resilient body 1106 may not be connected to the first and second engagement members 1102, 1104 at all, but rather, maintained disposed therebetween by a compressive load generated by the tensioning members 1108. The pair of arch-shaped tensioning members 1108 extends axially between and connects the first and second engagement members 1102, 1104. Additionally, the arch-shaped tensioning members 1108 include a pair of locking fasteners 1118. The locking fasteners 1118 attach to the opposing ends of the pair arch-shaped tensioning members 1108 and set the tension applied by the tensioning members 1108 to the first and second engagement members 1102, 1104. Additionally, lateral extending portions of the resilient body 1106 are accommodated by the cylindrical arch-shaped members 1111 of the tensioning members 1108. So configured, the first and second engagement members 1102, 1104 receivingly accommodate laminar regions 11 of adjacent vertebra. Additionally, it should be appreciated that the implantation during surgery of the spinal stabilization system 1100 depicted in FIGS. 16 and 17 is substantially identical to that which was described above regarding the implantation of the spinal stabilization system 1000, depicted in FIGS. 26-28.

Figure 32:
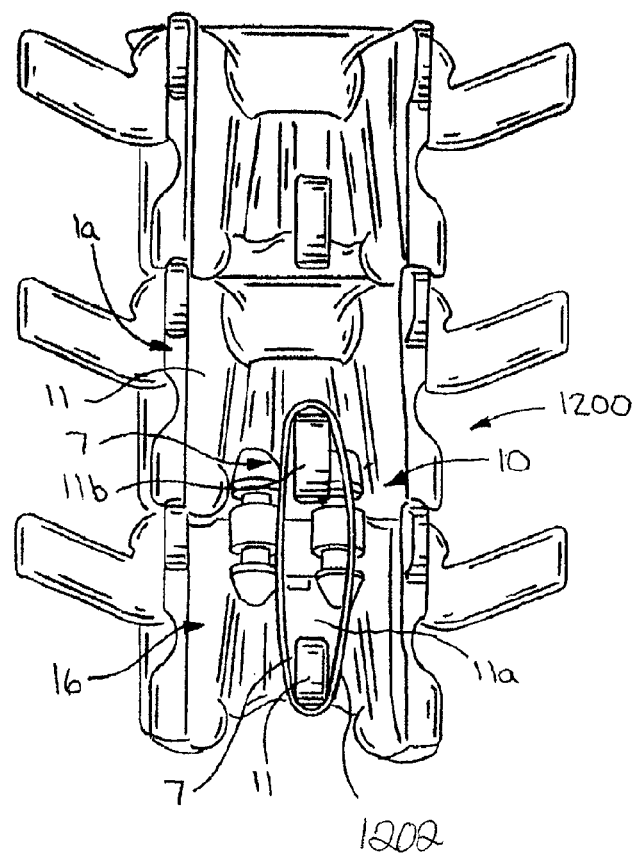
FIG. 32 is a perspective view of a spinal stabilization system according to a twelfth form of the present invention including a first engagement member abuttingly engaging a laminar region of a first vertebra, a second engagement member abuttingly engaging a laminar region of a second vertebra, and an axial retention band disposed about spinous processes of the first and second vertebrae.
Figure 33:
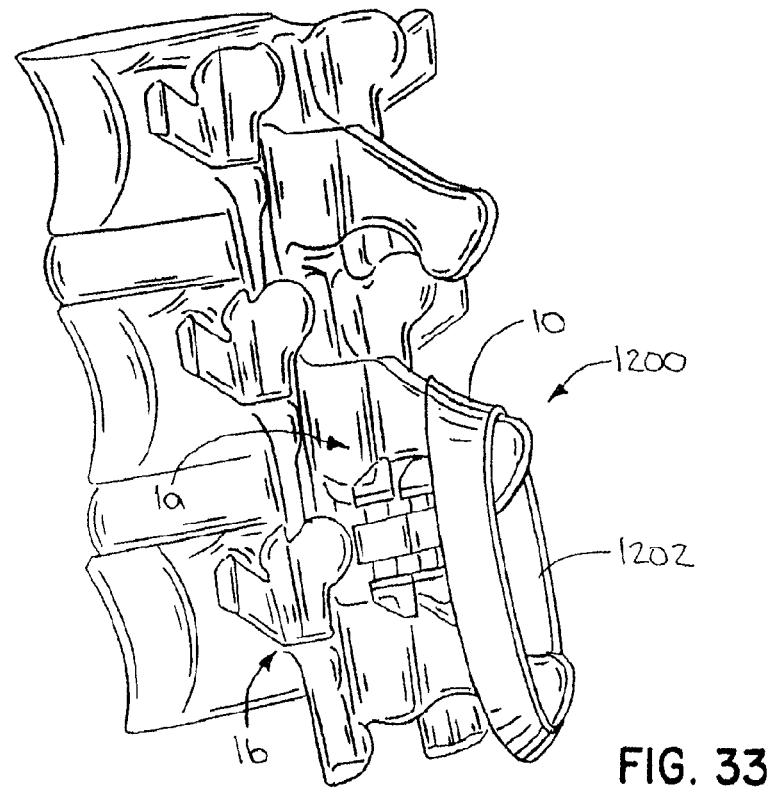
FIG. 33 is another perspective view of the spinal stabilization system according to the twelfth form of the present invention depicted in FIG. 32.

FIGS. 32 and 33 depict a spinal stabilization system 1200 according to a twelfth form of the present invention. The spinal stabilization system 1200 includes a spinal stabilization system 10 identical to that described above with reference to FIGS. 1 and 2 supplemented with an axial retention member 1202. The spinal stabilization system 10 functions identically to that described above, while the axial retention member 1202 provides a compressive load to the spinous processes 7 of both the superior and inferior vertebrae 1a, 1b. Specifically, a tensile load applied to either or both of the superior or inferior vertebrae 1a, 1b is transferred directly to the axial retention member 1202 via the spinous processes 7. The axial retention member 1202 is thereby placed in tension and counteracts the tensile load to minimize any distraction of the vertebrae 1a, 1b. Therefore, the combination of the spinal stabilization device 10 and the axial retention member 1202 serves to both minimize reduction in the intervertebral spacing between the superior and inferior vertebrae 1a, 1b, as well as to minimize distraction of the superior and inferior vertebrae 1a, 1b.

It should be understood that because the spinal stabilization system 10 included as a part of the entire spinal stabilization system 1200 depicted in FIGS. 32 and 33 is identical to that described above with reference to FIGS. 1 and 2, such will not be described in detail herein. The axial retention member 1202, however, in the form illustrated, includes a resilient band type component, such as a relatively wide rubber band or elastic band. As stated above, the spinal stabilization system 10 serves primarily to prevent reduction of the intervertebral space between the adjacent vertebrae. Therefore, the axial retention member 1202 of the spinal stabilization system 1200, which extends around spinous processes 7 of the adjacent vertebrae and provides a compressive load thereto, serves to minimize distraction of the adjacent vertebrae. In this manner, the spinal stabilization system 1200 effectively limits both reduction of the intervertebral spacing and distraction of the adjacent vertebrae. During implantation, the surgeon first installs the spinal stabilization system 10 as described above with reference to FIGS. 1 and 2 and, subsequently installs the axial retention member 1202. Implantation of the axial retention member 1202 simply involves providing a tension force thereto, i.e., stretching the band member 1202, and fitting it about the spinous processes 7 of the adjacent vertebrae. After releasing the retention member 1202, the axial retention member 1202 elastically returns toward its original form to provide the compressive forces on the vertebrae.

Figure 34:
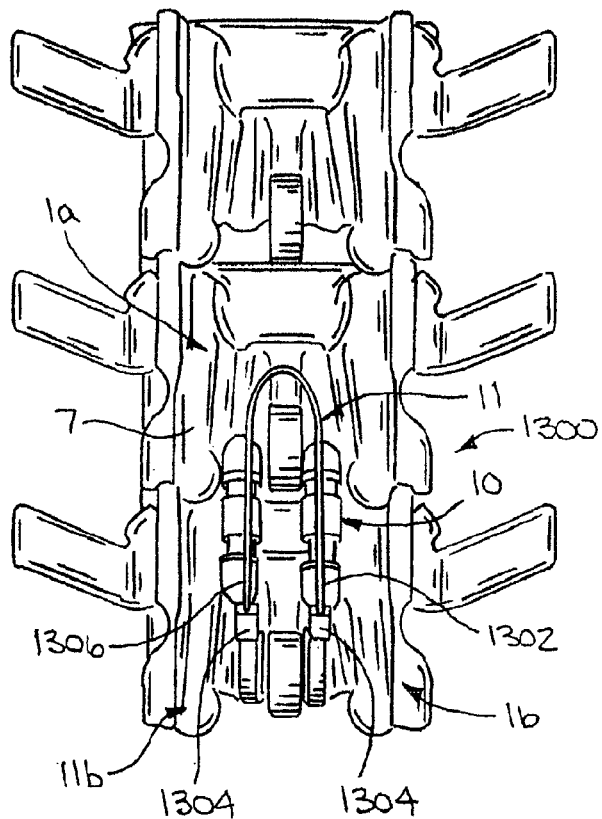
FIG. 34 is a perspective view of a spinal stabilization system according to a thirteenth form of the present invention including a first engagement member in abutting engagement with a laminar region of a first vertebra, a second engagement member in abutting engagement with a laminar region of a second vertebra, a retention member including a pair of hooks engaging the laminar region of the second vertebra opposite the second engagement member and a cord extending between the hooks and around the spinous process of the first vertebra.
Figure 35:
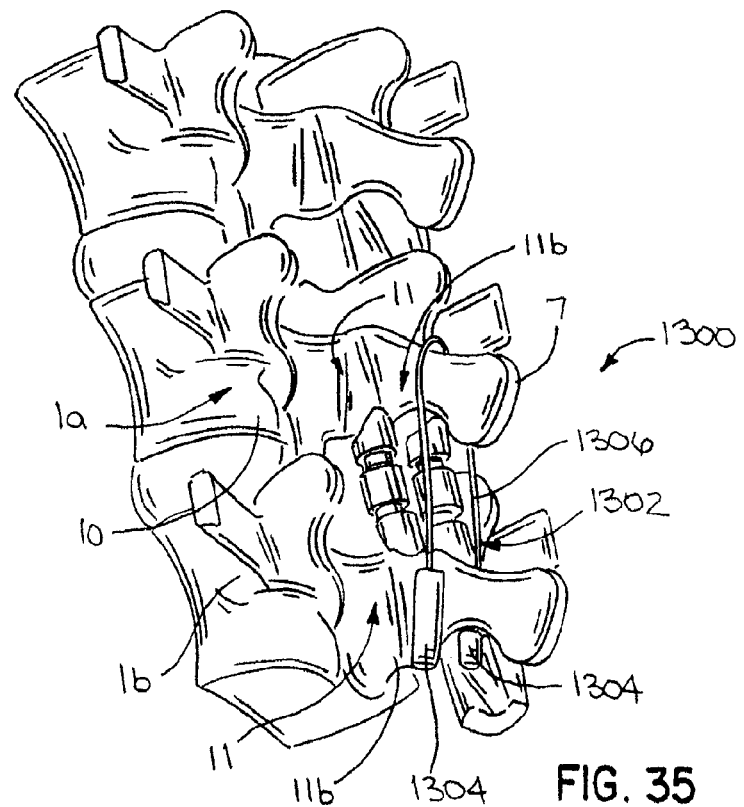
FIG. 35 is another perspective view of the spinal stabilization system according to the thirteenth form of the present invention depicted in FIG. 34.
Figure 36:
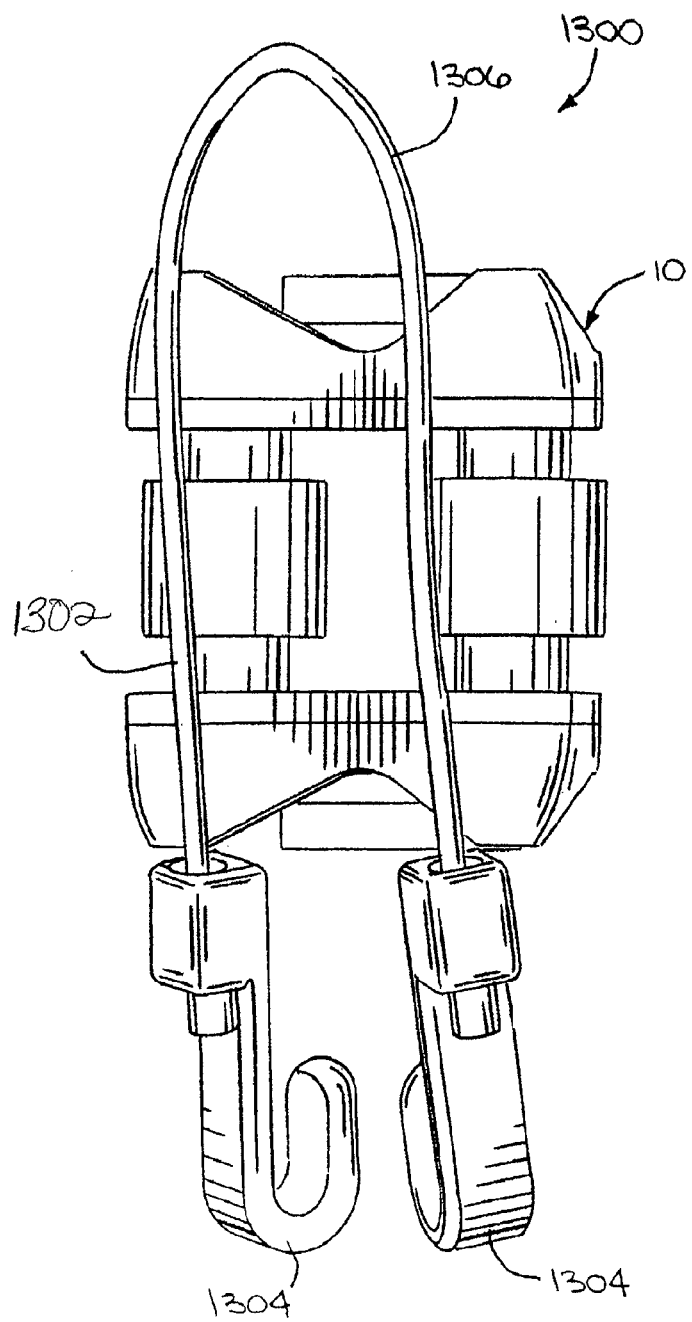
FIG. 36 is an enlarged posterior perspective view of the spinal stabilization system of FIGS. 34 and 35 showing the shape of the hooks of the retention member adapted to hook onto the laminar region of the vertebra.

FIGS. 34-36 depict a spinal stabilization system 1300 including a spinal stabilization system 10 identical to that which was described above with reference to FIGS. 1 and 2 supplemented with an axial retention member 1302. The spinal stabilization system 10 functions identically to that described above, while the axial retention member 1302 provides a compressive load to the spinous processes 7 of the superior vertebra 1a and to the laminar region of the inferior vertebra 1b. Specifically, a tensile load applied to either or both of the superior or inferior vertebrae 1a, 1b is transferred directly to the axial retention member 1302 via the spinous processes 7 of the superior vertebra 1a or the laminar region 11 of the inferior vertebra 1b. The axial retention member 1302 is thereby placed in tension and counteracts the tensile load to minimize any distraction of the vertebrae 1a, 1b. Therefore, the combination of the spinal stabilization device 10 and the axial retention member 1302 serves to both minimize reduction in the intervertebral spacing between the superior and inferior vertebrae 1a, 1b, as well as to minimize distraction of the superior and inferior vertebrae 1a, 1b.

The axial retention member 1302 includes a pair of hooks 1304 and a cord 1306. As stated above, the spinal stabilization system 10 serves to limit reduction of the intervertebral spacing. The axial retention member 1302, therefore, serves primarily to limit distraction of the adjacent vertebrae. Specifically, the hooks 1304 are interconnected by the cord 1306 and secured thereto with locking fasteners similar to those described above with reference to the ninth, tenth and eleventh forms. The cord 1306 is, in one form, constructed of an elastic material. In an alternative form, the cord 1306 is constructed of a metallic material such as metal wire or cable. So constructed, the hooks 1304 engage about the inferior edge 11b of the laminar region 11 of the vertebra opposite the spinal stabilization system 10, as depicted in FIGS. 34 and 35. The cord 1306 extends upwardly from one hook 1304 is looped around the spinous process 7 of the vertebra that is superior to the spinal stabilization system 10 and terminates at the other hook 1304. Preferably, the cord 1306 includes a length that is of sufficient size to provide an appropriate amount of compressive load between the laminar region 11 of the inferior vertebra 1b and the spinous process 7 of the superior vertebra 1a.

During surgery, the surgeon installs the spinal stabilization system 10 identically to that described above with reference to FIGS. 1 and 2. Additionally, however, the surgeon must also install the axial retention member 1302. To install the axial retention member 1302, a surgeon first engages the hooks 1304 about the inferior edges 11b of the laminar region 11 of the inferior vertebra 1b, as depicted in FIGS. 34 and 35. In one form, the cord 1306 includes an elastic material that is prefabricated and attached to the hooks 1304. Thus, to complete implantation of the axial retention member 1302, a surgeon need only take a center portion of the cord 1306 and stretch it over the spinous process 7 of the superior vertebra 1a. In an alternate form that includes a non-elastic cord 1306, the surgeon may be required to attach a first end to one of the hooks 1304, wrap the cord 1306 around the superior spinous process 7, and then attach the other end to the other hook 1304. Such attachment would be accomplished with locking fasteners identical to those described above such as press-fit fasteners, cable crimps, threaded fasteners, or any other type of fastener capable of serving the principles of the present invention.

Figure 37:
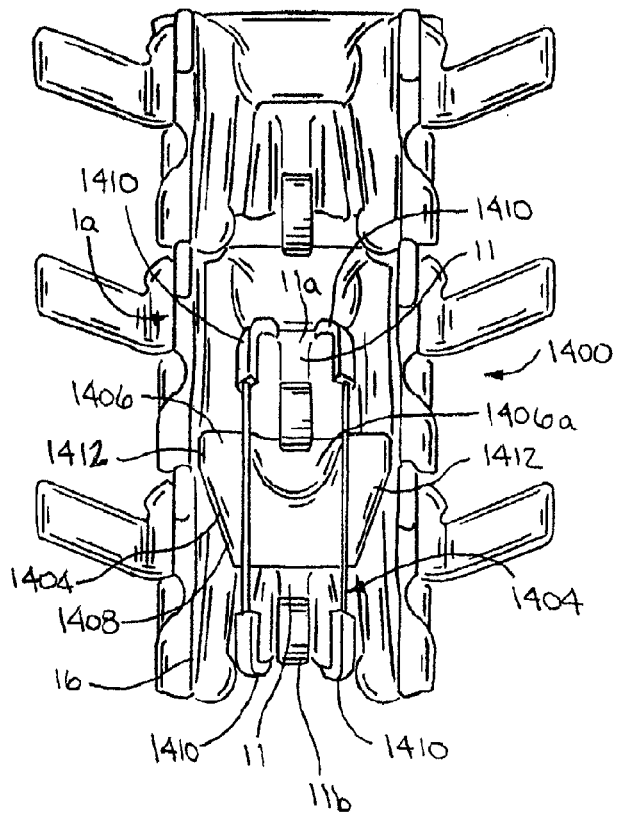
FIG. 37 is a perspective view of a spinal stabilization system according to a fourteenth form of the present invention including a resilient body disposed between a laminar region of a first vertebra and a laminar region of a second vertebra, and a pair of retention members each comprising a first hook engaging a superior edge of the laminar region of the first vertebra and a second hook engaging an inferior edge of the laminar region of the second vertebra and a tensioning cord disposed between the hooks.
Figure 38:
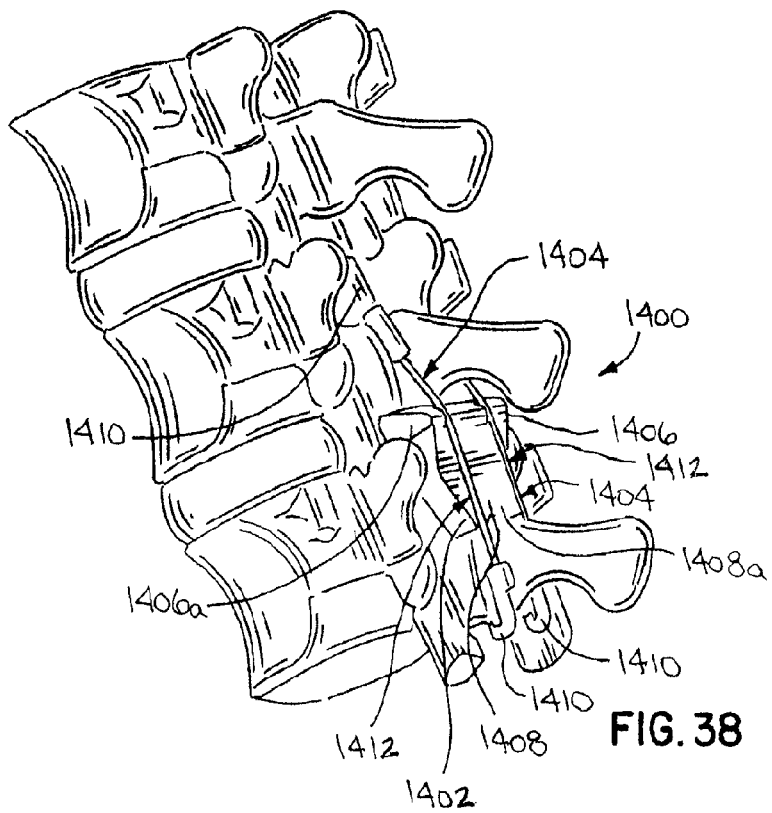
FIG. 38 is another perspective view of the spinal stabilization system according to the fourteenth form of the present invention depicted in FIG. 37.
Figure 39:
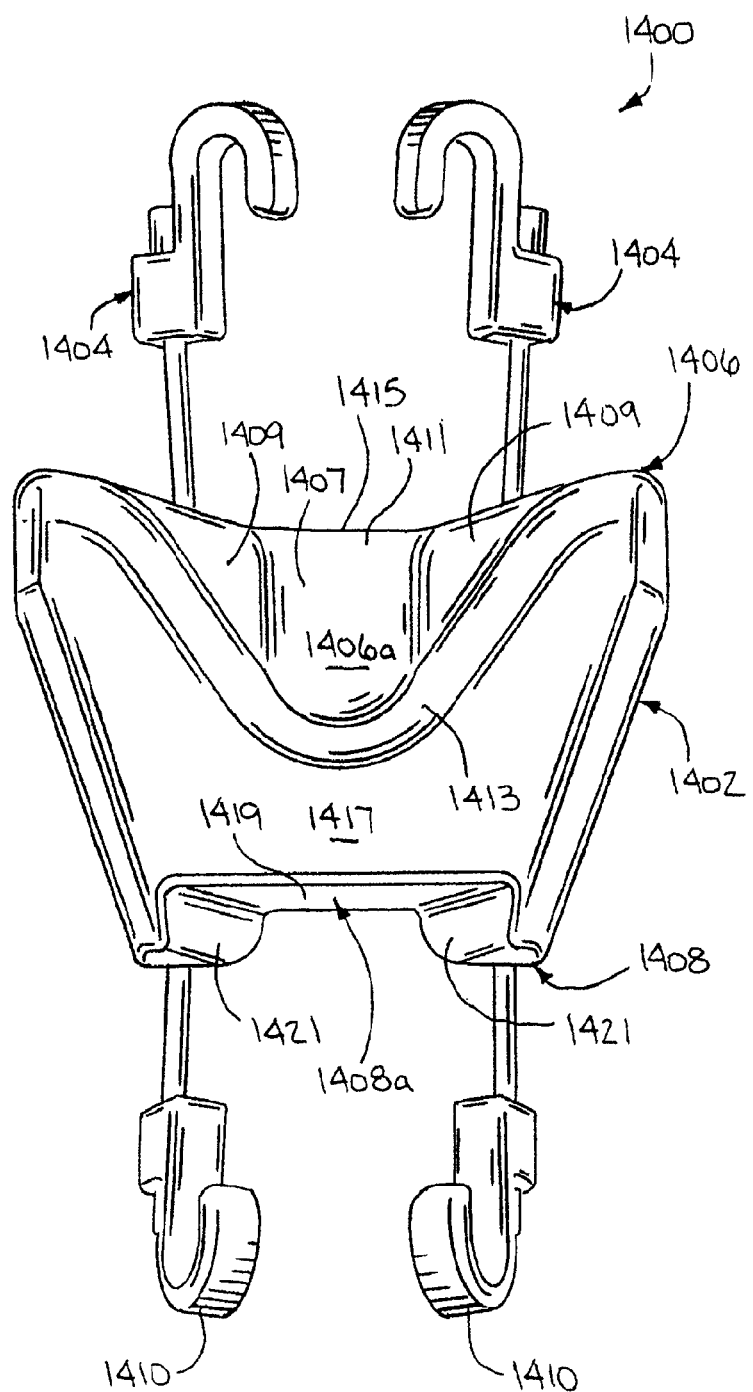
FIG. 39 is an enlarged anterior perspective view of the spinal stabilization system of FIGS. 37 and 38 showing a superior concave surface adapted to receive an inferior edge of a laminar region of a superior vertebra and an inferior concave surface adapted to receive a superior edge of a laminar region of an inferior vertebra.

FIGS. 37-39 depict a spinal stabilization system 1400 in accordance to a fourteenth form of the present invention. The spinal stabilization system 1400 includes an engagement member comprising at least a portion of a body 1402 and a support structure comprising at least a portion of the body 1402 and a pair of axial retention members 1404. The body 1402 is engagingly disposed within the intervertebral spacing between a superior vertebra 1a and an inferior vertebra 1b. The body 1402 counteracts compressive forces applied to the spine to maintain the intervertebral spacing. Specifically, a compressive load applied to either or both of the superior and inferior vertebrae 1a, 1b is transferred directly to the body 1402 via the laminar regions 11 of the vertebrae 1a, 1b. This places the body 1402 under a compressive load, which the body counteracts to minimize reduction in the intervertebral spacing. Additionally, the axial retention members 1404 each connect and apply a compressive load to the laminar regions 11 of the superior and inferior vertebrae 1a, 1b to minimize distraction. Specifically, a tensile load applied to either or both of the superior or inferior vertebrae 1a, 1b is transferred directly to the axial retention member 1404 via the laminar regions 11 of the superior and inferior vertebrae 1a, 1b. The axial retention member 1404 is thereby placed in tension and counteracts the tensile load to minimize any distraction of the vertebrae 1a, 1b. Therefore, the combination of the body 1402 and the axial retention member 1404 serves to both minimize reduction in the intervertebral spacing between the superior and inferior vertebrae 1a, 1b, as well as to minimize distraction of the superior and inferior vertebrae 1a, 1b.

In the form illustrated, the body 1402 includes a three-dimensional body having a generally trapezoidal elevation with a broad upper portion 1406 and a narrower lower portion 1408. The broad upper portion 1406 includes a complex concave surface 1406a (shown in detail in FIG. 39) for receiving the posterior surface 11d of the inferior edge 11b of the laminar region 11 of the superior vertebra 1a depicted in FIG. 37. The narrow lower portion 1408 includes a central, recessed portion 1408a (also shown in detail in FIG. 39) for receiving a superior edge 11a of the laminar region 11 of the inferior vertebra 1b depicted in FIG. 37.

As mentioned above, the concave surface 1406a of the broad upper portion 1406 is adapted and configured to receive the inferior edge 11b of the laminar region 11 of the superior vertebra 1a in engagement therewith. With reference to FIG. 39, the concave surface 1406a includes a central panel 1407 flanked by a pair of generally triangular side panels 1409. Additionally, each of the panels 1407, 1409 transition to a superior edge 1415 of the body 1402 via a rounded surface 1411. Similarly, each of the panels 1407, 1409 transition to an anterior surface 1417 of the body 1402 via a rounded surface 1413. These rounded or smooth transitional surfaces 1411, 1417 are intended to more closely emulate the natural construction of the posterior surface 11d near the inferior edge 11b of the laminar region 11 of the corresponding vertebra to ensure a close abutment therewith. Additionally, the superior edge 1415 of the body 1402 abuttingly engages the inferior edge 11b to counteract any compressive forces applied thereto. While the concave surface 1406a has been described herein as including a central panel being flanked by side panels, an alternate form of the invention may include a concave surface that smoothly transitions between the various regions thereof without necessarily including any distinct panels. In yet another alternate form, the concave surface 1406a may be something in which a surgeon him or herself form into the body 1402 during surgery only after taking precise measurement of a patient's vertebra. Such a procedure would enhance the accuracy of the fit between the body 1402 and the vertebra.

As is also mentioned above, the recessed portion 1408a of the lower narrow portion 1408 of the body 1402 is adapted or configured to receive a superior edge of a laminar region 11 of the inferior vertebra 1b, as in FIGS. 37 and 38. With reference to FIG. 39 and continued reference to FIGS. 37 and 38, the recessed portion 1408a includes a top surface 1419 and opposing side surfaces 1421. The top surface 1419 abuttingly engages the superior edge 11a of the laminar region 11 of the inferior vertebra 1b to maintain the axial disposition of the body 1402 and counteract any compressive forces applied to the inferior and superior vertebra 1b, 1a.

The axial retention members 1404 each include a pair of hooks 1410a and 1410b interconnected by a tensioning member 1412 and secured thereto by locking fasteners. The upper hook 1410a is adapted to receivingly engage the superior edge 11a of the laminar region 11 of the superior vertebra 1a, as depicted in FIGS. 37 and 38. The lower hook 1410b is adapted to receivingly engage on inferior edge 11b of the laminar region 11 of the inferior vertebra 1b. The tensioning member 1412 has opposing ends correspondingly attached to the pair of hooks 1410. The tensioning member 1412, in one form, includes a cable. In an alternate form, however, the tensioning member 1412 may include an elongated wire formed of a metallic or polymer elastic material. Hence, the spinal stabilization system 1400 serves both to minimize any reduction in the intervertebral spacing by way of the body 1402, as well as minimize any distraction of the adjacent vertebrae by way of the retention members 1404.

During surgery, the body 1402 is first inserted between the adjacent vertebrae. Subsequently, in one form, the hooks 1410 on first ends of the tensioning members 1412 are hooked on the superior edge 11a of the laminar regions 11 of the superior vertebra 1a. Then, in the case where the tensioning members 1412 are elastic, the surgeon need only stretch the tensioning members 1412 downward to hook the other hooks 1410 on the inferior edge 11b of the laminar region 11 of the inferior vertebra 1b. In an alternate form having generally rigid or fixed length tensioning members 1412, the surgeon may additionally be required to attach the hooks 1410 thereto during surgery.

Referring to FIGS. 47 to 51 a fifteenth embodiment of a spinal stabilization system 1502 is illustrated in the form of a laminar support member 1504 or jack that may include a one piece, two piece, or three piece implant that is configured to be inserted between laminar regions 11 on adjacent vertebrae 1a and 1b. The laminar support member 1504 preferably includes a resilient member (such as polyurethane or other similar resilient material) that is configured to be compressed (FIG. 50) and distracted (FIG. 49) by an actuator or adjustment mechanism 1505 arranged and configured to transform the support member between the compressed and distracted conditions by manipulating an elongate member 1506 extending through the laminar support member 1504.

The resilient material used to form the laminar support member 1504 is advantageous because it provides a conformable upper and lower surface thereof for matching the varying anatomies of different patient's spines. The expansion of the resilient material also provides for a solid grip on the lamina, which is beneficial to minimize, and preferably prevent, movement and/or expulsion of the implant.

Figure 47:
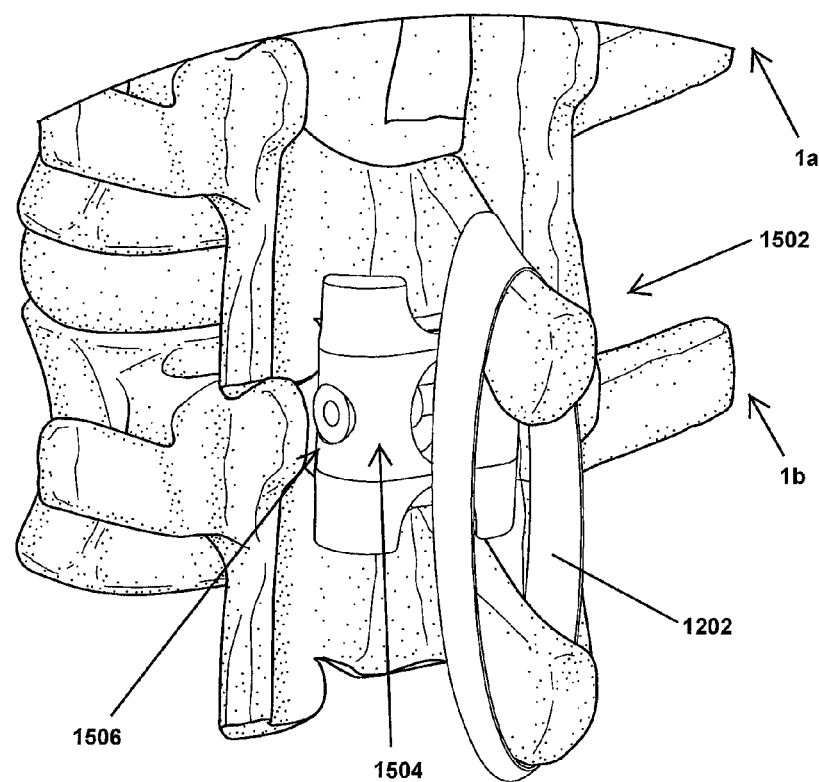
FIG. 47 is a perspective view of a spinal stabilization system according to a fifteenth form of the present invention including a laminar spacer that is shifted from a contracted or compressed configuration to a distracted configuration and an optional axial retention band.
Figure 48:
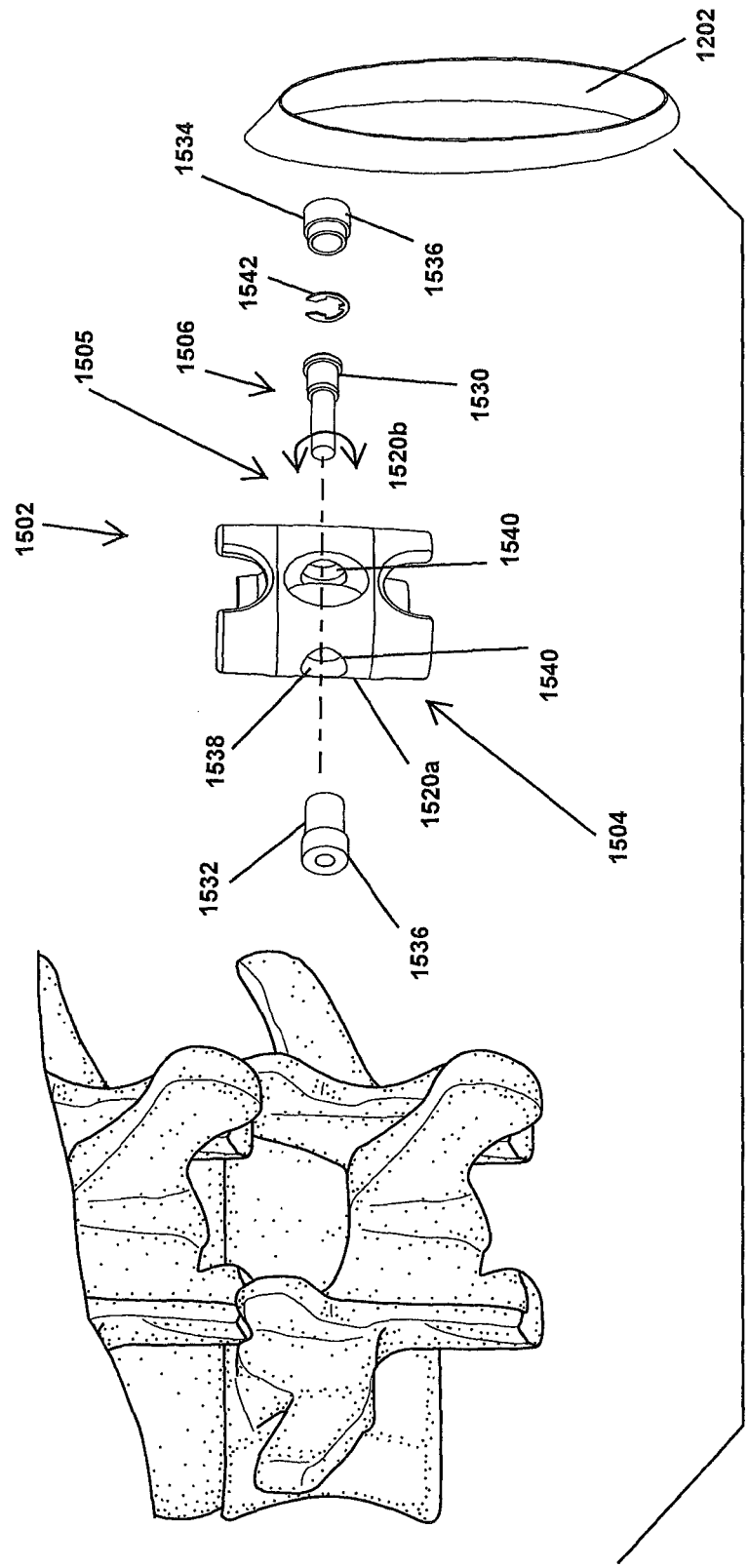
FIG. 48 is an exploded view of the spinal stabilization system of FIG. 47 showing an actuating or adjustment mechanism including a jack screw, a receiving member, and a bearing member.

As shown in FIGS. 47 and 48, the system 1502 may optionally include the axial retention band 1202 to provide unloading of pressure on the anterior of the spine similar to other embodiments that incorporate the band. However, the system 1502 may also be used without the retention band 1202.

Figure 49:
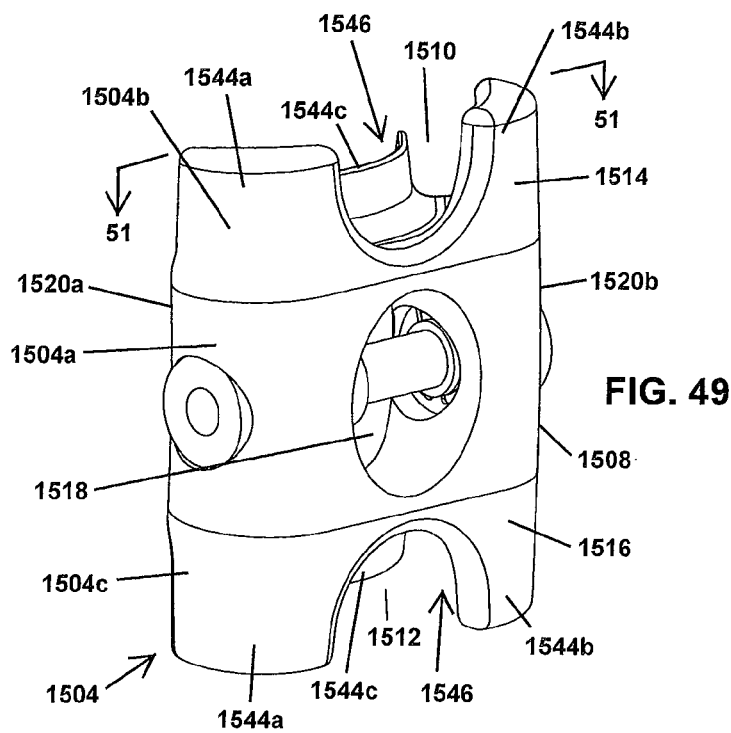
FIG. 49 is a perspective view of the laminar spacer of FIG. 47 shown in a distracted or expanded configuration.
Figure 50:
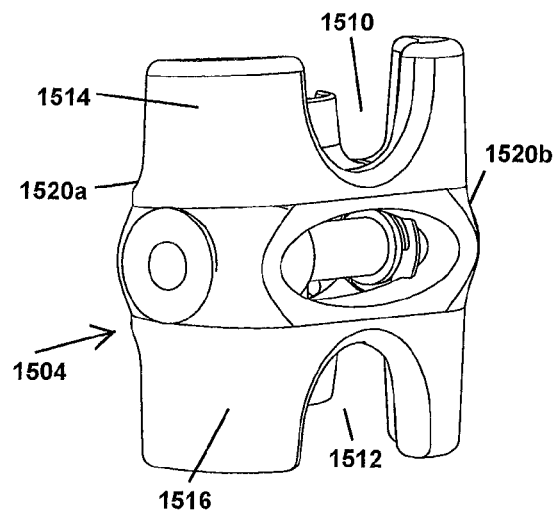
FIG. 50 is a perspective view of the laminar spacer of FIG. 47 shown in a contracted configuration.

In use, the laminar support member 1504 is inserted between the laminar regions 11 on adjacent vertebrae 1a and 1b in the compressed state (FIG. 50). Once properly received between the adjacent vertebrae, the elongate member 1506 is manipulated (such as by rotating) to expand or distract the support member 1504 into engagement with the laminar regions 11 of the adjacent vertebrae 1a and 1b (e.g., FIGS. 47 and 49). As a result, the laminar support member 1504 is then positioned to counteract any compressive loads applied to the adjacent vertebrae and also maintain an appropriate intervertebral spacing therebetween.

Figure 51:
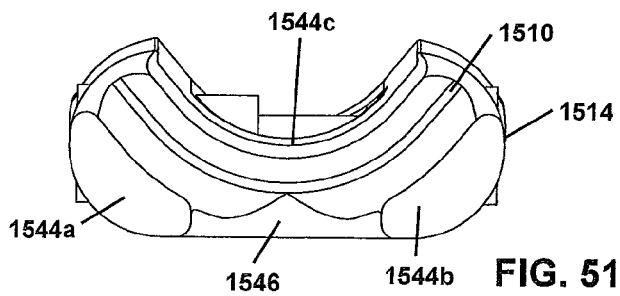
FIG. 51 is a top plan view of the laminar spacer of FIG. 47 showing a saddle surface portion thereof for mating with a laminar region.

Turning to the details, the laminar support member 1504 includes a resilient member 1508, which in one form is a unitary member formed from the resilient material. The resilient member 1508 includes saddle seating portions 1510 and 1512 formed on an upper end 1514 and a lower end 1516, respectively. As illustrated in FIG. 51, the seating portion 1510 has a generally arcuate shape in order to permit one of the laminar regions 11 to rest therein. The other saddle seating portion 1512 has a similar configuration.

The resilient member 1508 also includes a through hole 1518 generally extending in an anterior-posterior direction that permits the support member 1504 to resiliently deform from the compressed configuration of FIG. 50 to the expanded configuration of FIG. 49. For instance, the hole 1518 has a oblong or generally elliptical configuration to deform the support member 1504 into the contracted or compressed configuration because the adjustment mechanism is expanded in a lateral direction to force opposite side 1520a and 1520b away from each other. By compressing or retracting the elongate member 1506, opposite sides 1520a and 1520b are drawn toward each other to cause the member 1504 to deform into the expanded configuration of FIG. 49. In this state, the through hole 49 has a more circular shape.

As best shown in FIG. 48, the adjustment mechanism 1505 of the laminar support member 1504 includes a cylindrical jack screw member 1530 that is threadably mated with a receiving member 1532 (preferably a threaded nut) on one end of the screw member 1530. On the other end of the screw member 1530, an insert or bearing member 1534 is provided through with the screw member 1530 is rotatably inserted. Both the receiving member 1532 and insert 1534 have an outer flange portion 1536 that abut with a seating surface 1538 provided on a secondary through hole 1540 that extend in the lateral direction in the support member 1504 through which the screw member 1530 is rotatably inserted. Optionally, a retaining member 1542 in the form of a C-clip may also be used to secure the screw member 1530 to the insert 1534. As the screw member 1530 is rotated it is threaded into the receiving member 1532 and the flange portions 1536 then draw the support member outer edges 1520a and 1520b toward each other to transform the resilient member 1508 from the compressed to the distracted state.

As best shown in FIGS. 49-51, the resilient member 1508 includes extensions 1544a, 1544b, and 1544c that define the saddle surfaces 1510 and 1512. Preferably, the extensions 1544a and 1544b and on the posterior side of the member 1504 and are spaced apart so as to form a generally U-shaped slot 1546 therebetween sized and configured to received a portion of the spinous process 7 when inserted between adjacent vertebrae. The extension 1544c is generally on an anterior side of the member 1508.

Alternatively, the laminar support member 1504 may include two or three pieces, such as that illustrated in FIG. 49. In this form, the member 1504 may include a middle portion 1504a formed from the resilient material, a top portion 1504b formed from a second material, such as PEEK (or other biocompatible materials) or a resilient material, and a bottom portion 1504c formed from a third material, such as PEEK (or other biocompatible materials) or a resilient material. The three portions are preferably secured together in a manner that permits the resilient middle portion 1504a to transform from the compressed to the distracted states.

Figure 52:
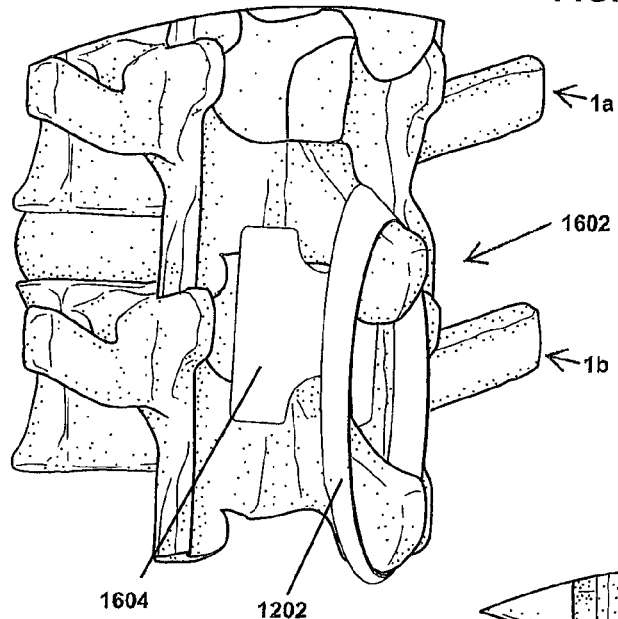
FIG. 52 is a perspective view of a spinal stabilization system according to a sixteenth form of the present invention including a laminar spacer that is wedged between the laminar regions of adjacent vertebrae.
Figure 53:
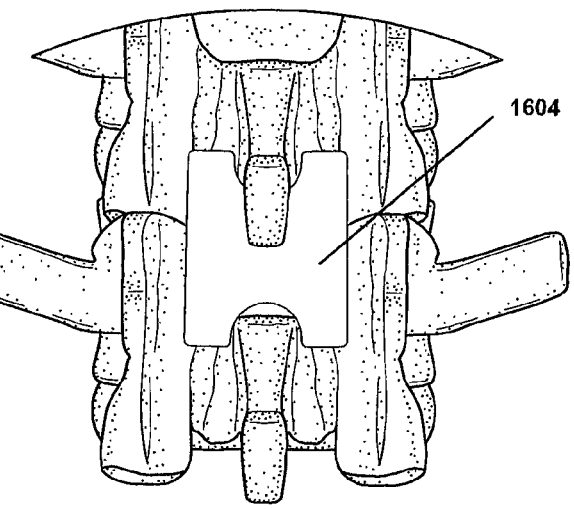
FIG. 53 is a elevational view of the spinal stabilization system of FIG. 52 showing its relationship to the adjacent vertebrae.
Figure 54:
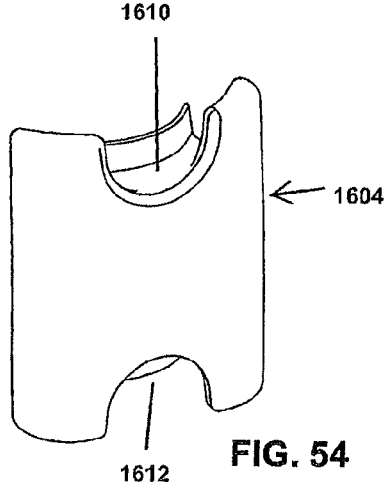
FIG. 54 is a perspective view of the laminar spacer of FIG. 52 showing a saddle seating portion thereof for mating with a laminar region.

Referring to FIGS. 52-53, a sixteenth embodiment of a spinal stabilization system 1602 is illustrated in the form of a solid laminar support member 1604 formed from a resilient material, such as polyurethane. The support member 1504 is also shown with the optional axial support band 1202. This support member 1604 is similar to the previously described support member 1504, but is a solid member without the previously described apertures for enabling compressing and distracting. Rather, this form of the support member 1604 is compressed by the surgeon manually during implantation by squeezing on the opposing saddle seating surfaces 1610 and 1612 to deform the support member a sufficient amount to insert between laminar regions 11 of adjacent vertebrae 1a and 1b. Once inserted, the surgeon releases the saddle portions, and due to the resilient material of the support member, it transforms back to its original condition to engage the vertebrae laminar regions.

Figure 55:
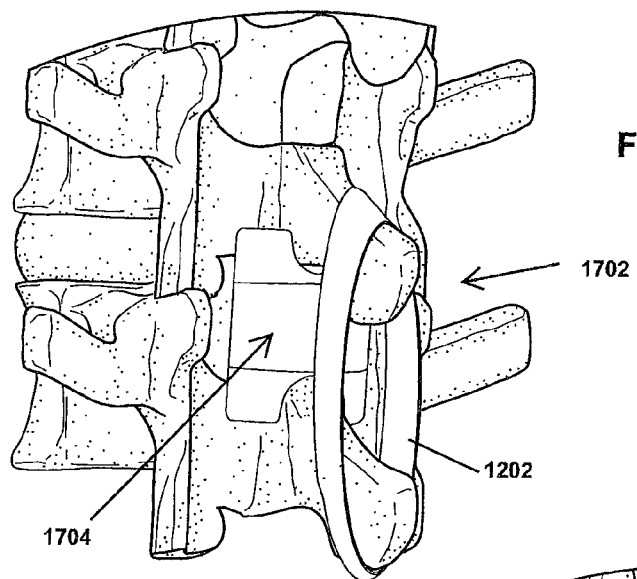
FIG. 55 is a perspective view of a spinal stabilization system according to a seventeenth form of the present invention including a laminar spacer that is wedged between the laminar regions of adjacent vertebrae.
Figure 56:
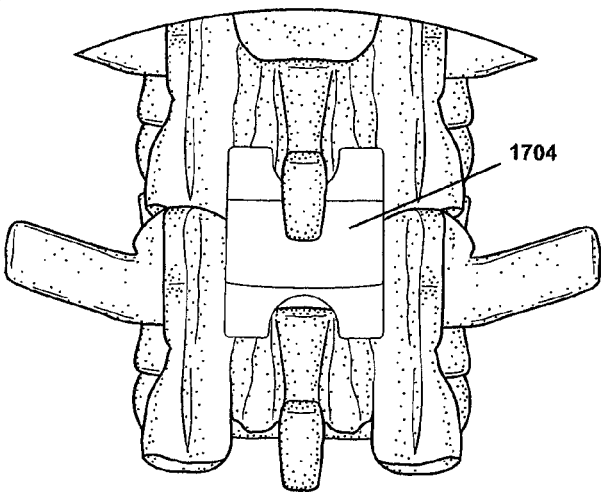
FIG. 56 is a elevational view of the spinal stabilization system of FIG. 55 showing its relationship to the adjacent vertebrae.
Figure 57:
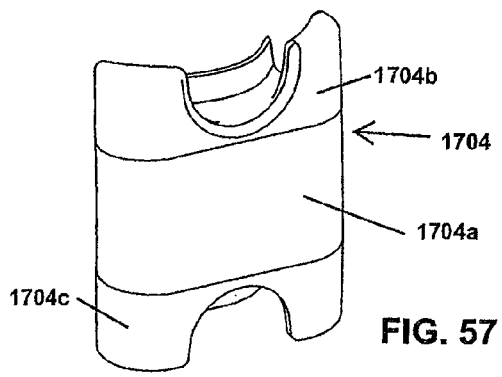
FIG. 57 is a perspective view of the laminar spacer of FIG. 55 showing a saddle seating portion thereof for mating with a laminar region.
Figure 58:
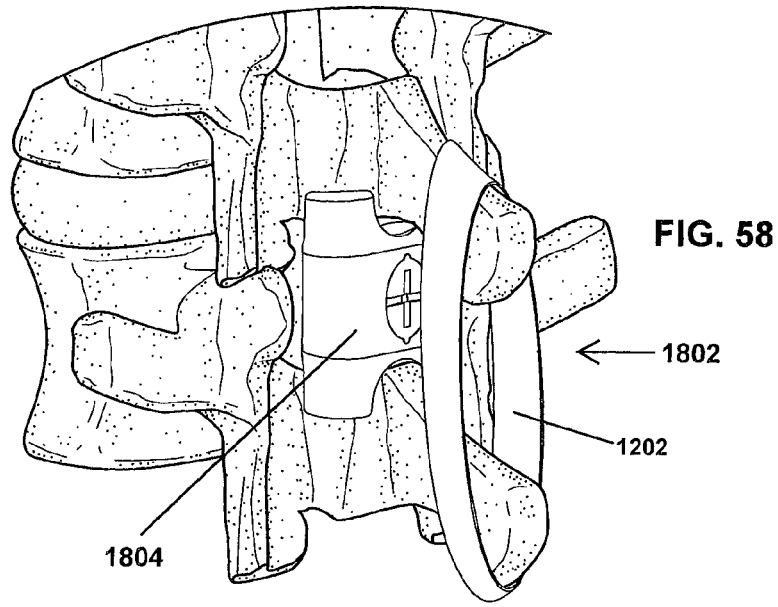
FIG. 58 is a perspective view of a spinal stabilization system according to a eighteenth form of the present invention including a laminar spacer that is wedged between the laminar regions of adjacent vertebrae and is configured to expand and distract upon rotating an elliptical spacer member extending through an aperture in the laminar spacer.
Figure 59:
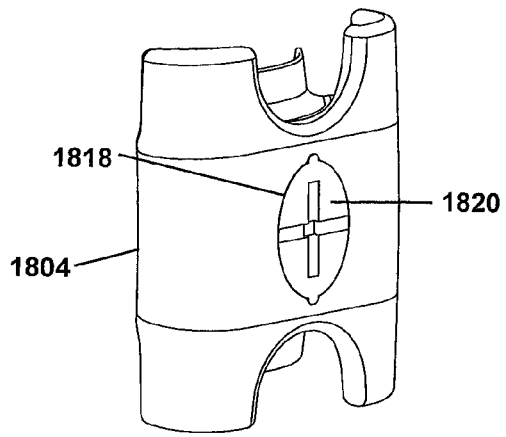
FIG. 59 is a perspective view of the laminar spacer showing the elliptical spacer received in the aperture.

Referring to FIGS. 55-57, a seventeenth embodiment of a spinal stabilization system 1702 is illustrated in the form of a three-piece, solid laminar support member 1704 formed from both a resilient material, such as polyurethane and the like, and a more rigid material, such as PEEK or other biocompatible material. This embodiment is similar to the previously described solid support member 1604, but instead includes a middle portion 1704a formed from the resilient material, and opposing end portions 1704b and 1704c formed from the more rigid material. Preferably, the three portions are secured together in a manner so that the resilient portion can deform during insertion as described with the previous embodiment. The system 1702 is also shown with the optional axial retention band 1202, but can also be used without such supplemental device.

Referring to FIGS. 58-62, an eighteenth embodiment of a spinal stabilization system 1802 is illustrated in the form of a one, two, or three piece laminar support member 1804 having an actuator or adjustment mechanism 1805 included therewith that transforms the device from a compressed condition (FIG. 62) to a distracted or expanded condition (FIGS. 58-61). The support member 1804 is similar to the previous described embodiments and can be formed from a one piece, resilient material (such as polyurethane or the like) or can be formed from two or three components (three are shown) in which a middle portion 1804a is formed from the resilient material, and either one or both of outer portions 1804b and 1804c are formed from either a more rigid material (such as peek or the like) or a resilient material (such as polyurethane or the like).

Figure 60:
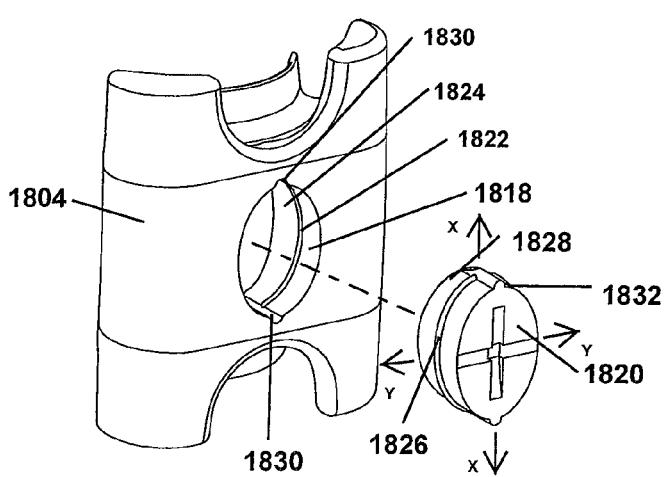
FIG. 60 is an exploded view of the laminar spacer and elliptical spacer.

The adjustment mechanism 1805 includes a through hole 1818 that extends through the body of the support member in a anterior-posterior direction. Rotatably received in the through hole 1818 is a plug member 1820 that has a shape effective to transform the support member 1804 from the compressed (FIG. 62) to the distracted condition (FIG. 61) upon the plug member 1820 being manipulated (i.e., rotated). In one form, the plug member 1820 has an elliptical shape with an X-axis longer than an Y-axis (FIG. 60). In this manner, by positioning the plug member 1820 in the through hole 1818 with the longer X-axis of the plug it in a side or side or lateral direction, the plug causes the through hole 1818 to elongate in the lateral direction, causing side portions 1820a and 1820b of the support member 1804 to deform away from each other and pull the saddle seating portions 1810 and 1812 inwardly toward each other to configure the support member in the compressed condition of FIG. 62. In this compressed condition, the support member is configured to be inserted between adjacent laminar regions similar to the other embodiments.

Figure 61:
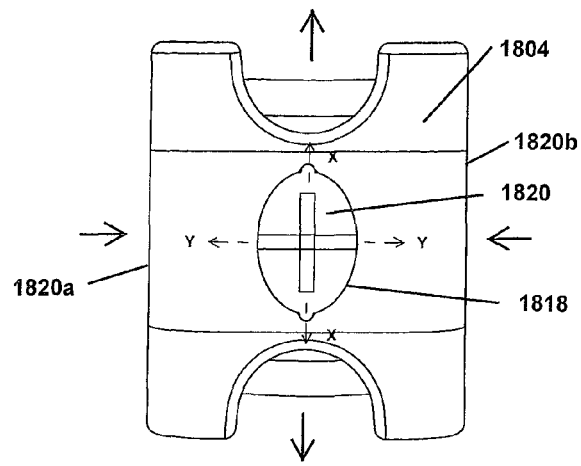
FIG. 61 is an elevational view of the laminar spacer showing it in an expanded configuration.
Figure 62:
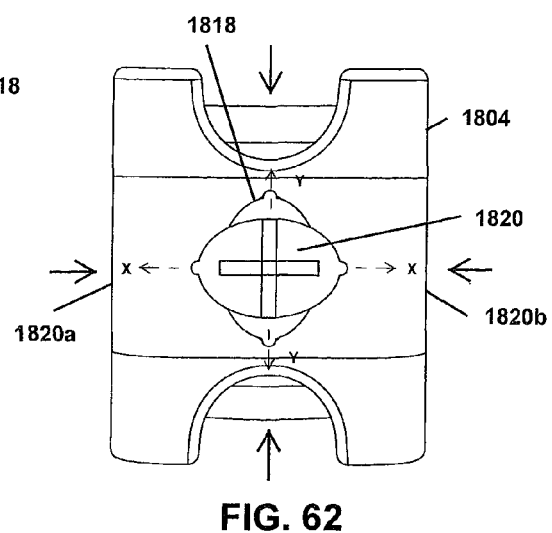
FIG. 62 is an elevational view of the laminar spacer showing it in an contracted configuration.

To transform the support member 1804 into the expanded or distracted state, the plug member 1820 is rotated so that the longer X-axis is aligned in an inferior/superior orientation to permit the side portions 1820a and 1820b to move inwardly toward each other to permit the saddle seating portions 1810 and 1812 to more away from each other to configure the support member 1804 in the expanded or distracted condition of FIG. 61. In one form, the through hole 1818 may also includes alignment notches 1830 on superior and inferior portions of the through hole 1818 that align with corresponding protrusions 1832 formed on the plug member's outer surface 1828. While the notches 1830 and corresponding protrusions 1832 are shown on superior/inferior areas, they can also be formed on other areas of the through hole 1818. These corresponding features (notches 1830 and protrusions 1832) help to hold the plug member 1820 in a position where the laminar support member 1804 is in the expanded or distracted condition; however, other mechanisms may also be used to hold the laminar support member 1804 in this condition.

To help retain the plug member 1820 in the through hole 1818, a groove 1822 may also be formed on an inner surface 1824 of the though hole 1818. The plug member 1820 includes a corresponding ridge 1826 formed on an outer surface 1828 that is positioned to be received in the groove 1822 when the plug member 1820 is inserted into the through hole 1818. The plug member 1820 may also be retained in the through hole 1818 may other mechanisms.

Figure 63:
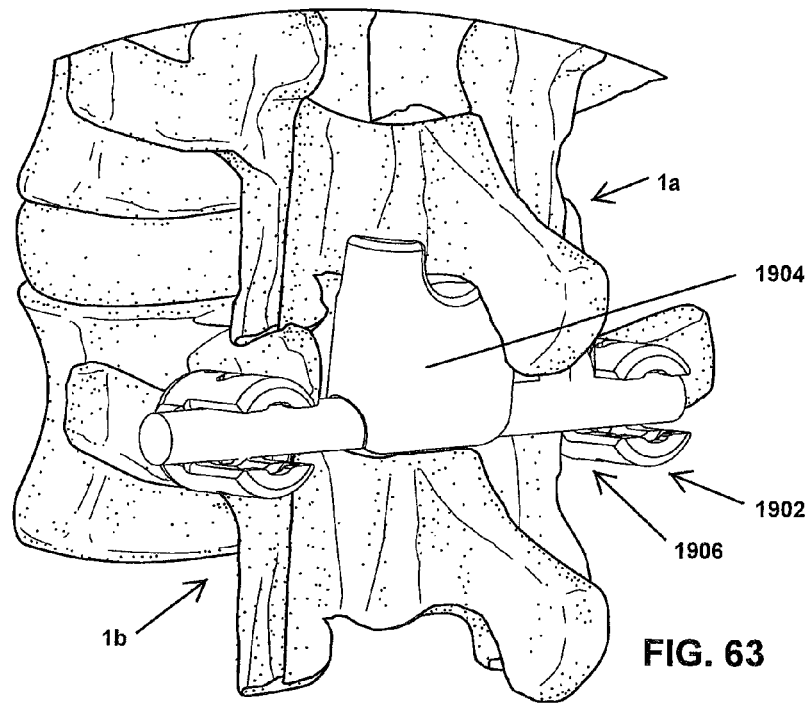
FIG. 63 is a is a perspective view of a spinal stabilization system according to a nineteenth form of the present invention including a laminar spacer and a pedicle screw and rod system.
Figure 64:
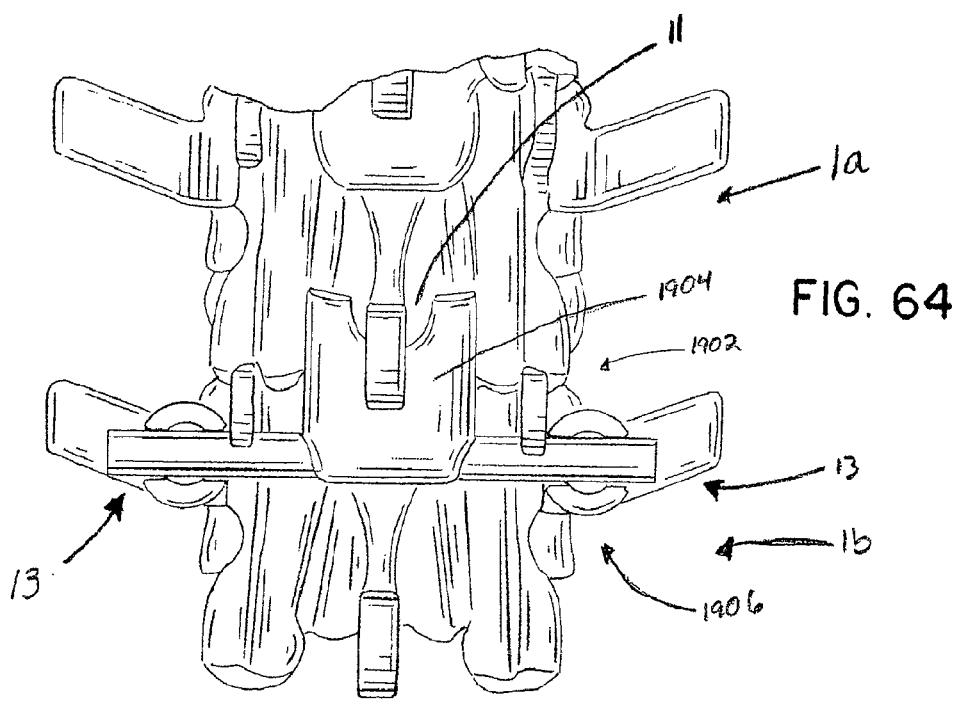
FIG. 64 is an elevational view of the spinal stabilization system of FIG. 63 showing the laminar spacer mated to the laminar region of a superior vertebrae and the pedicle screw and rod system mated to the pedicle regions of an inferior vertebrae.
Figure 65:
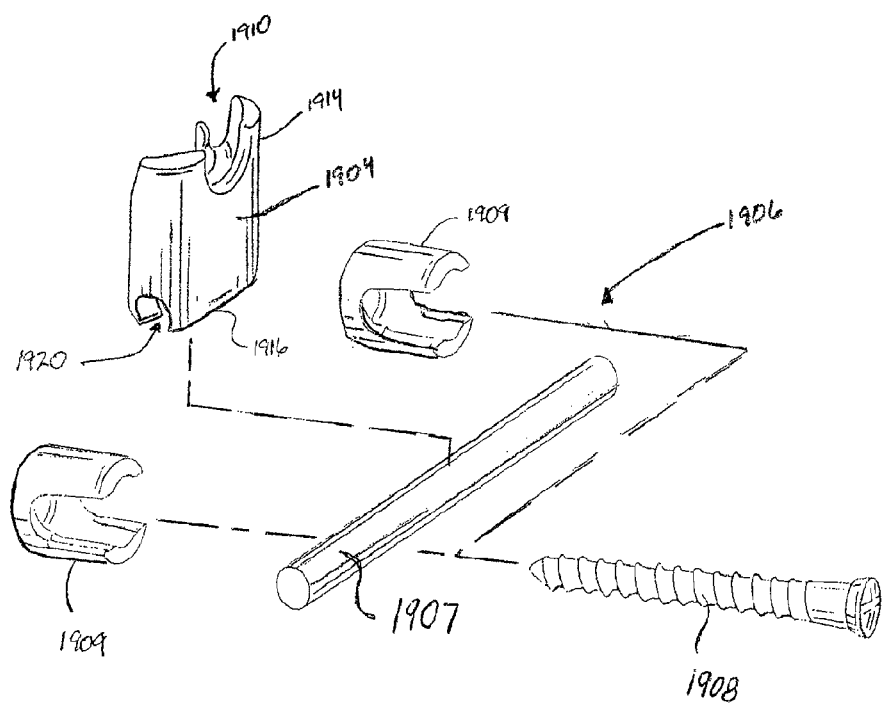
FIG. 65 is an exploded view of the spinal stabilization system of FIG. 63 showing the laminar spacer, a connecting rod, and a pair of pedicle screw devices.
Figure 69:
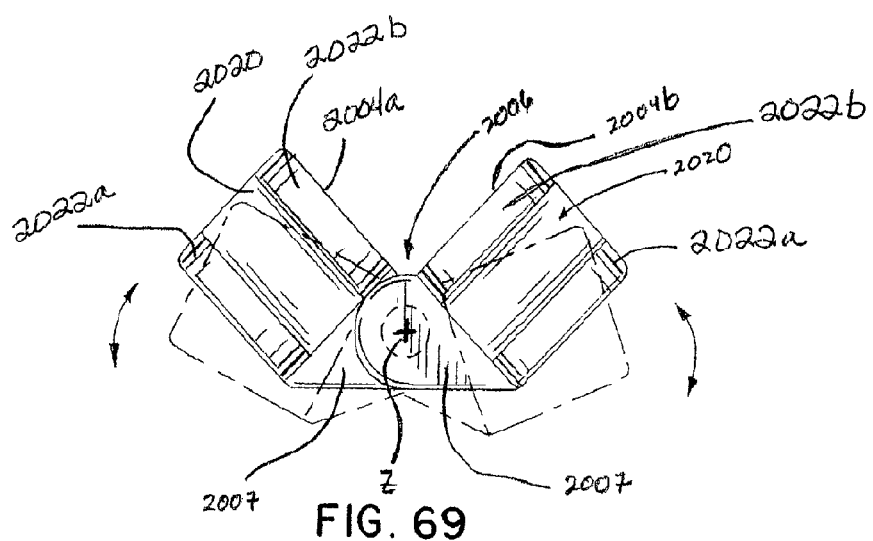
FIG. 69 is a top plan view of the butterfly laminar spacer of FIG. 66 showing first and second laminar spacers pivotally connected to each other.
Figure 70:
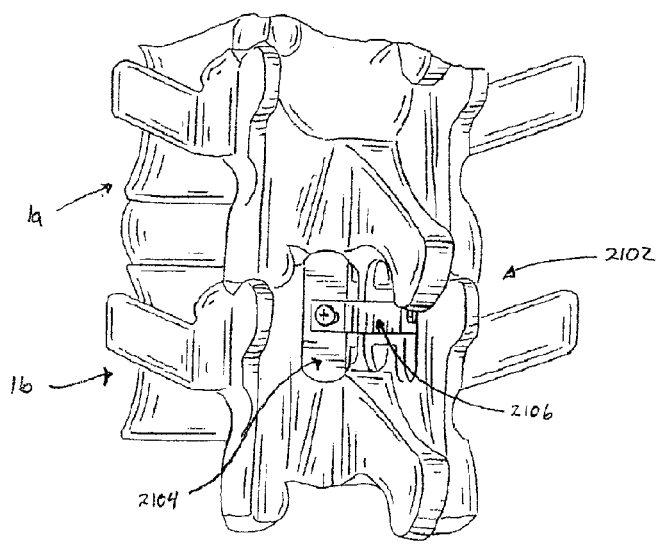
FIG. 70 is a is a perspective view of a spinal stabilization system according to a twenty-first form of the present invention including a pair of laminar spacers connected by a resilient connector.
Figure 71:
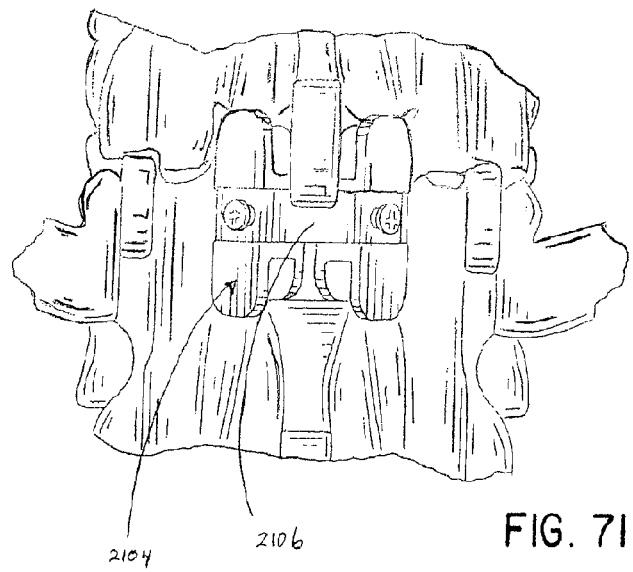
FIG. 71 is an elevational view of the spinal stabilization system of FIG. 70 shown connected to superior and inferior vertebrae.

Referring to FIGS. 63-64, a nineteenth embodiment of a spinal stabilization system 1902 is illustrated in the form of an assembly that includes a support member 1904 and a pedicle screw and rod system 1906. In this form, the support member 1904 interfaces with a laminar region 11 of the superior vertebrae 1a and the pedicle screw and rod system 1906 interfaces with the pedicle regions 13 of the inferior vertebrae 1b.

In one form, the pedicle screw and rod system 1906 includes a rod 1907, a pair of pedicle screws 1908 (one is shown for clarity), and a pair of coupling members 1909 in the form of yoke members. Preferably, the rod 1907 is positioned in a lateral direction extending between the pedicle regions 13 of the inferior vertebrae 1b. Each of the pedicle screws 1908 extends through one of the coupling members 1909 and secures the screw and rod system 1906 to the respective pedicle regions 13. Opposite ends of the rod 1907 are each secured into one of the coupling members 1909, such as by any manner of securing a rod to a pedicle screw yoke (not shown).

The support member 1904 is a generally solid or rigid member, such as formed by PEEK or other relatively rigid biocompatible materials. The member 1904 may also be formed from a resilient material, such as polyurethane or the like. The support member 1904 has an upper saddle portion 1910 on a superior end 1914 thereof (similar to the previously described saddle portion 1510 on the support member 1504) configured to interface with the laminar region 11 of the superior vertebrae 1a when in use. On an opposite or inferior end 1916 of the support member 1904, there is defined a rod conforming notch 1920 that is configured to permit the rod 1907 to be snapped therein so as to be securely held by the support member 1904.

Referring to FIGS. 66 to 69, a twentieth embodiment of a spinal stabilization system 2002 is illustrated in the form of a butterfly assembly 2004 including a pair of interlocking spacer members 2004a and 2004b that are inserted between the laminar regions 11 of adjacent vertebrae. In this form, the each of the interlocking spacer members 2004a and 2004b is configured to pivot relative to the other permitting the assembly to be easily adjusted to fit the laminar regions 11 of varying sized vertebrae. The butterfly assembly 2004 includes a hinge joint 2006 connecting the two spacer members 2004a and 2004b and permits each spacer member to pivot about a Z-axis defined through the hinge joint 2006.

Each spacer member 2004a and 2004b is a generally elongate member (preferably formed from PEEK or other suitable biocompatible material) that includes a projecting arm 2007 extending therefrom forming part of the hinge joint 2006. In one form, the hinge joint 2006 includes cooperating male and female portions, such as a socket portion 2008 in the arm 2007 of the spacer member 2004a and a cooperating ball portion 2010 formed in the arm 2007 of the other spacer member 2004b.

As best shown in the partial cross sectional view of FIG. 68, the arm portion 2007 of spacer 2004a projects outwardly intermediate the spacer member 2004a and includes an aperture 2012 extending through a distal end of the arm portion 2007 to form the female or socket portion 2008 of the hinge joint 2006. The other spacer member 2004b includes a pair of spaced arm portions (such as, for example, a superior arm portion 2007a and an inferior arm portion 2007b) that combine to form the male portion 2010 of the hinge joint 2006.

That is, for example, at a distal end of each arm portion 2007a and 2007b, there is provided ball portions 2014a and 2014b that extending toward each other. Each ball portion 2014a and 2014b is configured to be received, and preferably, snapped in the aperture 2012. That is, ball portion 2014a depends from the arm portion 2007a and is received in a superior side of the aperture 2012, and ball portion 2014b projects upwardly from the arm portion 2007b and is received in an inferior side of the aperture 2012.

Preferably, in use, each spacer member 2004a and 2004b is inserted between the superior vertebrae 1a and inferior vertebrae 1b separately and then the hinge joint 2006 is snapped together in-situ to form the hinge joint 2006. For example, each spacer member 2004a and 2004b is preferably inserted in a manner such that a longitudinal axis thereof, such as axis Z1 of spacer member 2004a and axis Z2 of spacer member 2004b, is generally horizontal (that is, extending laterally relative to the spine and laminar region 11), and then rotated vertically so that an upper portion 2016 thereof engages the laminar region 11 of the superior vertebrae 1a and a lower portion 2018 thereof engages the laminar region 11 of the inferior vertebrae 1b. To this end, the upper portion 2016 includes a saddle surface 2020 formed by upstanding wall portions 2022a and 2022b forming a trough 2024 therebetween sized to receive a portion of the laminar region 11 therein. Preferably, a generally posterior upstanding wall portion 2022a of the saddle seating surface has a longer height than a generally anterior upstanding wall portion 2022b, which permits ease of engagement to the laminar region 11. The lower portion 2018 has a similar saddle surface 2020 except that it extends in an opposite direction so as to engage the laminar region 11 of the inferior vertebrae 1b Turning to FIGS. 70-73, a twenty-first embodiment of the spinal stabilization system is illustrated in the form of an assembly 2102 of at least two spacer members 2104 joined by a connector 2106. Preferably, the connector is a resilient member that permits some movement between the individual spacer members 2104 as the connector 2106 resiliently flexes. By one approach, each of the spacer members 2104 is generally similar to the previous described spacer members 2004; therefore, only the differences therefrom will be described further.

Figure 72:
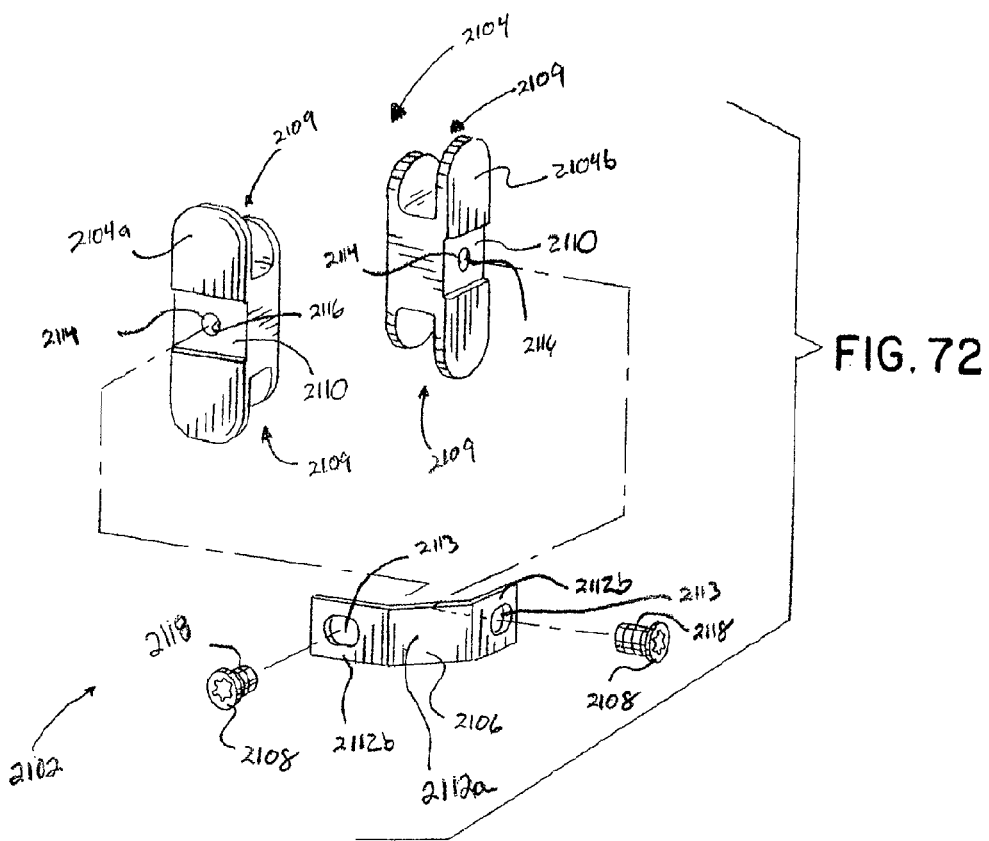
FIG. 72 is an exploded view of the spinal stabilization system of FIG. 71 showing a left and right laminar spacer and a thin, resilient connector extending therebetween.
Figure 73:
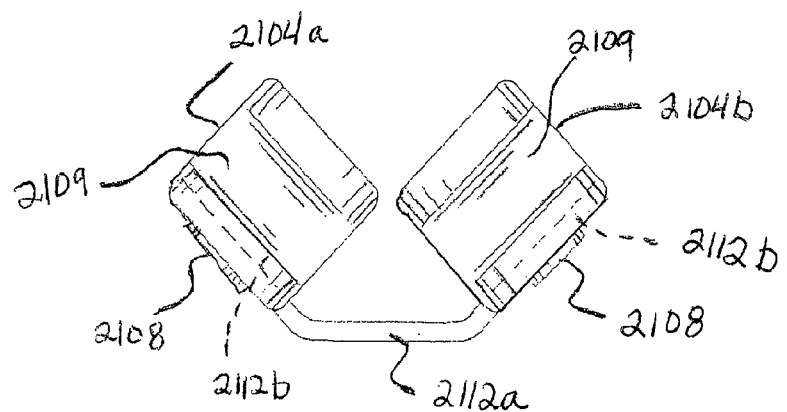
FIG. 73 is a top plan view of the spinal stabilization system of FIG. 71 showing the left and right laminar spacers that extend obliquely relative to each other and the connector.
Figure 74:
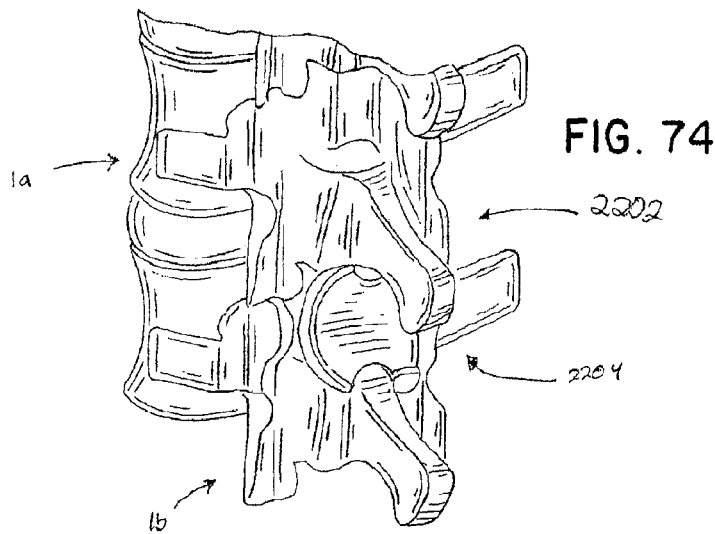
FIG. 74 is a perspective view of a spinal stabilization system according to a twenty-second form of the present invention including a one piece laminar spacer.

As best illustrated in FIGS. 72-73, the assembly 2102 includes the two spacer members 2104a and 2104b joined by the connector 2106 in the form of a thin, resilient connecting strip (such as a titanium or other biocompatible material) that is secured to and extends between the two spacer members 2014a and 2104b. A pair of fasteners 2108 are provided to secure the connector 2106 to each spacer member 2104a and 2104b so that the spacer members 2104a and 2104b are spread apart and generally extend obliquely (such as inclined in a lateral direction) relative to each other as shown in FIG. 73. The fastener 2108 is preferably a threaded set screw; however, other types of fasteners such as pins, bolts, clips, adhesive and the like may also be used. In this oblique configuration, the spacer members 2104a and 2104b are generally arranged and configured to engage the laminar regions 11 of the superior and inferior vertebrae 1a and 1b, respectively, via saddle surfaces 2109 located on opposite ends of each spacer member. The saddle surfaces 2109 are similar to those found on the previously described spacer member 2004.

To position the spacer members 2104a and 2104b in the preferred configuration to engage the respective laminar regions 11, the connecting member 2106 preferably includes multiple portions. For instance, the connecting member 2106 preferably includes at least an intermediate portion 2112a extending between two end portions 2112b. Each end portion 2112*b* extends obliquely (i.e., inclined laterally) relative to the intermediate portion 2112*a* such that the two end portions 2112*b* generally taper towards each other (for example, greater than about 90 degrees).

The end portions 2112*b* are configured to be secured to the spacer members 2104*a* and 2104*b* via the fastener 2108. By one approach, to secure the connecting member 2106 to the spacer members 2104*a* and 2104*b*, each spacer member 2104 includes a laterally extending notch or slot 2110 extending therethrough sized to receive the end portions 2112*b* of the connecting member 2106. To this end, the end portions 2112*b* of the connecting member 2106 include a generally elongate aperture 2113 sized to receive the fastener 2108 therethrough and each spacer member slot 2110 includes a bore 2114 having an internal thread 2116 that mates with an external thread 2118 on the fastener 2108.

In use, the connector 2106 is first secured to one of the spacer members, such as member 2104*a*. Then, the spacer member 2104*a* and fastened connector 2106 assembly is inserted between the laminar regions 11 of adjacent vertebrae 1*a* and 1*b*. Separately, the other spacer member 2104*b* is then inserted between the laminar regions 11, which is then secured to the free end portion 2112*b* of the connector 2016 as described previously. Because of the elongate aperture 2113 in the end portions, the surgeon has the ability to adjust the positioning of the space members 2104 prior to tightening the fasteners 2108 to secure the assembly together.

Figure 75:
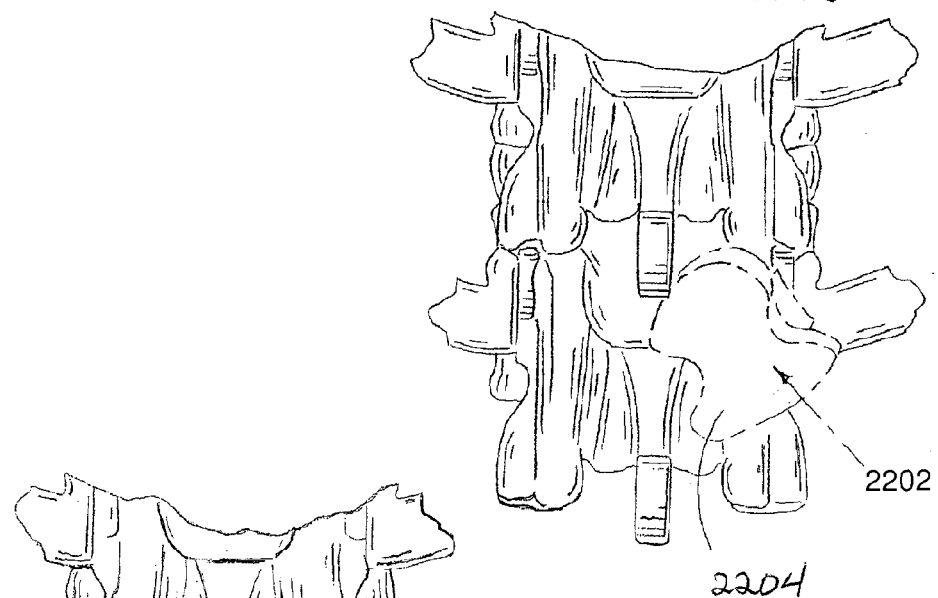
FIG. 75 is an elevational view of the spinal stabilization system showing the laminar spacer in phantom in an initial insertion position.
Figure 76:
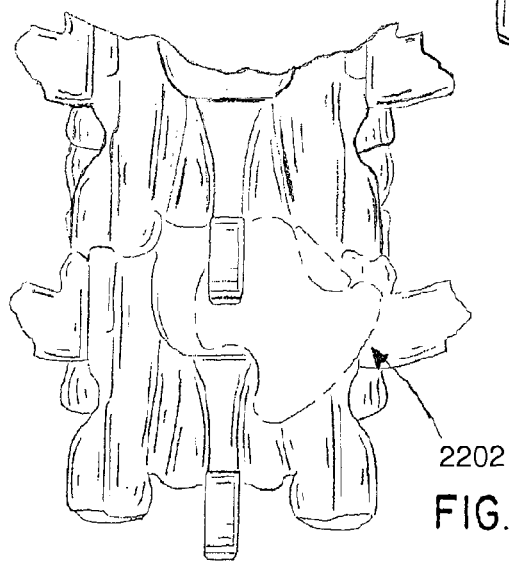
FIG. 76 is an elevational view of the spinal stabilization system showing the laminar spacer in phantom in an intermediate insertion position.
Figure 77:
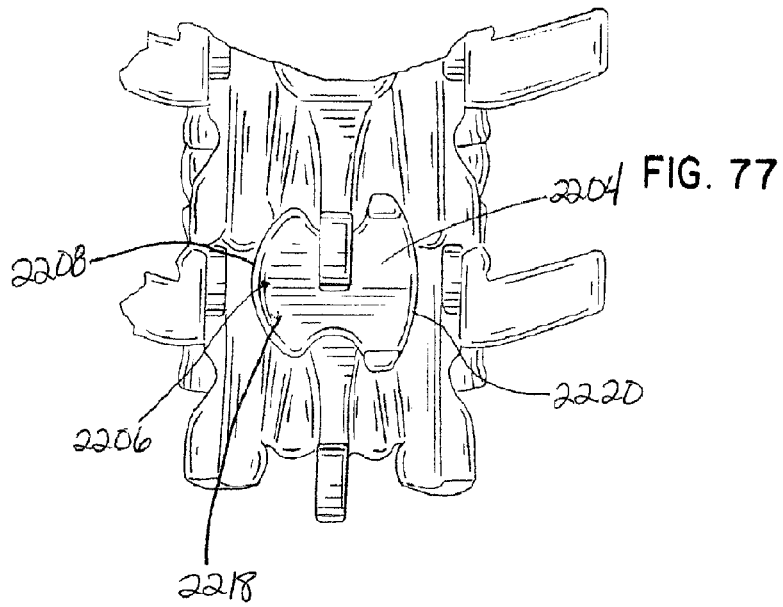
FIG. 77 an elevational view of the spinal stabilization system showing the laminar spacer a final insertion position.

Referring to FIGS. 74-81, a twenty-second embodiment of a spinal stabilization system 2202 is illustrated in the form of a unitary laminar spacer 2204 having a configuration that permits it to be inserted from a lateral approach and then pivoted into position where it is wedged between the laminar regions 11 of adjacent vertebrae as shown in FIGS. 75-77. The laminar spacer 2204 may be formed from any resilient-type material, such as polyurethane and the like, or from a more rigid material, such as PEEK or the like. While the spacer 2204 is illustrated as a generally solid member, if formed from a more resilient material, it can optionally include an actuator or adjustment device to shift the spacer 2204 from a compressed to an expanded or distracted configuration similar to that found on the embodiments shown in FIG. 47 (spacer member 1504) or FIG. 58 (spacer member 1804).

Figure 78:
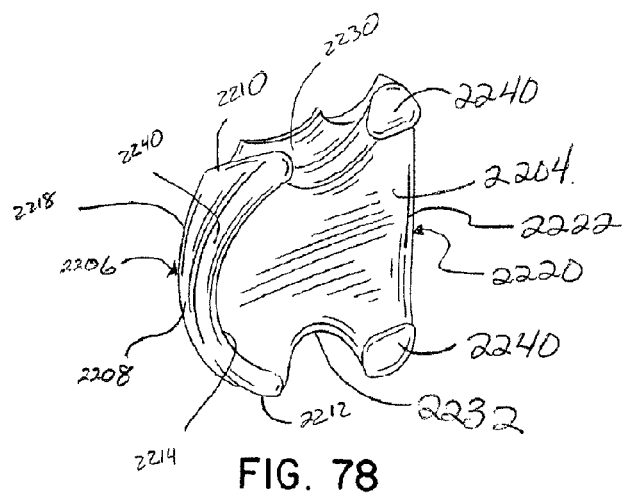
FIG. 78 is a perspective view of the laminar spacer showing an insertion end having a rounded contour.
Figure 79:
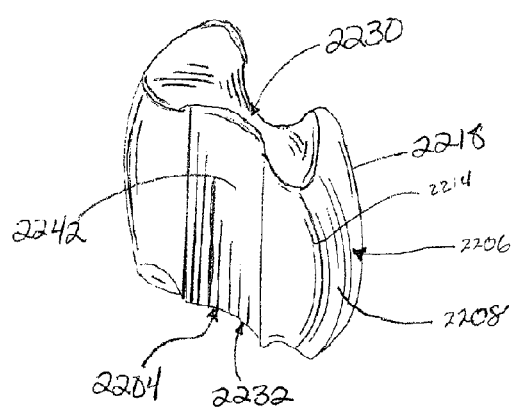
FIG. 79 is a perspective view of the laminar spacer showing a rounded slot configured to mate with corresponding structure on a vertebrae.

As best shown in FIGS. 77-79, the laminar spacer 2204 has a configuration that provides for the preferred lateral insertion approach. For example, the spacer 2204 has an insertion side 2206 having a curved or rounded edge 2208 that provides for easy insertion between the laminar regions 11. That is, the edge 2208 is generally curved from a superior or top side 2210 to an inferior or lower side 2212. In addition, the edge 2208 is also beveled or rounded from an anterior 2214 to a posterior 2218 side of the spacer as well. Such curvatures generally provide for an enhanced ability to insert and pivot the spacer into the desired position.

Opposite the insertion side 2206, the laminar spacer 2204 has a holding or grasping side 2220 that has a configuration that permits a surgeon to more easily grasp or hold the spacer 2204 either with their hands or with an insertion instrument (not shown). To this end, the holding side 2220 has a generally flat or straight edge 2222 providing surfaces for easy grasping by a tool or the surgeons hands. However, as shown in FIG. 77, the holding edge 2220 may also have an arcuate curvature as well.

Figure 80:
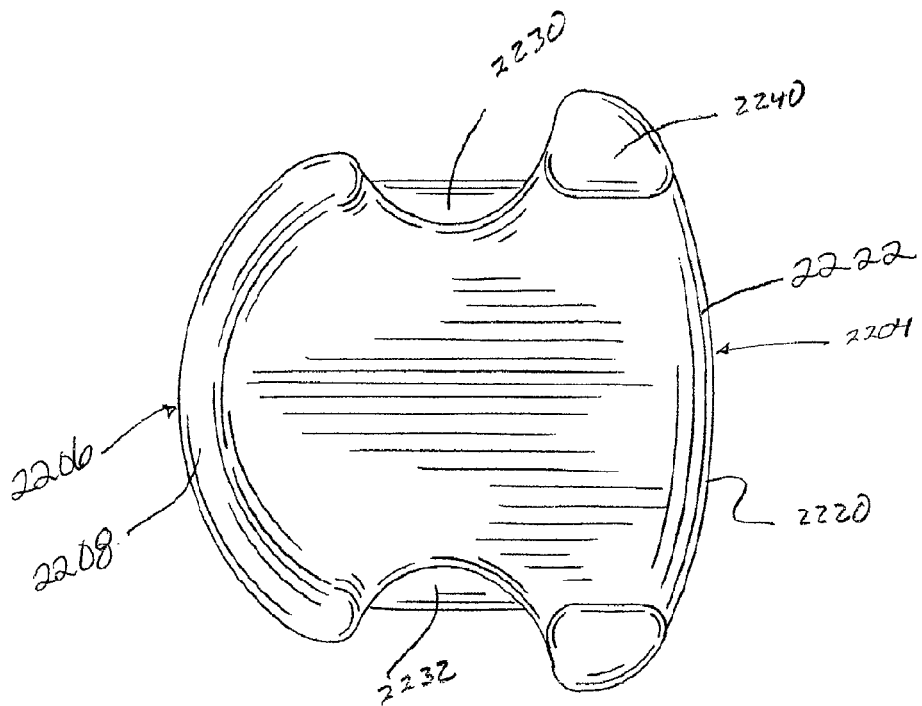
FIG. 80 is a elevational view of the laminar spacer showing an rounded insertion end and a generally flat grasping end.
Figure 81:
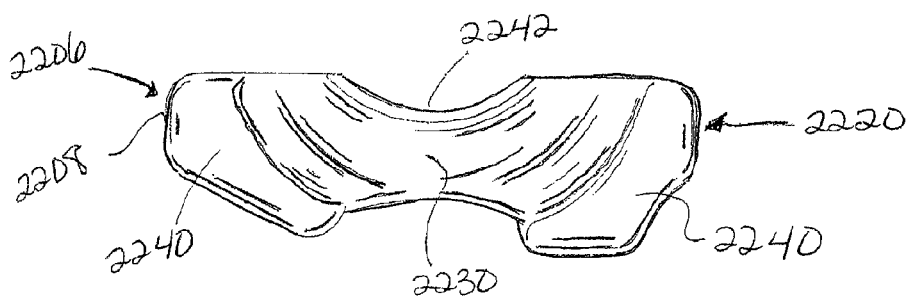
FIG. 81 is a top plan view of the laminar spacer showing a saddle seating portion configured.

To provide a secure mounting between the adjacent vertebrae 1*a* and 1*b* the laminar spacer 2204 also includes a superior saddle surface 2230 and an inferior saddle surface 2232 that have contours that generally match the corresponding contours on the vertebrae. In addition, the spacer 2204 may also include structure that helps retain the spacer in the desired position and orientation between the vertebrae. For example, the spacer may include stability ridges 2240 or a stability channel 2242 that are configured to interface with various portions of the vertebrae. In addition, as best shown in FIGS. 77 and 80, the laminar spacer 2204 also preferably has a generally hour-glass shape that further aids in insertion and pivoting into the final position and also helps retain the spacer between the adjacent laminar regions 11.

Figure 82:
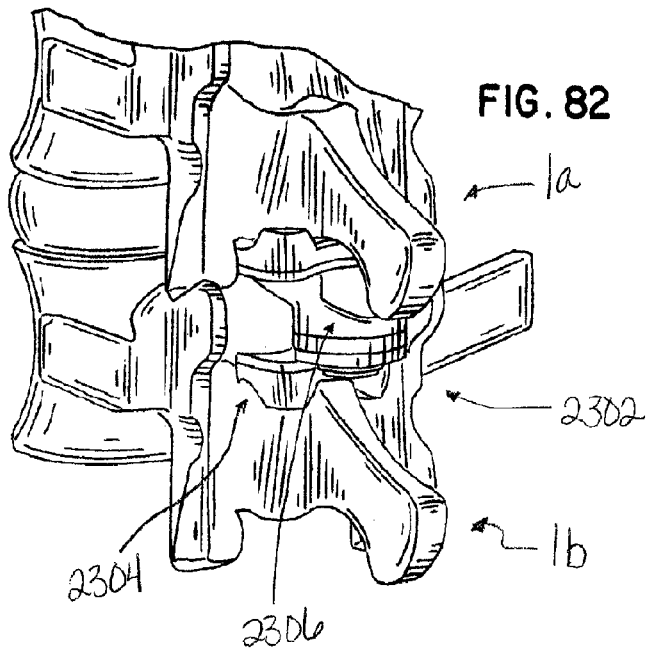
FIG. 82 is a perspective view of a spinal stabilization system according to a twenty-third form of the present invention including an articulating laminar spacer.
Figure 83:
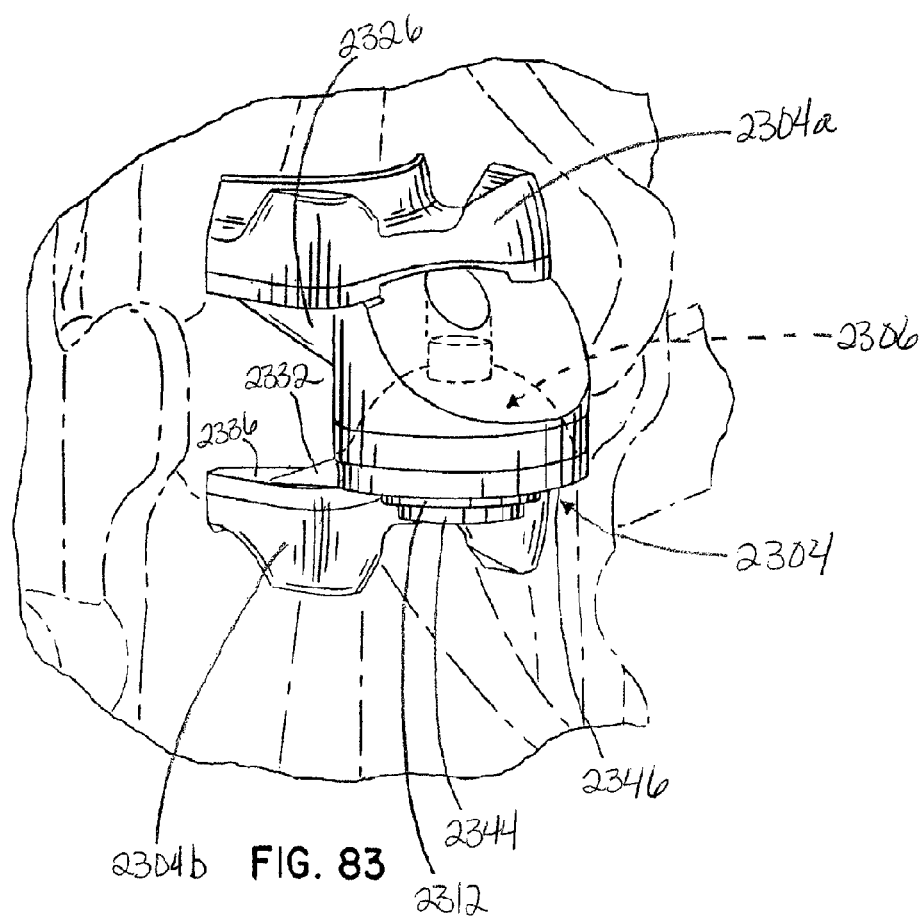
FIG. 83 is a perspective view of the laminar spacer of FIG. 82 showing an inferior laminar spacer, a superior laminar spacer, and an articulating joint therebetween.
Figure 84:
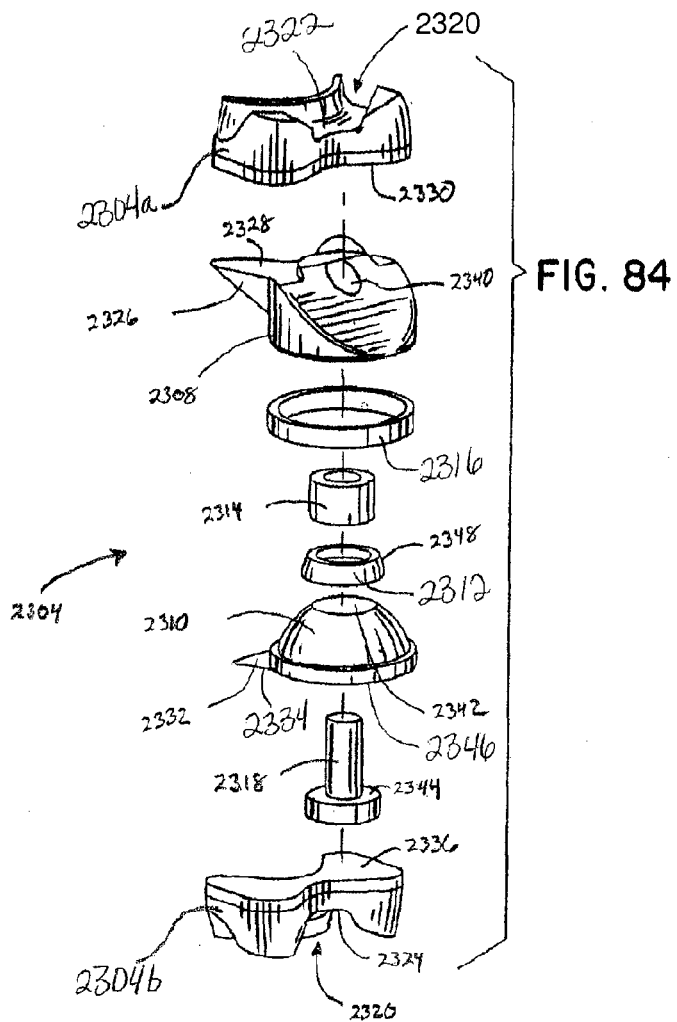
FIG. 84 is an exploded view of the laminar spacer of FIG. 82 showing the inferior laminar spacer, the superior laminar space, and the articulating joint having a fastener, an outer washer, an inner washer, and a doomed washer.
Figure 85:
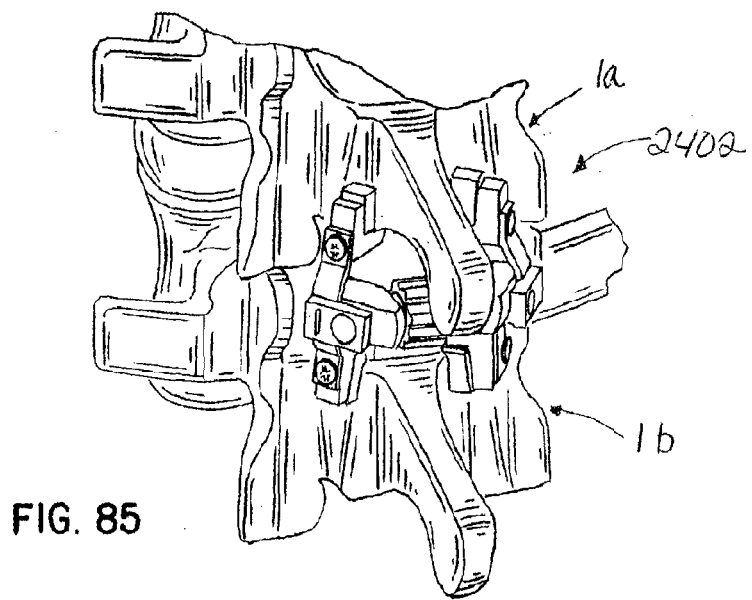
FIG. 85 is a perspective view of a spinal stabilization system according to a twenty-fourth form of the present invention including the spacer members from FIG. 18 in combination with an adjustment device.
Figure 86:
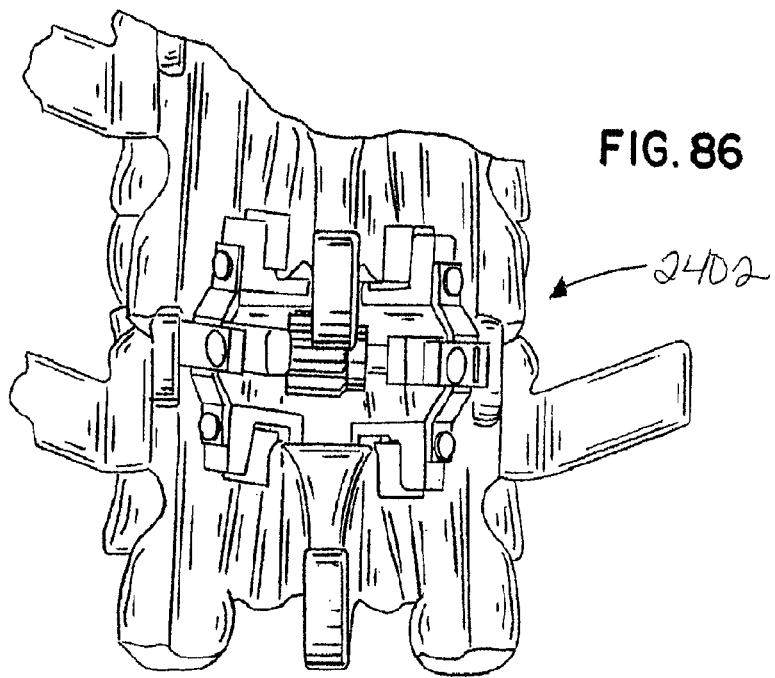
FIG. 86 is an elevational view of the spinal stabilization system of FIG. 85 shown between adjacent laminar regions of a superior and inferior vertebrae.

Referring to FIGS. 82 to 84, a twenty-third embodiment of a laminar stabilization assembly 2302 is illustrated in the form of a laminar spacer 2304 having an articulating connection 2306 between a superior laminar spacer 2304*a* and an inferior laminar spacer 2304*b*. In one form, the articulating connection 2306 includes a cooperating ball and socket joint. As best shown in FIG. 84, the assembly 2302 includes multiple components. For instance, it preferably includes the superior laminar spacer or a superior laminar bra 2304*a*, a socket portion 2308 joined to the superior laminar spacer 2304*a*, the inferior laminar spacer or an inferior laminar bra 2304*b*, a dome or ball portion 2310 joined to the inferior laminar spacer 2304*b*, a spherical washer 2312, an inside washer 2314, an outside washer 2316, and an fastener 2318 to secure the assembly together.

Similar to the previously described embodiments, the superior laminar spacer 2304*a* and the inferior laminar spacer 2304*b* have semicircular slots or saddle surface portions 2320 on their respective superior surface 2322 and inferior surface 2324 that generally conform and receive the superior and inferior surfaces of the laminar regions 11 of adjacent vertebrae (superior vertebrae 1*a* and inferior vertebrae 1*b*). Preferably, the laminar spacers 2304*a* and 2304*b* can be made of any bio-compatible material (PEEK, polyurethane, and the like), or conversely the whole piece could be solid.

The superior laminar spacer 2304*a* is secured to the socket portion 2308. By one approach, the socket portion 2308 includes projecting ledges 2326 that provide a stable mounting surface 2328, which is preferably a generally flat surface configured to abut an inferior or bottom flat surface 2330 of the superior laminar spacer 2304*a*. The socket portion 2304*a* can be secured to the superior laminar spacer 2304*a* by any suitable mechanism, such as fasteners, glue, adhesive, clips, and the like. Likewise, the inferior laminar spacer 2304*b* is secured to the ball portion 2310 in a similar manner. That is, the ball portion 2310 includes projecting feet 2332 that provide a stable mounting surface 2334, which is also preferably a generally flat surface that is configured to abut a superior or upper surface 2336 of the inferior laminar spacer 2304*b*.

The socket portion 2308 includes a bore 2340 that is tapped therethrough to receive the fastener 2318 extending up from the bottom portion. By one approach, the bore 2340 includes an internal thread that is configured to threadably mate with an external thread on the fastener. In this manner, the articulating joint 2306 is secured to the superior laminar spacer 2304*a* and also spaced from the load bearing superior laminar spacer 2304*a* and inferior laminar spacer 2304*b*. The fastener 2318 substantially secures the various components of the assembly 2302 together.

The ball portion 2310 also has a bore 2342 extending therethrough to receive the fastener 2318. Preferably, the bore 2342 in the inferior portion 2304*b* is larger than the diameter of the fastener 2318. An extending flange 2344 of the fastener 2318 rests against the spherical washer 2312 (preferably formed from a polymer material) positioned on the underside 2346 of the ball portion 2310 (FIG. 83). Preferably, a doomed portion 2348 of the washer 2312 faces the superior direction in the bore 2342 to allow some articulation of the joint 2306. Inside the bore 2342 there is also provided the inside washer 2314, which is also preferably formed from a polymer and/or elastic material, having an inside diameter thereof slightly larger than an outside diameter of the fastener 2318 and an outside diameter thereof slightly smaller than an inner diameter of the bore 2342. In this manner, the inside washer 2314 allows for some movement or play in the joint 2306 as well.

Surrounding the outer portion of the ball portion 2310 is the outside washer 2316, which is also preferably made from a polymer and/or elastic material. The outside washer restricts the amount of articulation in the joint 2306 and can provide more or less articulation based on an axial height of the washer. For example, a height 2350 of the outside washer 2316 is selected to either permit greater articulation or less articulation. For example, a larger height of the washer 2316 permits less articulation in the implant joint 2306 because the socket 2308 will impact the washer 2316 when it articulates. On the other hand, a smaller height of the washer 2316 allows for more articulation because the socket portion 2308 has more space or room in which to articulate.

In use, the assembly 2302 would be inserted into the laminar space between adjacent vertebrae 1a and 1b by first distracting the space with an appropriate tool (not shown) and then compressing the assembly by the amount allowed by the outside washer 2316

Referring to FIGS. 85-88, a twenty-fourth embodiment of a laminar stabilization assembly 2402 is illustrated, which is similar to the laminar stabilization system 700 as shown in FIG. 18; as a result, only the differences therefrom will be described further in this embodiment. The assembly 2402 includes the first engagement member 702 and the second engagement member 704 connected by the support structure in the form of a pair of biasing members 706. The assembly 2402 further includes a cross member device 2406 that provides added stability and also allows for lateral adjustment of the assembly 2302 to better conform a patient's anatomy.

Figure 87:
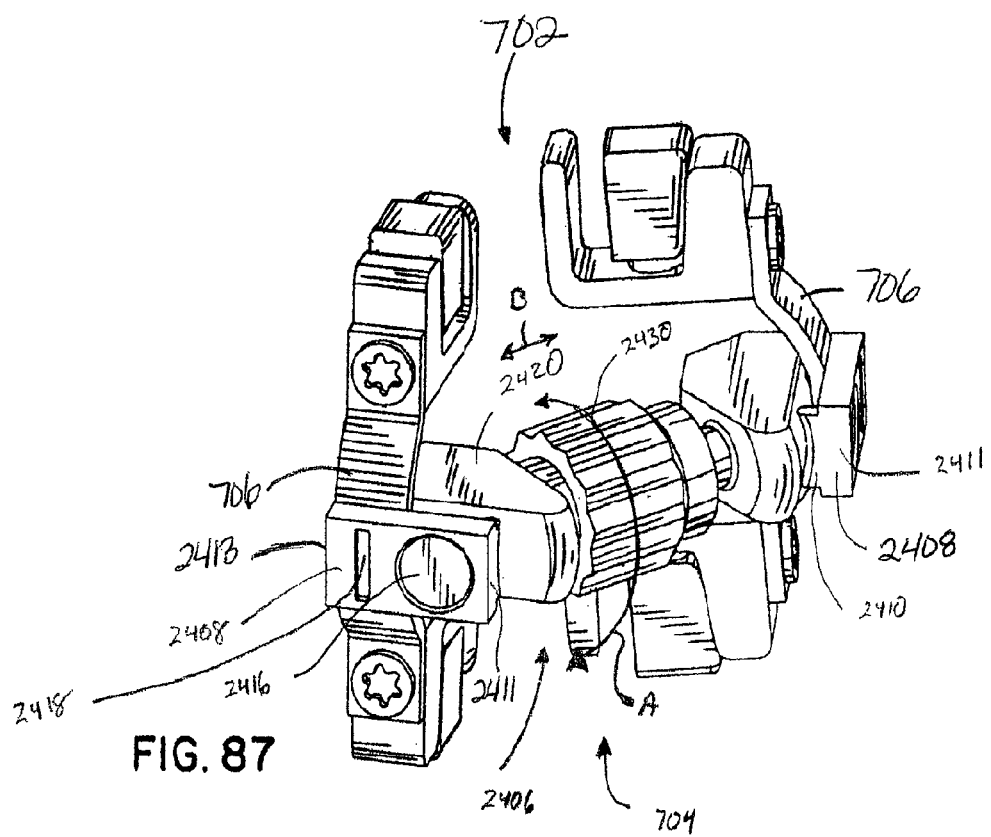
FIG. 87 is a perspective view of the laminar spacer of FIG. 85 showing a lock nut that rotatably adjusts the spacing between left and right portions thereof.
Figure 88:
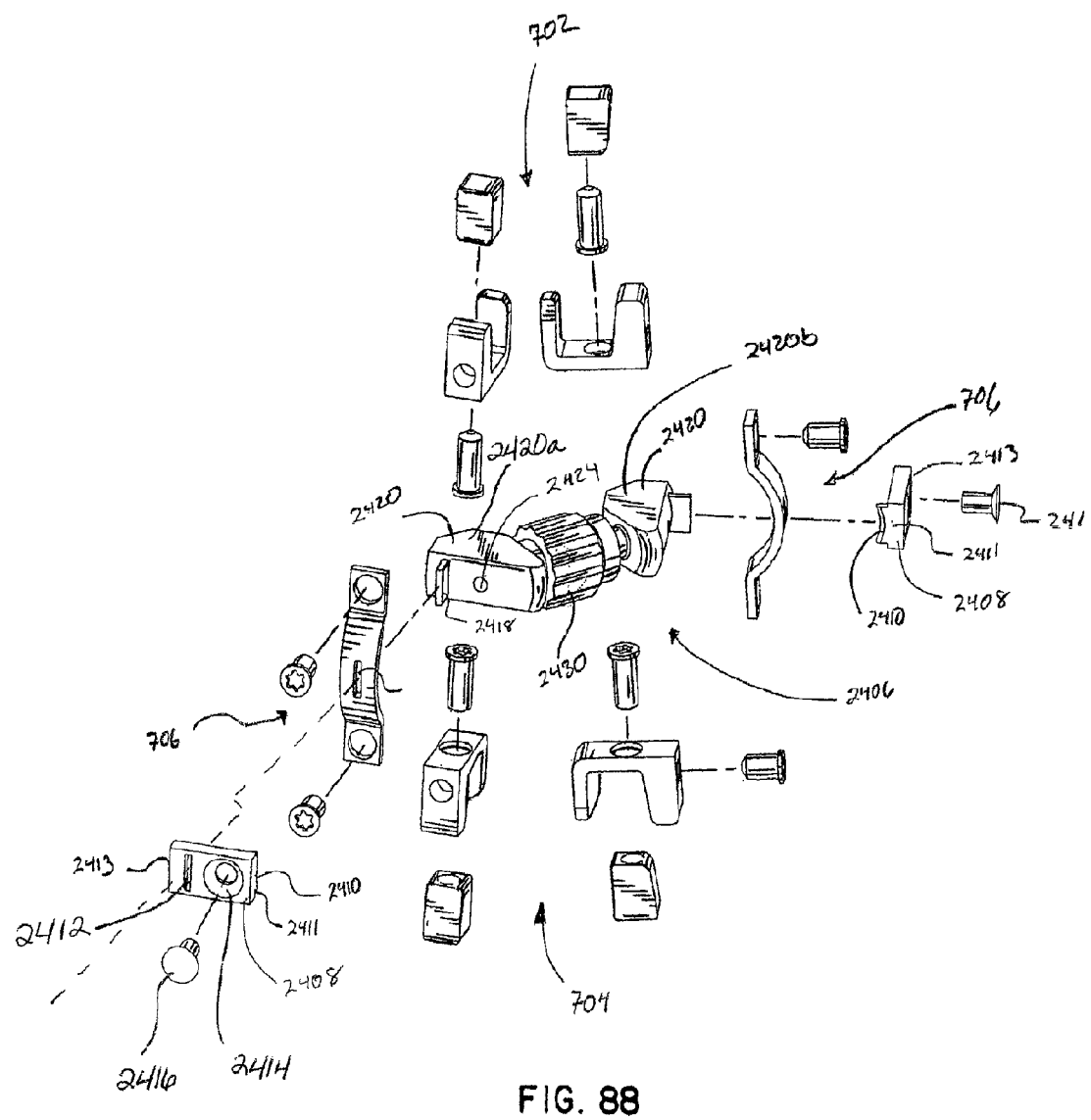
FIG. 88 is an exploded view of the laminar spacer of FIG. 85 showing the adjustment device thereof and a lock plate to secure the adjustment device to the spacer members.

The cross member device 2406 is attached to each of the biasing members 706 by a pair of attachment members 2408. For instance, as best shown in FIG. 88, the attachment members 2408 are generally rectangular in shape with a semicircular protrusion 2410 at one end 2411 thereof and a slot 2412 at the other end 2413 thereof. It also includes a countersunk bore 2414 to receive a fastener 2416 that secures the cross member device to the attachment members 2408. The semicircular protrusion 2410 on the members 2408 is to compensate for the thickness of the biasing members 706 so that each attachment member 2408 is attached so that the one end 2411 of the member abuts the cross member 2406 and provides stability thereto as best shown in FIG. 87. The slot 2410 is arranged and configured to receive a similar sized and shaped protrusion 2418 disposed on a spring grabbing member 2420 on one end of the cross member 2406. The protrusion 2418 extends through a slot 2422 in the biasing member 706 and is press-fit in a tight arrangement in the slot 2412 in the attachment member 2408. The countersunk bore 2414 is for the fastener 2416 that is arranged and configured to be threadably received in a bore 2424 the spring grabbing member 2422.

The assembly 2402 includes a pair of spring grabbing members 2420 that are on opposite sides of the cross member 2406 and each are connected to one of the biasing members 706 as generally described above. Preferably, the cross member 2406 includes a left spring grabber member 2420a that has the protrusion 2418 to mate with the jaw 2408, the hole 2424 for the fastener 2416 and a protruding hollow stem 2426. The stem on the left spring grabber 2420a is a female end that receives a corresponding protrusion 2428 or male end of a right spring grabber 2420b.

Figure 88A:
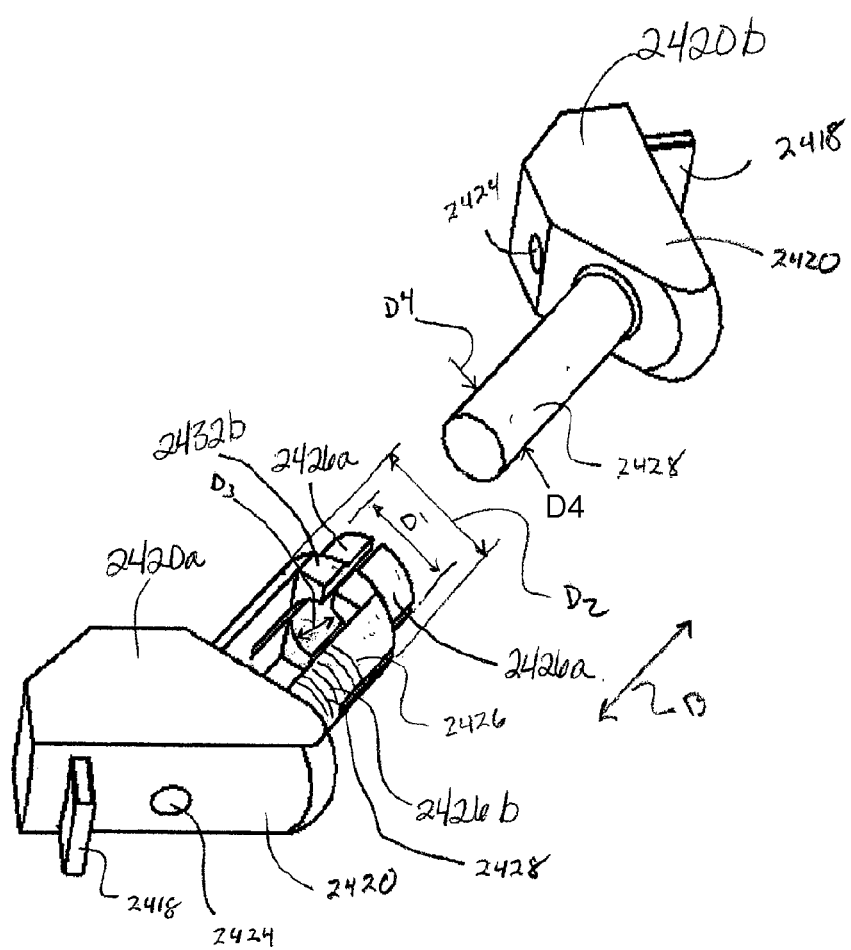
FIG. 88A is a perspective view of a first and second spacer members of the adjustment device showing a hollow stem configured to receive a protrusion.
Figure 89:
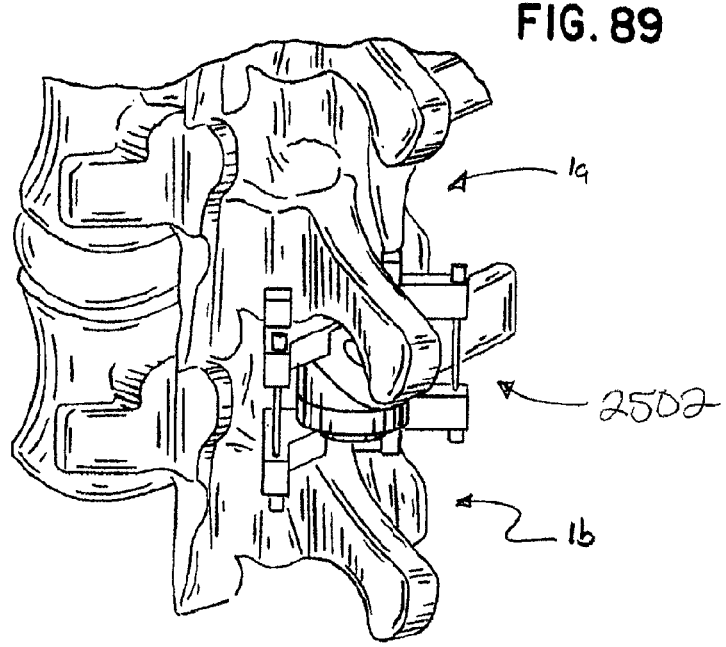
FIG. 89 is a perspective view of a spinal stabilization system according to a twenty-fifth form of the present invention including an articulating joint from the embodiment shown in FIGS. 82-84 combined with the laminar spacer member from the embodiment of FIG. 26.
Figure 90:
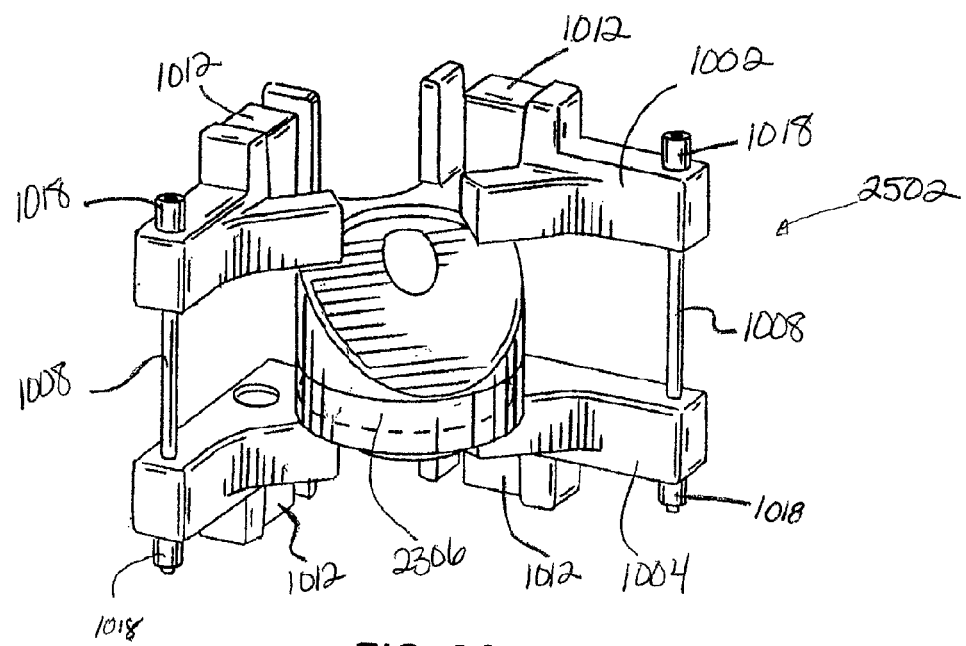
FIG. 90 is a perspective view of the spinal stabilization system of FIG. 89 showing one portion of the joint being formed integral with a superior portion of a laminar spacer member and a second portion of the joint being formed integral with an inferior portion of a laminar spacer member.
Figure 91:
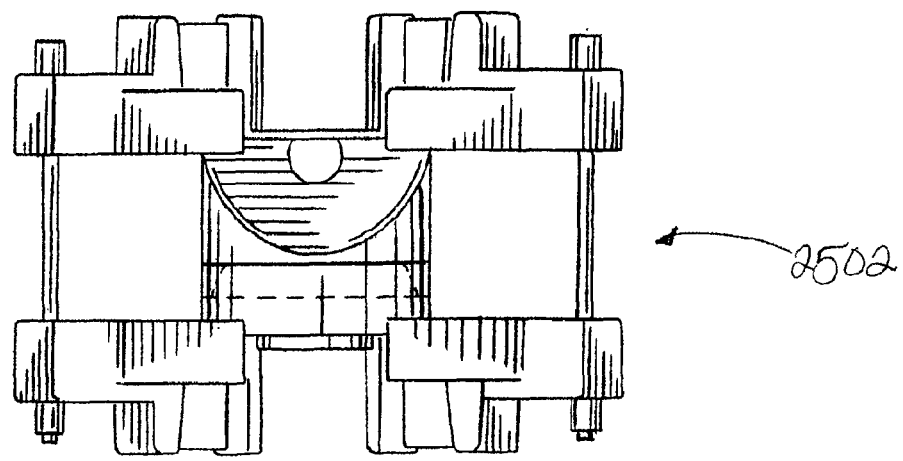
FIG. 91 is an elevational view of the spinal stabilization system of FIG. 89.
Figure 92:
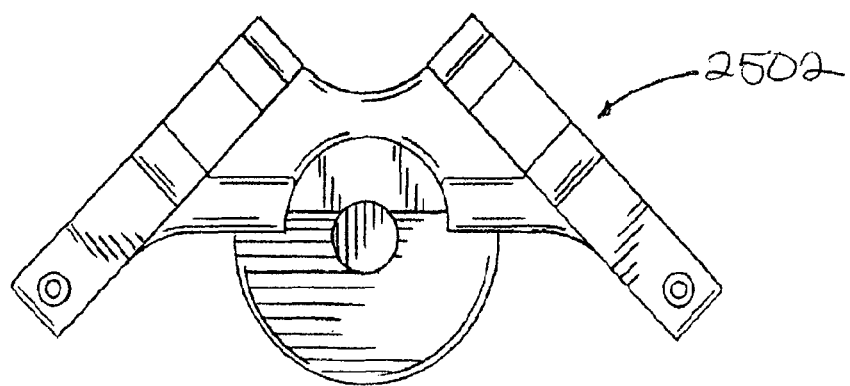
FIG. 92 is a top plan view of the spinal stabilization system of FIG. 89.
Figure 93:
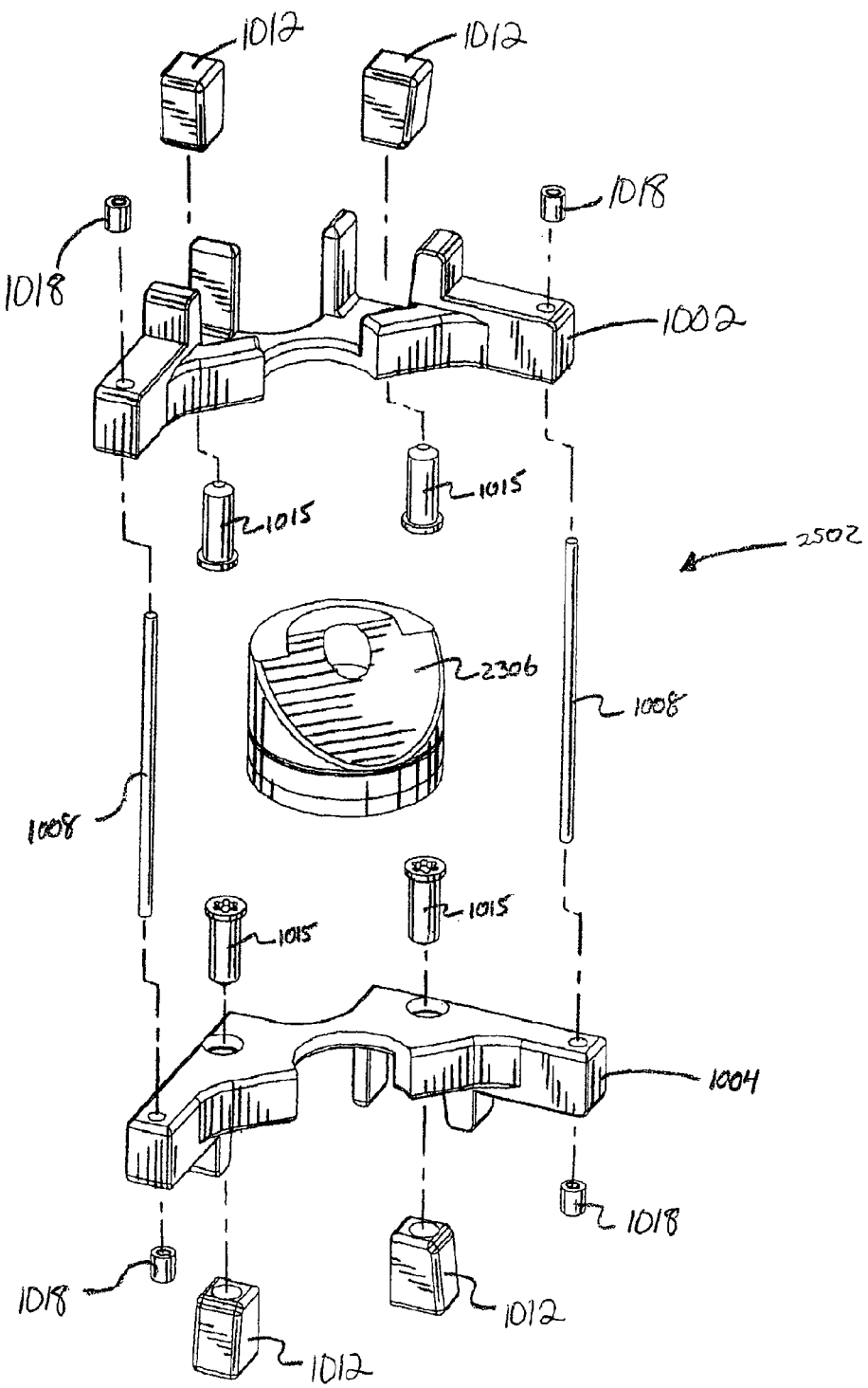
FIG. 93 is an exploded view of the spinal stabilization system of FIG. 93.

Referring to FIG. 88a, the hollow stem 2426 has at least two outer diameter portions 2426a and 2426b that have diameters D1 and D2, respectively. The diameter D2 is preferably larger and includes an external threading 2428 that threadably mates with an internal threading of a collet nut 2430. The outside diameter D2 is slightly larger than an inside diameter of the collet nut 2430. The stem 2426 also preferably includes facing stem portion 2432a and 2432b so that the stem forms a slotted hollow protrusion. As a result, as the collet nut 2430 is rotated (i.e., rotation arrow A in FIG. 87), it is threaded onto the larger diameter portion 2426b (D2) of the stem 2426, and the smaller diameter portion 2426a (D1) is pinched around the protrusion 2428 of the right spring grabber member 2420b to tightly secure the grabber members 2420a and b in such position. An inner diameter D3 of the hollow stem 2426 of the left grabber member 2426a is slightly larger than an outer diameter D4 on the protrusion 2428 of the right grabber member 2426b.

This cross member system 2406 allows the surgeon to adjust the spacing between the opposing sides of the assembly 2402 to a particular patient's anatomy, and then tighten the collet nut 2430 to maintain the adjustment. To this end, the protrusion 2428 may be slideably inserted or withdrawn (i.e., motion arrow B in FIG. 87) from the hollow stem 2426 depending on the particular anatomy of the patient to increase or decrease the spacing between the left and right sides of the assembly. Once correctly spaced, the surgeon rotates the collet nut 2430 to draw the stem portions 2432a and 2432b toward each to pinch the protrusion 2428 and lock the assembly 2402 in the adjusted configuration Referring to FIGS. 89-93, a twenty-fifth embodiment of a laminar stabilization system 2502 is illustrated that combines the articulating joint 2306 from the embodiments in FIGS. 82-84 with an unloading device 2504 that generally includes the first engagement member 1002 and the second engagement member 1004 from the embodiment of FIG. 26.

Preferably, the articulating joint 2306 is formed in one piece with the engagement members 1002 and 1004. As a result, depending on the tightness of the fasteners 1018 securing the rods 1008 between the engagement members 1002 and 1004, the joint 2306 can articulate more or less.

Figure 94:
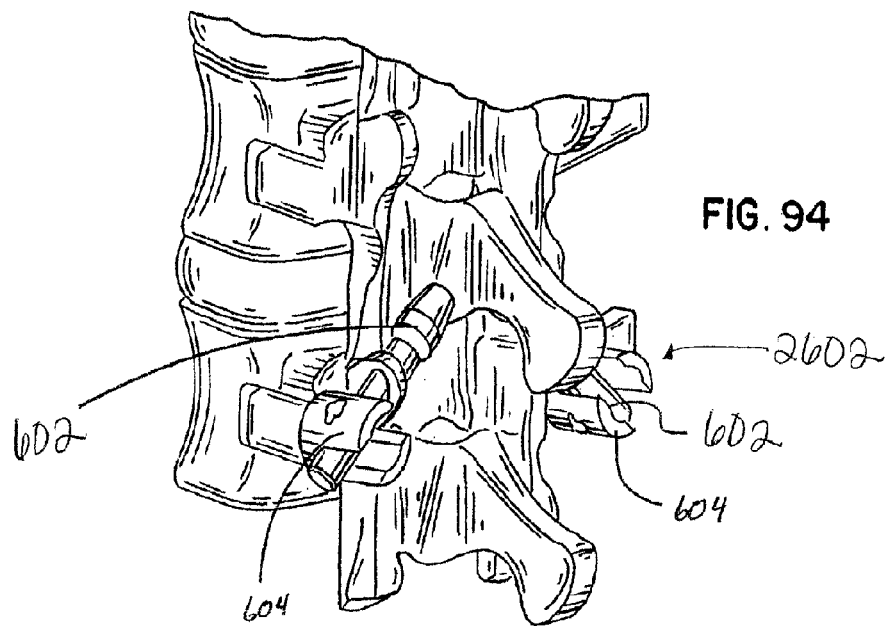
FIG. 94 a perspective view of a spinal stabilization system according to a twenty-six form of the present invention including a pair of laminar rods and pedicle screw fasteners similar to the embodiment of FIG. 16 except that the rods are generally straight.
Figure 95:
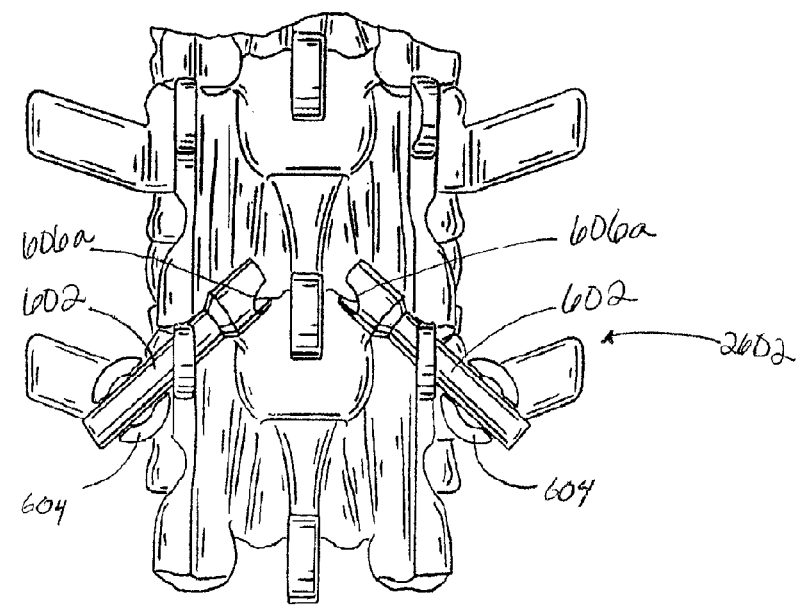
FIG. 95 is an elevational view of the spinal stabilization system of FIG. 94 showing the rods connected between the pedicle region of an inferior vertebrae and the laminar regions of a superior vertebrae.

Referring to FIGS. 94-95, a twenty-sixth embodiment of a laminar stabilization system 2602 is illustrated that is similar to spinal stabilization system 600 as depicted in FIGS. 14-16. That is, the system 2602 includes the pair of rods 602 and support structure including the pair of fixation devices 604. In this embodiment, the rods 602 are generally straight and not hooked as with the system 600. The fixation devices 604 fix each of the rods 602 to pedicle regions of an inferior vertebra 1b. Each of the rods 602 is generally straight and has portions 606a that are configured to closely engage the inferior edges of the laminar region 11 of the superior vertebrae 1a. Therefore, the rods 602 minimize any reduction in the intervertebral spaced between the superior and inferior vertebrae by counteracting compressive loads applied to the spine. Specifically, a compressive load applied to either the superior or inferior vertebra 1a or 1b is transferred directly to at least one of the rods 602 and of one of the fixation devices 604.

It should be appreciated that the foregoing forms of the spinal stabilization system described herein are merely examples of the present invention. The superior/inferior orientation of each of the forms may be varied or altered and such variations or alterations are intended to be within the scope of the present invention. Additionally, while various forms of the present invention have been described herein as primarily serving to minimize reduction of the intervertebral spacing between adjacent vertebrae, such forms may also serve to at least partially minimize or limit distraction of the adjacent vertebrae by virtue of the gripping portions and dampers of the various engagement members actually grasping the laminar regions of the vertebrae. Furthermore, while some materials for certain components have been disclosed herein, other materials capable of serving the principles and functions discussed are intended to be within the scope of the present invention. For example, in general, the materials utilized for the spinal stabilization systems should be bio-compatible materials. In one form, the saddle members of the engagement members that abuttingly engage the laminar regions of the vertebrae may include a polyetheretherketone, some other high fatigue life polymer, or any other bio-compatible material capable of providing a desired result for any one of a number of applications.

Further yet, it should be appreciated that while a number of the above-described forms of the present invention include combinations of multiple components cooperating to limit at least reduction of the intervertebral spacing or distraction of the vertebrae, other combinations of the systems and/or components described herein or derived therefrom are also intended to be within the scope of the present invention. Finally, one should readily recognize from the description provided above, and from the accompanying drawings and claims that various changes, modifications and variations not explicitly disclosed herein may be made without departing from the spirit and scope of the present invention.

What is claimed is:

1. A spinal stabilization system, comprising:
   a laminar support member for being engaged between respective laminar regions of adjacent, upper and lower vertebrae;
   an upper seating portion of the laminar support member having a saddle configuration that opens upwardly for receiving the laminar region of the upper vertebra;
   a lower seating portion of the laminar support member having a saddle configuration that opens downwardly opposite to the upwardly opening upper seating portion for receiving the laminar region of the lower vertebra so that the upper and lower seating portions face in opposite directions;
   a resilient middle portion of the laminar support member having opposite side portions, the resilient middle portion being positioned between the upper and lower seating portions;
   a through opening extending through the resilient middle portion; and
   an actuating mechanism having an elongate shaft disposed in the through opening, a first flange coupled to one of the side portions and a second flange coupled to the other of the side portions, the elongate shaft operably coupled to the first and second flanges such that rotation of the elongate shaft in a first direction draws the opposite side portions of the resilient middle portion towards one another while shifting the upper and lower seating portions away from each other in an expanded configuration, and rotation of the elongate shaft in a second direction shifts the opposite side portions of the resilient member away from one another while drawing the upper and lower seating portions towards each other in a compressed configuration,
   wherein the through opening changes configuration and the upper and lower seating portions remain facing in the same opposite directions as the actuating mechanism is operated to shift the upper and lower seating portions between the expanded and compressed configurations.

2. The spinal stabilization system of claim 1 wherein the elongate shaft includes a threaded portion to engage at least one of the first and second flanges and draw the first and second flanges towards one another in the expanded configuration.

3. A spinal stabilization system, comprising:
   a laminar support member for being engaged between respective laminar regions of adjacent, upper and lower vertebrae;
   an upper seating portion of the laminar support member having a saddle configuration that opens upwardly for receiving the laminar region of the upper vertebra;
   a lower seating portion of the laminar support member having a saddle configuration that opens downwardly opposite to the upwardly opening upper seating portion for receiving the laminar region of the lower vertebra so that the upper and lower seating portions face in opposite directions;
   a resilient middle portion of the laminar support member having opposite side portions, the resilient middle portion being positioned between the upper and lower seating portions;
   a through opening extending through the resilient middle portion; and
   an actuating mechanism having a generally elliptical shape with an X-axis longer than a Y-axis, the actuating mechanism disposed in the through opening such that when the X-axis is aligned in an inferior/superior orientation, the opposite side portions of the resilient middle portion are drawn towards one another with the upper and lower seating portions shifted away from each other in an expanded configuration, and rotation of the actuating mechanism such that the X-axis is aligned in a lateral direction shifting the opposite side portions of the resilient member away from one another while drawing the upper and lower seating portions towards each other in a compressed configuration,
   wherein the through opening changes configuration and the upper and lower seating portions remain facing in the same opposite directions as the actuating mechanism is operated to shift the upper and lower seating portions between the expanded and compressed configurations.

4. The spinal stabilization system of claim 3 wherein the resilient middle portion further includes one of a groove or ridge while the actuating mechanism includes the other of the groove or ridge whereby the groove and ridge cooperate to retain the actuating mechanism in the through opening.

5. The spinal stabilization system of claim 3 wherein the resilient middle portion further includes one of an alignment notch or protrusion while the actuating mechanism includes the other of the alignment notch or protrusion to retain the actuating mechanism with the X-axis in the inferior/superior orientation.

* * * * *